US012606598B2

(12) United States Patent　　　　　　　(10) Patent No.:　US 12,606,598 B2
Ambady et al.　　　　　　　　　　　　　　 (45) Date of Patent:　　Apr. 21, 2026

(54) CHIMERIC KLEBICINS

(71) Applicant: Bactoclear Holdings PTE, Ltd., Singapore (SG)

(72) Inventors: Anisha Ambady, Bangalore (IN); Chemira Biddappa Appaiah, Bangalore (IN); Vivek Daniel Paul, Bangalore (IN); R. Sanjeev Saravanan, Bangalore (IN); Keerthana Anbalagan, Tamil Nadu (IN)

(73) Assignee: Bactoclear Holdings PTE, Ltd., Singapore (SG)

( * ) Notice: Subject to any disclaimer, the term of this patent is extended or adjusted under 35 U.S.C. 154(b) by 388 days.

(21) Appl. No.: 17/811,492

(22) Filed: Jul. 8, 2022

(65) Prior Publication Data

US 2024/0010689 A1　　Jan. 11, 2024

(30) Foreign Application Priority Data

Jul. 12, 2021　(IN) .............................. 202141031183

(51) Int. Cl.
　*C07K 14/26*　　(2006.01)
　*A61K 9/00*　　(2006.01)
　*A61K 38/16*　　(2006.01)
　*A61P 31/04*　　(2006.01)

(52) U.S. Cl.
　CPC ............ *C07K 14/26* (2013.01); *A61K 9/0019* (2013.01); *A61K 9/0073* (2013.01); *A61K 38/164* (2013.01); *A61P 31/04* (2018.01); *C07K 2319/00* (2013.01)

(58) Field of Classification Search
　CPC .. C07K 14/26; C07K 2319/00; A61K 9/0019; A61K 9/0073; A61K 38/164; A61P 31/04
　See application file for complete search history.

(56) References Cited

U.S. PATENT DOCUMENTS

| | | | |
|---|---|---|---|
| 4,673,541 A | 6/1987 | Watanabe et al. | |
| 6,160,089 A | 12/2000 | Honjo et al. | |
| 6,436,674 B1 | 8/2002 | Honjo et al. | |
| 2020/0010517 A1 | 1/2020 | Hahn et al. | |
| 2021/0002706 A1 | 1/2021 | Mahfouz et al. | |
| 2021/0163546 A1 | 6/2021 | Ambady et al. | |

FOREIGN PATENT DOCUMENTS

| | | | |
|---|---|---|---|
| WO | 02086075 A2 | 10/2002 | |
| WO | WO-2019116392 A1 * | 6/2019 | ............. A01N 63/10 |
| WO | 2020/245376 A1 | 12/2020 | |

OTHER PUBLICATIONS

Internaitonal Search Report in PCT/IN2022/050631, mailed Mar. 29, 2023, 5 pages.

Barreteau et al., "Characterization of Colicin M and its Orthologs Targeting Bacterial Cell Wall Peptidoglycan Biosynthesis," Microbial Drug Resistance 18(3):222-229, 2012. (8 pages).

Batzer et al., "Enhanced evolutionary PCR using oligonucleotides with inosine at the 3'-terminus," Nucleic Acids Research 19(18):5081, Jul. 12, 1991. (1 page).

Beaucage et al., "Deoxynucleoside Phosphoramidites—A New Class of Key Intermediates for Deoxypolynucleotide Synthesis," Tetrahedron Letters 22(20):1859-1862, 1981. (4 pages).

El Ghachi et al., "Colicin M Exerts Its Bacteriolytic Effect via Enzymatic Degradation of Undecaprenyl Phosphate-linked Peptidoglycan Precursors," The Journal of Biological Chemistry 281(32):22761-22772, Aug. 11, 2006. (12 pages).

Gray et al., "Periplasmic production of correctly processed human growth hormone in *Escherichia coli*: natural and bacterial signal sequences are interchangeable," Gene 39:247-254, 1985. (8 pages).

Gross et al., "Colicin M is inactivated during import by its immunity protein," Mol Gen Genet 251:388-396, 1996. (9 pages).

Köhler et al., "Continuous cultures of fused cells secreting antibody of predefined specificity," Nature 256:495-497, Aug. 7, 1975. (3 pages).

Köhler et al., "Derivation of specific antibody-producing tissue culture and tumor lines by cell fusion," Eur. J. Immunol. 6:511-519, 1976. (9 pages).

Morrison et al., "Transformation in *Escherichia coli*: Cryogenic Preservation of Competent Cells," Journal of Bacteriology 132(1):349-351, 1977. (3 pages).

Needham-VanDevanter et al., "Characterization of an adduct between CC-1065 and a defined oligodeoxynucleotide duplex," Nucleic Acids Research 12(15):6159-6168, 1984. (10 pages).

Ohtsuka et al., "An Alternative Approach to Deoxyoligonucleotides as Hybridization Probes by Insertion of Deoxyinosine at Ambiguous Codon Positions," The Journal of Biological Chemistry 260(5):2605-2608, Mar. 10, 1985. (4 pages).

Rossolini et al., "Use of deoxyinosine-containing primers vs degenerate primers for polymerase chain reaction based on ambiguous sequence information," Molecular and Cellular Probes 8:91-98, 1994. (8 pages).

Wallace et al., "A set of synthetic oligodeoxyribonucleotide primers for DNA sequencing in the plasmid vector pBR322," Gene 16:21-26, 1981. (6 pages).

* cited by examiner

*Primary Examiner* — Jeffrey Stucker
*Assistant Examiner* — Brittney E Donoghue
(74) *Attorney, Agent, or Firm* — Seed IP Law Group LLP

(57)　　　　　ABSTRACT

The present invention provides chimeric klebicins by combining translocation, receptor-binding, and bactericidal domains originated from different klebicins to achieve improved target cell range and bactericidal activity. Also provided are related compositions, kits, and methods of use of these chimeric klebicins.

15 Claims, 22 Drawing Sheets

Specification includes a Sequence Listing.

Domains in P775:

P775: | P628 TD RBD | | P764 TD RD KD |    Mw:88.6 kDa
Theoretical pI : 9.13

Protein expression profile in crude supernatant:

| Lane-1 | Marker |
|--------|--------|
| Lane-2 | Uninduced supernatant - 20µl |
| Lane-3 | Uninduced pellet - 20µl |
| Lane-4 | Induced supernatant - 30µl |
| Lane-5 | Induced pellet - 30µl |

Purified P775 protein profile:

Lawn inhibition on *K. pneumoniae* ATCC13883:

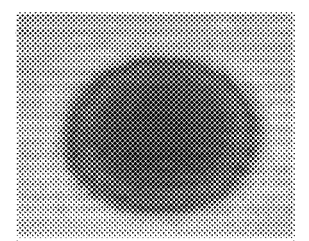 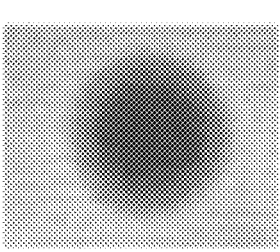 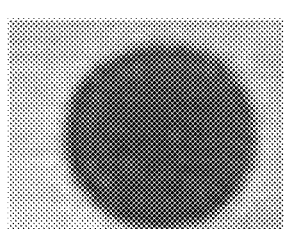
ATCC13883 WT        P628$^R$ 32.1        P628$^R$ 32.3
FIGURE 5A
| Strain | MIC (μg/ml) in CAA | |
|---|---|---|
| | P628 | P775 |
| ATCC13883 WT | 2 | 4 |
| 628$^R$ 32.1 | >45 | 4 |
| 628$^R$ 32.3 | >45 | 4 |
FIGURE 5B

Domains in P810:
| P810: | P764 TD RD | P774 RD | P764 KD | Mw:50.45 kDa |
| --- | --- | --- | --- | --- |
Theoretical pI :8.89
FIGURE 6A
Expression profile in crude supernatant:
M  Sup
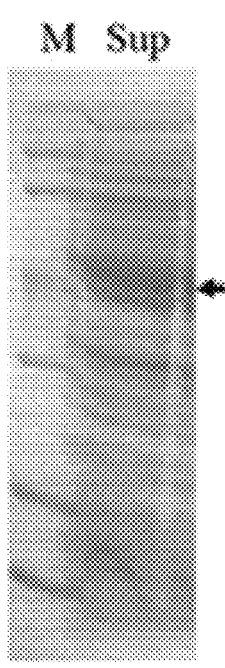
FIGURE 6B
Lawn inhibition on *K. pneumoniae*
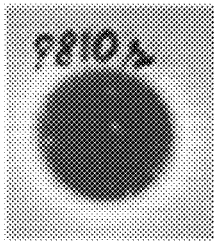
FIGURE 6C

Domains in P821:
P821: | P628 TD RBD | | P801 TD RD KD | Mw:78.3
Theoretical pI : 8.67
FIGURE 7A
Purified protein:
M        P821
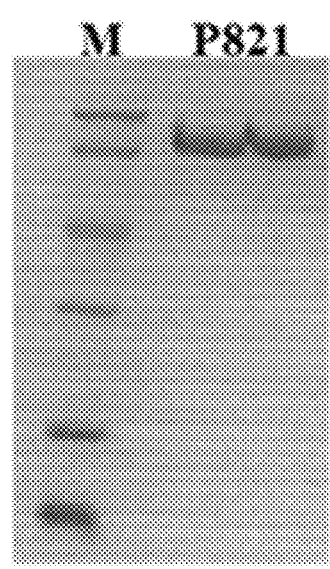
FIGURE 7B
Lawn inhibition on *K. pneumoniae*
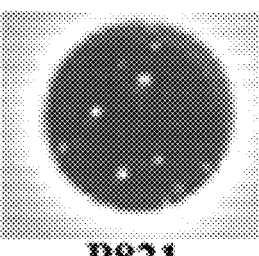
P821
FIGURE 7C

Domains in P823:

P823:  | P628 TD RD | Flexible linker | P801 TD RD KD |   Mw:77.9
Theoretical pI : 8.68

Expression profile in crude supernatant:

M  P823

Lawn inhibition on *K. pneumoniae*

P823

Domains in P835,P836,P837

| P835: | P628 TD RBD | | P801 FL | | Mw:77.4, pI:8.68 |

| P836: | P628 TD RBD | 4X Rigid linker | P801 FL | | Mw:79.3, pI:8.66 |

| P837: | P628 TD RBD | 5X Flexible Linker | P801 FL | | Mw:78.4, pI:8.68 |

Purified Protein

M    P835    P836    P837

**Lawn inhibition on *K. pneumoniae***

Bactericidal activity by CFU drop assay

Domains in P845,P862

Protein profile

Lawn inhibition on *K. pneumoniae*

Purified Protein

Lawn inhibition and  Assessment of hybrid activity

Domains in P867

| P867: | TssH (1-72) from P861 | P849 (54-386) | Mw: 29.7 kDa Theoretical pI : 7.7 |

Purified Protein

Lawn inhibition assay

Domains in P870

Purified Protein

M    P870

Lawn inhibition assay

Domains in P875

P875 | P801 FL | | GP36 CD |    Mw:54.3 kDa
Theoretical pI : 8.53

Purified Protein

M    P875

Lawn Inhibition assay (40 µg)

P875

ATCC 13883

B2272

Domains in P889
| P889 | P764 FL | GP36 CD | Mw:63.4 kDa
Theoretical pl : 8.73 |
FIGURE 16A
Purified Protein
M    P889
FIGURE 16B
Lawn inhibition assay
P889
ATCC 13883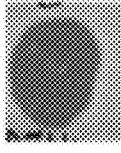
B2322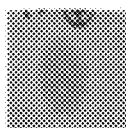
FIGURE 16C

Domains in P891

| P891 | P764 | Flexible Linker | GP36 CD | Mw:63.9 kDa<br>Theoretical pI : 8.73 |

Purified Protein

M   P891

Lawn inhibition assay

ATCC 13883

B2322

Domains in P892

Purified Protein

Lawn inhibition on *K. pneumoniae*

CHIMERIC KLEBICINS

SEQUENCE LISTING

The instant application contains a Sequence Listing which has been submitted electronically in XML file format and is hereby incorporated by reference in its entirety. Said XML copy, created on Aug. 3, 2022, is named 105995-1330716-002610US_SL.xml and is 168,088 bytes in size.

BACKGROUND OF THE INVENTION

Antibacterial proteins produced by bacteria to kill related bacterial species, bacteriocins present important means for bacteria to compete for environmental resources. A bacteriocin includes several distinct domains, responsible for translocation into its target bacteria, for binding to its receptor and for exerting its bactericidal activity. The receptor-binding domain and the translocation domain act first allow a bacteriocin to gain entry into susceptible bacterial cells by utilizing cell-surface receptors of target bacteria and translocation machinery. Upon being transported across the cell membrane, the killing domain of the bacteriocin then functions to cause the death of the target bacterial cells. On the other hand, the bacteriocin-producing bacteria are themselves protected against killing effect of such bacteriocins by virtue of the presence of certain immunity proteins that can neutralize the bacteriocins. Thus, target cell susceptibility is predicated in the fact that cell surface receptors and translocation proteins are present whereas cognate immunity proteins are absent. These factors together determine a narrow range of effectiveness for a naturally-occurring bacteriocin.

Klebicins are bacteriocins produced by *Klebsiella* spp. and specifically kill other susceptible members of the *Klebsiella* genus, such as *Klebsiella pneumoniae*, a drug-resistant pathogenic bacterial species known to cause severe infectious diseases and thus a therapeutic target in the treatment of these diseases. Since the therapeutic use of klebicins tends to suffer from the disadvantages of narrow target ranges within the *Klebsiella* genus, there exists a pressing need for developing new and improved klebicins with broader target cell ranges in order to effectively treat *Klebsiella* infections. The invention addresses this and other related needs by disclosing novel chimeric bacteriocins, which are characterized by the inclusion of multiple domains from multiple original klebicins, retaining activity of both individual klebicins, and are capable of utilizing multiple receptors for entry. These new chimeric klebicins also have a reduced frequency of resistance (FoR), and the levels are equal or better than the individual klebicin combination. Lastly, these chimeric klebicins are able to achieve increased effective range—their bactericidal activity can be exerted across the activity spectrum of the individual klebicins, from which the individual domains of klebicins are derived.

BRIEF SUMMARY OF THE INVENTION

With the goal in mind to develop new bacteriocins with improved properties such as broad target bacterial cell range and enhanced anti-bacterial activities, the present inventors engineered a panel of chimeric klebicins employing different combinations of translocation domain, receptor-binding domain, and bactericidal domain (or "killing domain") taken from different naturally-occurring klebicins to study their bactericidal efficacy against the bacteria of the *Klebsiella* genus, especially *Klebsiella pneumoniae*. As such, in a first aspect, this invention provides new chimeric klebicin polypeptides that are capable of suppressing the growth of the *Klebsiella* spp. bacteria, e.g., *Klebsiella pneumoniae*. The chimeric polypeptide comprises one or more translocation domains, one or more receptor-binding domains, and a killing domain, with each of these domains taken from a naturally-occurring klebicin, and the killing domain and at least one of the receptor-binding domains taken from two different naturally-occurring klebicins. In some embodiments, the polypeptide comprises, from its N-terminus to C-terminus, the translocation domain(s), the receptor-binding domain(s), and the killing domain. In some embodiments, there may be two receptor-binding domains and two translocation domains in a chimeric klebicin polypeptide, and the two receptor-binding domains and translocation domains are from two different naturally-occurring klebicins. In some embodiments, the chimeric polypeptide may further comprise a peptide linker, which may be either a flexible linker or a rigid linker, located between the receptor-binding domain (e.g., the one closest to the C-terminus of the polypeptide) and the killing domain. In some embodiments, the killing domain comprises a full-length naturally-occurring klebicin. In some embodiments, the translocation domain and one of the receptor-binding domains are derived from P628 or P764. In some embodiments, the killing domain comprises full length P764 or P801. In some embodiments, the two different receptor-binding domains are taken from P764 and P774. In some embodiments, the polypeptide consists of or consists essentially of the components named in the specific combinations in Table 3 of this disclosure (see column 3 "Domain details"). For example, the chimeric klebicin may comprise or consists of one of the amino acid sequences set forth in Table 3, e.g., SEQ ID NO:7, 33, 45, 47, 51, 57, 59, 61, 65, 67, 69, 71, 73, or 75. Also provided is a composition comprising the chimeric polypeptide of this invention and a physiologically acceptable excipient. In some cases, the composition is formulated for administration either systemically or locally, e.g., in a suitable form for injection or for inhalation or for local delivery.

This invention also provides the polynucleotide sequences encoding the chimeric polypeptides described above and herein, their corresponding expression cassettes, vectors, and host cells. In some embodiments, this invention provides a nucleic acid comprising a polynucleotide sequence encoding the polypeptide comprising or consisting of SEQ ID NO:8, 34, 46, 48, 52, 58, 60, 62, 66, 68, 70, 72, 74, or 76. In some embodiments, this invention provides an expression cassette comprising such a polynucleotide sequence, or a vector comprising the expression cassette, or a host cell comprising the expression cassette or the vector described above or herein.

In some embodiments, a method is provided for recombinantly producing the chimeric klebicin polypeptide described above and herein. The method comprising culturing the host cell comprising an expression cassette (such as a part of a vector) encoding such a polypeptide under conditions permitting the expression of the chimeric polypeptide encoded by the expression cassette or the vector.

In a second aspect, the present invention provides methods for suppressing growth of *Klebsiella pneumoniae* by applying an effective amount of the composition containing the chimeric klebicin of the present invention to a location where *Klebsiella pneumoniae* is present. In some embodiments, the composition is applied to a patient suffering from a *Klebsiella pneumoniae* infection by injection, such as a liquid form like a solution or emulsion or suspension for intravenous or intramuscular or subcutaneous injection, or by inhalation of an aerosolized or nebulized spray or mist etc., or by local delivery such as topical application, for example, the polypeptide is applied in the form of a paste, cream, lotion, ointment, spray, or as an incorporated part of a patch/bandage or wound dressing.

A related aspect of this invention is the use of the chimeric klebicin polypeptide described herein for suppression of *Klebsiella pneumoniae* growth or the production of a medicament for treating *Klebsiella pneumoniae* infection. In some embodiments, the polypeptide is present in a composition formulated for injection, or for inhalation, or for local application. In some embodiments, the polypeptide used in the claimed method may comprise or consist of SEQ ID NO:7; or the polypeptides used in the claimed method may comprise or consist of SEQ ID NO:33; or the polypeptides used in the claimed method may comprise or consist of SEQ ID NO:45; or the polypeptides used in the claimed method may comprise or consist of SEQ ID NO:47; or the polypeptides used in the claimed method may comprise or consist of SEQ ID NO:51; or the polypeptides used in the claimed method may comprise or consist of SEQ ID NO:57; or the polypeptides used in the claimed method may comprise or consist of SEQ ID NO:59 or the polypeptides used in the claimed method may comprise or consist of SEQ ID NO:61; or the polypeptides used in the claimed method may comprise or consist of SEQ ID NO:65; or the polypeptides used in the claimed method may comprise or consist of SEQ ID NO:67; or the polypeptides used in the claimed method may comprise or consist of SEQ ID NO:69; or the polypeptides used in the claimed method may comprise or consist of SEQ ID NO:71; or the polypeptides used in the claimed method may comprise or consist of SEQ ID NO:73; or the polypeptides used in the claimed method may comprise or consist of SEQ ID NO:75.

In a third aspect, the present invention provides a kit for suppressing growth of *Klebsiella pneumoniae*, comprising a first container containing a composition comprising an effective amount of the chimeric klebicin polypeptide described herein. In some cases, the composition is formulated for injection. In some cases, the composition is formulated for inhalation. In some cases, the composition is formulated for local delivery. In some embodiments, the kit may further comprise a manual providing instructions for a user of the kit. Typically, the kit includes a first container containing a composition comprising an effective amount of a polypeptide comprising or consisting of the amino acid sequence of SEQ ID NO:7, 33, 45, 47, 51, 57, 59, 61, 65, 67, 69, 71, 73, or 75.

BRIEF DESCRIPTION OF THE DRAWINGS

FIGS. 5A-5B. Activity of P775 on P628-resistant mutants of ATCC13883. Lawn inhibition assay on wild-type (WT) and resistant mutants (R) (FIG. 5A) and MIC (FIG. 5B).

FIGS. 6A-6C. Details of P810 with domain architecture (FIG. 6A), protein expression profile (FIG. 6B) and activity on *K. pneumoniae* ATCC13883 by lawn inhibition assay (FIG. 6C).

FIGS. 7A-7C. Details of P821 with domain architecture (FIG. 7A), purified protein profile (FIG. 7B) and activity on *K. pneumoniae* ATCC13883 by lawn inhibition assay (FIG. 7C).

FIGS. 16A-16C. Details of P889 with domain architecture (FIG. 16A), purified protein profile (FIG. 16B). Activity by lawn inhibition assay (FIG. 16C).

DEFINITIONS

Figure 1:
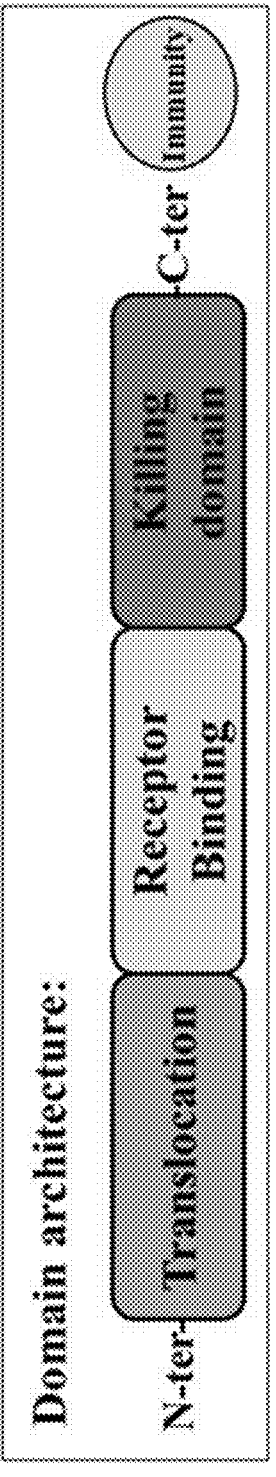
FIG. 1. Domains in a bacteriocin.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid is used interchangeably with gene, cDNA, and mRNA encoded by a gene.

The term "gene" means the segment of DNA involved in producing a polypeptide chain. It may include regions preceding and following the coding region (leader and trailer) as well as intervening sequences (introns) between individual coding segments (exons).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds having a structure that is different from the general chemical structure of an amino acid, but that functions in a manner similar to a naturally occurring amino acid.

There are various known methods in the art that permit the incorporation of an unnatural amino acid derivative or analog into a polypeptide chain in a site-specific manner, see, e.g., WO 02/086075.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, W. H. Freeman and Co., N. Y. (1984)).

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In the present application, amino acid residues are numbered according to their relative positions from the left most residue, which is numbered 1, in an unmodified wild-type polypeptide sequence.

"Polypeptide," "peptide," and "protein" are used interchangeably herein to refer to a polymer of amino acid residues. All three terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins, wherein the amino acid residues are linked by covalent peptide bonds.

The term "recombinant" when used with reference, e.g., to a cell, or a nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a polynucleotide sequence. As used herein, a promoter includes necessary polynucleotide sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a polynucleotide expression control sequence (such as a promoter, or array of transcription factor binding sites) and a second polynucleotide sequence, wherein the expression control sequence directs transcription of the polynucleotide sequence corresponding to the second sequence.

An "expression cassette" is a nucleic acid construct, generated recombinantly or synthetically, with a series of specified polynucleotide elements that permit transcription of a particular polynucleotide sequence in a host cell. An expression cassette may be part of a plasmid, viral genome, or nucleic acid fragment. Typically, an expression cassette includes a polynucleotide to be transcribed, operably linked to a promoter.

The term "translocation domain" as used in the context of describing a segment of a klebicin refers to the segment that is responsible for mediating a process by which the protein is introduced into or taken up by a target *Klebsiella* bacterial cell across the cell membrane.

The term "receptor-binding domain" as used in the context of describing a segment of a klebicin refers to the segment having the capability of binding one or more components (e.g., receptors) present on the target *Klebsiella* bacterial cell membrane.

The term "killing domain" as used in the context of describing a segment of a klebicin refers to the segment responsible for the cytotoxicity of the klebicin to the target *Klebsiella* bacterial cell. For example, such cytotoxicity may be a pore-forming capability in a bacterial cell membrane or may be a lipid II-cleaving activity analogous to the activity of *E. coli* colicin M (Gross and Braun, *Mol. Gen. Genet.* 1996, 251:388-396; Barreteau et al., *Microbial. Drug Resist.* 2012, 18:222-229; and El Ghachi et al., *J. Biol. Chem.* 2006, 281:22761-22772), or nuclease activity (Dnase or Rnase). When used in describing the structure of a particular chimeric klebicin of this invention, the term "killing domain" may broadly encompass a full-length naturally-occurring klebicin or a modified version thereof (e.g., deletion, insertion, and/or substitution of one or more amino acid at one or more locations within of a full-length wild-type klebicin) that retains the capability of killing the target bacterial cells.

The term "consisting essentially of," or its grammatical variations, as used in the context of describing the components of a chimeric klebicin of this invention, describes the chimeric klebicin as containing only these specifically named components (such as the translocation, receptor-binding, and kill domains, as well as peptide linkers identified in column 3 "Domain details" in Table 3 of this disclosure), excluding other components of the same or similar nature, but permitting the optional presence of up to additional 1, 2, 3, 4, 5, 6, 7, 8, 9, or up to 10 amino acids at the juncture between any two of the specified components of the chimeric klebicin as well as up to additional 1, 2, 3, 4, 5, 6, 7, 8, 9, 10, 11, 12, 13, 14, 15, 16, 17, 18, 19, or 20 amino acids at the N-terminus and/or the C-terminus.

The term "heterologous" as used in the context of describing the relative location of two elements, refers to the two elements such as polynucleotide sequences (e.g., a promoter or a protein/polypeptide-encoding sequence) or polypeptide sequences (e.g., a chimeric klebicin sequence selected from SEQ ID NOs:7, 33, 45, 47, 51, 57, 59, 61, 65, 67, 69, 71, 73, and 75 or another peptide sequence serving as a fusion partner with a chimeric klebicin sequence) that are not naturally found in the same relative positions. Thus, a "heterologous promoter" of a gene refers to a promoter that is not naturally operably linked to that gene. Similarly, a "heterologous polypeptide" or "heterologous polynucleotide" to a chimeric klebicin or its encoding sequence is one derived from an origin other than any of the naturally-occurring klebicins contributing any one of the translocation, receptor-binding, and kill domains, or is one derived from such a naturally-occurring klebicin but not naturally connected to any part of chimeric klebicin in the same fashion as found in nature. The fusion of a chimeric klebicin (or its coding sequence) with a heterologous polypeptide (or polynucleotide sequence) should typically result in a longer polypeptide (or polynucleotide sequence) retaining the same biological activity, for example, cytotoxicity towards the same targeted bacterial species.

The term "inhibit/inhibiting/inhibition" or "suppress/suppressing/suppression," as used herein, refers to any detectable negative effect on a target biological process, such as bacterial cell proliferation or bacterial cell presence. Typically, an inhibition is reflected in a decrease of at least 10%, 20%, 30%, 40%, or 50% in target process (e.g., the growth rate or level of a pertinent bacterium such as *K. pneumoniae*) upon application of an inhibitory substance (e.g., any one of the chimeric klebicins set forth in SEQ ID NO:7, 33, 45, 47, 51, 57, 59, 61, 65, 67, 69, 71, 73, or 75), when compared to a control where the inhibitor is not applied.

The term "treat" or "treating," as used in this application, describes to an act that leads to the elimination, reduction, alleviation, reversal, or prevention or delay of onset or recurrence of any symptom of a relevant condition. In other words, "treating" a condition encompasses both therapeutic and prophylactic intervention against the condition.

The term "effective amount" as used herein refers to an amount of a given substance that is sufficient in quantity to produce a desired effect. For example, an effective amount of a chimeric klebicin for suppressing the growth of a specific bacterial species such as *K. pneumoniae* is the amount of the chimeric protein to achieve a decreased level (including to an undetectable level) of *K. pneumoniae* in a sample taken from a recipient, who is given the chimeric enzyme for a condition involving the bacterium's presence, e.g., as reflected or measured in the type of samples from the recipient. An amount adequate to achieve an intended effect in the therapeutic context is defined as the "therapeutically effective dose." The dosing range varies with the nature of the therapeutic agent being administered and other factors such as the route of administration and the severity of a patient's condition.

As used herein, a "host cell" is a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

As used herein, the term "about" denotes a range encompassing +/−10% of a pre-determined value. For example, "about 10" means a range of 9 to 11.

DETAILED DESCRIPTION OF THE INVENTION

I. Introduction

Previously, polypeptides of bacterial origins possessing the activity of suppressing bacterial growth, especially for the genus of *Klebsiella*, by way of lysis of targeted bacteria cell wall and therefore killing the bacteria have been disclosed, see, e.g., WO2020/245376. These naturally-occurring polypeptides generally comprise the translocation domain (TD), receptor-binding domain (RD), and cytotoxicity domain (or killing domain, KD) as the main structural components.

The present inventors have constructed and identified chimeric polypeptides having the same general structural features by mixing and matching the translocation domain, receptor-binding domain, and cytotoxic domain (or "killing domain") taken from different naturally-occurring klebicins, which possess highly unique and exceptionally valuable characteristics of bactericidal activity against certain target bacteria species within the genus of *Klebsiella*, especially *K. pneumoniae*. This disclosure relates to the compositions and methods of use based on these newly constructed and identified chimeric polypeptides with desirable anti-bacterial activity.

II. Production of Chimeric Polypeptides

A. General Recombinant Technology

Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized, e.g., according to the solid phase phosphoramidite triester method first described by Beaucage & Caruthers, *Tetrahedron Lett.* 22: 1859-1862 (1981), using an automated synthesizer, as described in Van Devanter et. al., *Nucleic Acids Res.* 12: 6159-6168 (1984). Purification of oligonucleotides is performed using any art-recognized strategy, e.g., native acrylamide gel electrophoresis or anion-exchange HPLC as described in Pearson & Reanier, *J. Chrom.* 255: 137-149 (1983).

The sequence of a polynucleotide encoding a chimeric polypeptide and its variants can be verified after cloning or subcloning using, e.g., the chain termination method for sequencing double-stranded templates of Wallace et al., *Gene* 16: 21-26 (1981).

B. Cloning and Subcloning of Coding Sequences for Chimeric Polypeptides

Polynucleotide sequences encoding chimeric klebicin polypeptides can be determined based on their amino acid sequences (e.g., any one of SEQ ID NOs:7, 33, 45, 47, 51, 57, 59, 61, 65, 67, 69, 71, 73, and 75) and available information from earlier publications (e.g., WO2020/245376).

Upon acquiring a polynucleotide sequence encoding a chimeric polypeptide, the coding sequence can be modified as appropriate (e.g., adding a coding sequence for a heterologous tag, such as an affinity tag, for example, 6×His tag (SEQ ID NO: 77) or GST tag; or further mutated) and then be subcloned into a vector, for instance, an expression vector, so that a recombinant chimeric polypeptide can be produced from the resulting construct, for example, after transformation and culturing host cells under conditions permitting recombinant protein expression directed by a promoter operably linked to the coding sequence.

C. Modification of Nucleic Acids for Preferred Codon Usage in a Host Organism

The polynucleotide sequence encoding a chimeric klebicin polypeptide can be further altered to coincide with the preferred codon usage of a particular host. For example, the preferred codon usage of one strain of bacterial cells can be used to derive a polynucleotide that encodes a chimeric klebicin of the invention and includes the codons favored by this strain. The frequency of preferred codon usage exhibited by a host cell can be calculated by averaging frequency of preferred codon usage in a large number of genes expressed by the host cell (e.g., calculation service is available from web site of the Kazusa DNA Research Institute, Japan). This analysis is preferably limited to genes that are highly expressed by the host cell.

At the completion of modification, the coding sequences are verified by sequencing and are then subcloned into an appropriate expression vector for recombinant production of the chimeric klebicin polypeptides.

IV. Expression and Purification of Recombinantly Produced Polypeptides

Following verification of the coding sequence, the chimeric polypeptides of the present invention can be produced using routine techniques in the field of recombinant genetics, relying on the polynucleotide sequences encoding the polypeptides disclosed herein.

A. Expression Systems

To obtain high level expression of a nucleic acid encoding a chimeric klebicin polypeptide of the present invention, one typically subclones a polynucleotide encoding the polypeptide into an expression vector that contains a strong promoter to direct transcription, a transcription/translation terminator and a ribosome binding site for translational initiation. Suitable bacterial promoters are well known in the art and described, e.g., in Sambrook and Russell, and Ausubel et al., Bacterial expression systems for expressing a recombinant polypeptide are available in, e.g., *E. coli, Bacillus* sp., *Salmonella*, and *Caulobacter*. Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically includes a transcription unit or expression cassette that contains all the additional elements required for the expression of the chimeric polypeptide in host cells. A typical expression cassette thus contains a promoter operably linked to the coding sequence and signals required for efficient polyadenylation of the transcript, ribosome binding sites, and translation termination. The nucleic acid sequence encoding the chimeric polypeptide may be linked to a cleavable signal peptide sequence to promote secretion of the recombinant polypeptide by the transformed cell. Such signal peptides include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette may also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., His or c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMT010/A$^+$, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as a baculovirus vector in insect cells, with a polynucleotide sequence encoding the chimeric polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary. Similar to antibiotic resistance selection markers, metabolic selection markers based on known metabolic pathways may also be used as a means for selecting transformed host cells.

When periplasmic expression of a recombinant protein (e.g., a chimeric klebicin polypeptide of the present invention) is desired, the expression vector further comprises a sequence encoding a secretion signal, such as the *E. coli* OppA (Periplasmic Oligopeptide Binding Protein) secretion signal or a modified version thereof, which is directly connected to 5' of the coding sequence of the protein to be expressed. This signal sequence directs the recombinant protein produced in cytoplasm through the cell membrane into the periplasmic space. The expression vector may further comprise a coding sequence for signal peptidase 1, which is capable of enzymatically cleaving the signal sequence when the recombinant protein is entering the periplasmic space. More detailed description for periplasmic production of a recombinant protein can be found in, e.g., Gray et al., *Gene* 39: 247-254 (1985), U.S. Pat. Nos. 6,160,089 and 6,436,674.

B. Transfection Methods

Standard transfection methods are used to produce bacterial, mammalian, yeast, insect, or plant cell lines that express large quantities of a recombinant polypeptide, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132: 349-351 (1977); Clark-Curtiss & Curtiss, *Methods in Enzymology* 101: 347-362 (Wu et al., eds, 1983).

Any of the well-known procedures for introducing foreign nucleotide sequences into host cells may be used. These include the use of calcium chloride transformation, calcium phosphate transfection, polybrene, protoplast fusion, electroporation, liposomes, microinjection, plasma vectors, viral vectors and any of the other well-known methods for introducing cloned genomic DNA, cDNA, synthetic DNA, or other foreign genetic material into a host cell (see, e.g., Sambrook and Russell, supra). It is only necessary that the particular genetic engineering procedure used be capable of successfully introducing at least one gene into the host cell capable of expressing the recombinant polypeptide.

C. Detection of Recombinant Expression of Chimeric Klebicin in Host Cells

After the expression vector is introduced into appropriate host cells, the transfected cells are cultured under conditions favoring expression of the chimeric klebicin polypeptide. The cells are then screened for the expression of the recombinant polypeptide, which is subsequently recovered from the culture using standard techniques (see, e.g., Scopes, *Protein Purification: Principles and Practice* (1982); U.S. Pat. No. 4,673,641; Ausubel et al., supra; and Sambrook and Russell, supra).

Several general methods for screening gene expression are well known among those skilled in the art. First, gene expression can be detected at the nucleic acid level. A variety of methods of specific DNA and RNA measurement using nucleic acid hybridization techniques are commonly used (e.g., Sambrook and Russell, supra). Some methods involve an electrophoretic separation (e.g., Southern blot for detecting DNA and Northern blot for detecting RNA), but detection of DNA or RNA can be carried out without electrophoresis as well (such as by dot blot). The presence of nucleic acid encoding a chimeric klebicin polypeptide in transfected cells can also be detected by PCR or RT-PCR using sequence-specific primers.

Second, gene expression can be detected at the polypeptide level. Various immunological assays are routinely used by those skilled in the art to measure the level of a gene product, particularly using polyclonal or monoclonal antibodies that react specifically with a chimeric klebicin of the present invention (e.g., Harlow and Lane, *Antibodies, A Laboratory Manual*, Chapter 14, Cold Spring Harbor, 1988; Kohler and Milstein, *Nature,* 256: 495-497 (1975)). Such techniques require antibody preparation by selecting antibodies with high specificity against the chimeric klebicin. The methods of raising polyclonal and monoclonal antibodies are well established and their descriptions can be found in the literature, see, e.g., Harlow and Lane, supra; Kohler and Milstein, Eur. *J. Immunol.,* 6: 511-519 (1976).

D. Purification of Recombinantly Produced Chimeric Klebicins

Once the expression of a recombinant chimeric klebicin polypeptide in transformed or transfected host cells is confirmed, the host cells are then cultured in an appropriate scale for the purpose of purifying the recombinant polypeptide.

1. Purification of Recombinantly Produced Polypeptides from Bacteria

When the chimeric klebicin polypeptides of the present invention are produced recombinantly by transformed bacteria in large amounts, typically after promoter induction, although expression can be constitutive, the polypeptides may form insoluble aggregates. There are several protocols that are suitable for purification of protein inclusion bodies. For example, purification of aggregate proteins (hereinafter referred to as inclusion bodies) typically involves the extraction, separation and/or purification of inclusion bodies by disruption of bacterial cells, e.g., by incubation in a buffer of about 100-150 μg/ml lysozyme and 0.1% Nonidet P40, a non-ionic detergent. The cell suspension can be ground using a Polytron grinder (Brinkman Instruments, Westbury, NY). Alternatively, the cells can be sonicated on ice. Alternate methods of lysing bacteria are described in Ausubel et al. and Sambrook and Russell, both supra, and will be apparent to those of skill in the art.

The cell suspension is generally centrifuged and the pellet containing the inclusion bodies resuspended in buffer which does not dissolve but washes the inclusion bodies, e.g., 20 mM Tris-HCl (pH 7.2), 1 mM EDTA, 150 mM NaCl and 2% Triton-X 100, a non-ionic detergent. It may be necessary to repeat the wash step to remove as much cellular debris as possible. The remaining pellet of inclusion bodies may be resuspended in an appropriate buffer (e.g., 20 mM sodium phosphate, pH 6.8, 150 mM NaCl). Other appropriate buffers will be apparent to those of skill in the art.

Following the washing step, the inclusion bodies are solubilized by the addition of a solvent that is both a strong hydrogen acceptor and a strong hydrogen donor (or a combination of solvents each having one of these properties). The proteins that formed the inclusion bodies may then be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents that are capable of solubilizing aggregate-forming proteins, such as SDS (sodium dodecyl sulfate) and 70% formic acid, may be inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of the immunologically and/or biologically active protein of interest. After solubilization, the protein can be separated from other bacterial proteins by standard separation techniques. For further description of purifying recombinant polypeptides from bacterial inclusion body, see, e.g., Patra et al., *Protein Expression and Purification* 18: 182-190 (2000).

Alternatively, it is possible to purify recombinant polypeptides, e.g., a chimeric klebicin polypeptide, from bacterial periplasm. Where the recombinant protein is exported into the periplasm of the bacteria, the periplasmic fraction of the bacteria can be isolated by cold osmotic shock in addition to other methods known to those of skill in the art (see e.g., Ausubel et al., supra). To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO$_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

2. Standard Protein Separation Techniques for Purification

When a recombinant polypeptide, e.g., a chimeric polypeptide of the present invention, is expressed in host cells in a soluble form, its purification can follow the standard protein purification procedure described below.

i. Solubility Fractionation

Often as an initial step, and if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol is to add saturated ammonium sulfate to a protein solution so that the resultant ammonium sulfate concentration is between 20-30%. This will precipitate the most hydrophobic proteins. The precipitate is discarded (unless the protein of interest is hydrophobic) and ammonium sulfate is added to the supernatant to a concentration known to precipitate the protein of interest. The precipitate is then solubilized in buffer and the excess salt removed if necessary, through either dialysis or diafiltration. Other methods that rely on solubility of proteins, such as cold ethanol precipitation, are well known to those of skill in the art and can be used to fractionate complex protein mixtures.

ii. Size Differential Filtration

Based on a calculated molecular weight, a protein of greater and lesser size can be isolated using ultrafiltration through membranes of different pore sizes (for example, Amicon or Millipore membranes). As a first step, the protein mixture is ultrafiltered through a membrane with a pore size that has a lower molecular weight cut-off than the molecular weight of a protein of interest, e.g., a chimeric polypeptide of the present invention. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

iii. Column Chromatography

The proteins of interest (such as a chimeric polypeptide of the present invention) can also be separated from other proteins on the basis of their size, net surface charge, hydrophobicity, or affinity for ligands. In addition, antibodies raised against a chimeric klebicin can be conjugated to column matrices and the chimeric klebicin polypeptide immunopurified. All of these methods are well known in the art.

It will be apparent to one of skill that chromatographic techniques can be performed at any scale and using equipment from many different manufacturers (e.g., Pharmacia Biotech).

V. Formulation and Administration

Various applications of the species-specific enzymatic activities can be immediately recognized. One important application is as antibacterial treatment of articles which may be contaminated in normal use. Locations, equipment, environments, or the like where target bacteria may be public health hazards may be treated using such entities. Locations of interest include public health facilities where the purpose or opportunity exists to deal with target bacteria containing materials. These materials may include waste products, e.g., liquid, solid, or air. Aqueous waste treatment plants may incorporate such to eliminate the target from effluent, whether by treatment with the enzyme entities directly, or by release of cells which produce such. Solid waste sites may introduce such to minimize possibility of target host outbreaks. Conversely, food preparation areas or equipment need to be regularly cleaned, and the invention provides compositions and means to effectively eliminate target bacteria. Medical and other public environments subject to contamination may warrant similar means to minimize growth and spread of target microorganisms. The methods may be used in contexts where sterilization elimination of target bacteria is desired, including air filtration systems for an intensive care unit.

Alternative applications include use in a veterinary or medical context. Means to determine the presence of particular bacteria, or to identify specific targets may utilize the effect of selective agents on the population or culture. Inclusion of bacteriostatic or bactericidal activities to cleaning agents, including washing of animals and pets, may be desired.

The chimeric klebicin polypeptides of this invention can be used to treat infections caused by specific, harmful bacterial species in, e.g., humans or animals, for conditions such as pneumonia, bacteremia, or urinary tract infection. These chimeric polypeptides can be administered prophylactically or can be administered to a subject that has contracted a bacterial infection. In one embodiment, the chimeric polypeptides are used to treat infections (e.g., respiratory infections) caused by one or more bacteria of a *Klebsiella* species, such as *K. pneumoniae*, and in case of respiratory viral infections to prevent the onset of bacterial secondary infections caused by *Klebsiella* species.

In one embodiment, these chimeric proteins (e.g., any one of those in Table 3, such as SEQ ID NOs:7, 33, 45, 47, 51, 57, 59, 61, 65, 67, 69, 71, 73, and 75) are used to treat humans or other animals that are infected with *K. pneumoniae*.

The route of administration and dosage will vary with the infecting bacteria strain(s), the site and extent of infection (e.g., local or systemic), and the subject being treated. The routes of administration include but are not limited to: oral, aerosol or other device for delivery to the lungs, nasal spray, intravenous (IV), intramuscular, intraperitoneal, intrathecal, intraocular, subcutaneous, vaginal, rectal, topical, lumbar puncture, intrathecal, and direct application to the brain and/or meninges. Excipients that can be used as a vehicle for the delivery of the therapeutic will be apparent to those skilled in the art. For example, the chimeric klebicin could be kept in a lyophilized form and be dissolved just prior to administration by IV injection. The dosage of administration is contemplated to be in the range of about 0.03, 0.1, 0.3, 1, 3, 10, 30, 100, 300, 1000, 3000, 10000 or more klebicin molecules per bacterium in the host infection. Depending upon the size of the klebicin, which may itself be tandemly associated, or in multiple subunit form (dimer, trimer, tetramer, pentamer, and the like) or in combination with one or more other entities, e.g., enzymes or fragments of different specificity, the dose may be about 1 million to about 10 trillion/per kg/per day, and preferably about 1 trillion/per kg/per day.

The therapeutic compositions comprising at least one of the chimeric klebicins of this invention are typically administered until successful elimination of the target pathogenic bacteria is achieved. Thus the invention contemplates single dosage forms, as well as multiple dosage forms of the compositions of the invention, as well as methods for accomplishing sustained release means for delivery of such single and multi-dosages forms.

With respect to the aerosol administration to the lungs or other mucosal surfaces, the therapeutic composition is incorporated into an aerosol formulation specifically designed for administration. Many such aerosols are known in the art, and the present invention is not limited to any particular formulation. An example of such an aerosol is the Proventil inhaler manufactured by Schering-Plough, the propellant of which contains trichloromonofluoro-methane, dichlorodifluoromethane, and oleic acid. Other embodiments include inhalers that are designed for administration to nasal and sinus passages of a subject or patient. The concentrations of the propellant ingredients and emulsifiers are adjusted if necessary based on the specific composition being used in the treatment. Also useful are suppositories that are designed for direct deposit of a klebicin-containing composition to an anatomic site of a bacterial infection, e.g., urinary tract.

Methods to evaluate killing capacity of the chimeric klebicins of this invention are often similar to many methods used in assessing killing capacity of intact replicating phages. Comparing total bacterial counts with viable colony units can establish what fraction of bacteria are actually viable, and by implication, what fraction have been susceptible to the killing constructs. Other means for evaluating stasis activity may include release of intracellular contents, whether natural or loaded, or enzymatic activity on defined or prepared substrates which correspond to natural cell wall structures.

Typically, the killing will decrease bacterial replication capacity to about $\frac{1}{3}$ or less, and may affect or reduce it to about $\frac{1}{10}$, $\frac{1}{30}$, $\frac{1}{100}$, $\frac{1}{300}$, etc., to many orders of magnitude when compared to a control without exposure to a chimeric klebicin. However, even slowing the rate of bacterial replication without killing may have significant therapeutic or commercial value. Preferred genetic inactivation efficiencies may be 0.1, 0.2, 0.3, 0.5, 0.8, 1, 1.5, 2.0, 2.5, 3.0, 3.5, 4, 5, 6, 7, 8, or more log units.

This invention further contemplates pharmaceutical compositions comprising at least one chimeric klebicins described herein and a physiologically or pharmaceutically acceptable excipient. The compositions of the invention thus include formulations comprising an isolated chimeric polypeptide specifically targeting one or more bacteria of a genus such as the *Klebsiella* genus, e.g., *K. pneumoniae*. In some cases, a mixture of two, three, or four of the chimeric polypeptides may be used to enhance the target-specific bacteria killing without significant impact on other non-target bacterial species that may provide potential benefits to a patient. In this manner, the compositions of the invention can be tailored to the needs of the patient. The compounds or compositions will typically be sterile or near sterile.

By "therapeutically effective dose" herein is meant a dose that produces effects, bacteriostatic or preferably bactericidal, for which it is administered. The exact dose will depend on the purpose of the treatment, and will be ascertainable by one skilled in the art using known techniques. See, e.g., Ansel, et al. *Pharmaceutical Dosage Forms and Drug Delivery*; Lieberman (1992) *Pharmaceutical Dosage Forms* (vols. 1-3), Dekker, ISBN 0824770846, 082476918X, 0824712692, 0824716981; Lloyd (1999) *The Art, Science and Technology of Pharmaceutical Compounding*; and Pickar (1999) *Dosage Calculations*. As is known in the art, adjustments for protein degradation, systemic versus localized delivery, and rate of new protease synthesis, as well as the age, body weight, general health, sex, diet, time of administration, drug interaction, spectrum of bacterial components in the colony, and the severity of the condition may be necessary, and will be ascertainable with some experimentation by those skilled in the art.

Various physiologically or pharmaceutically acceptable excipients are well known in the art. As used herein, "physiologically or pharmaceutically acceptable excipient" refers to a material that, when combined with an active ingredient of a composition, allows the ingredient to retain its biological activity and without causing any detectable physiological reactions in a recipient. Such excipients may include stabilizers, preservatives, salt, or sugar complexes or crystals, and the like.

Exemplary pharmaceutically carriers include sterile aqueous of non-aqueous solutions, suspensions, and emulsions. Examples include, but are not limited to, standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. In other embodiments, the compositions will be incorporated into solid matrix, including slow release particles, glass beads, bandages, inserts on the eye, and topical forms such as creams, pastes, lotions, ointments, liquids or semi-liquids including solutions or suspensions, or incorporated into patches, bandages, or any type of wound dressings.

A composition comprising a chimeric enzyme of the invention may also be lyophilized using means well known in the art, e.g., for subsequent reconstitution and use according to the invention.

Also of interest are formulations for liposomal delivery, and formulations comprising microencapsulated enzymes, including sugar crystals. Compositions comprising such excipients are formulated by well-known conventional methods (see, e.g., *Remington's Pharmaceutical Sciences*, Chapter 43, 14th Ed., Mack Publishing Col, Easton PA 18042, USA).

In general, pharmaceutical compositions can be prepared in various forms, such as granules, tablets, pills, suppositories, capsules (e.g., adapted for oral delivery), microbeads, microspheres, liposomes, suspensions, salves, lotions, and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Formulations may incorporate stabilizing agents, wetting and emulsifying agents, salts for varying the osmotic pressure or buffers for securing an adequate pH value.

VI. Kits

The invention also provides kits for selectively suppressing the growth of certain targeted bacterial species, especially in the presence of other non-targeted bacterial species that might be closely related to the targeted bacterial species (e.g., belonging to the same genus) according to the method of the present invention. The kits typically include a first container that contains a composition including an effective amount of a polypeptide of interest, e.g., one in Table 3 such as one comprising or consisting essentially of an amino acid sequence selected from SEQ ID NOs:7, 33, 45, 47, 51, 57, 59, 61, 65, 67, 69, 71, 73, and 75. The polypeptide is typically present in a composition formulated for systemic delivery, for example, in the form of a solution (e.g., aqueous solution) or dispersion suitable for injection by intravenous, intramuscular, or subcutaneous means or in the form of a pill, tablet, caplet, or capsule suitable for oral ingestion, or for direct delivery via respiratory system, for example, in the form of a spray or aerosolized mist suitable for inhalation into the respiratory airway, or for local delivery, for example, in the form of a cream, paste, lotion, ointment, spray and the like suitable for topical application to a surface such as skin, or being incorporated into a skin patch, a bandage, or wound dressing for use on a patient's skin.

Optionally, the kit may further include informational material such as instructions for a user on how to use the kit for suppressing the growth of certain targeted bacterial species.

EXAMPLES

The following examples are provided by way of illustration only and not by way of limitation. Those of skill in the art will readily recognize a variety of non-critical parameters that could be changed or modified to yield essentially the same or similar results.

Introduction

Bacteriocins are protein antibacterials produced by bacteria to kill similar or closely related species, as a survival mechanism in competing ecological niches. Bacteriocins parasitize on components of bacterial machinery involved in transport of essential nutrients and minerals such as iron and vitamin B12 for cell entry. Bacteriocin-producing bacteria are themselves protected from lethal activity by the presence of immunity proteins that bind to the bacteriocin and sterically prevent its activity. Bacteriocins are be highly genus specific and target the same genus as the producer organism. Large bacteriocins (>30 kDa) are modular proteins and many of them are natural chimeric proteins, evolved from varied sources having receptor binding, translocation and killing domain, functioning as a single unit to kill susceptible bacteria (FIG. 1). Using the receptor binding and translocation domains, bacteriocins enter bacterial cells by parasitizing on cell-surface receptors Bacteriocins after binding to their cognate receptors at the cell surface and are transported through the outer membrane of susceptible bacteria by using either the Tol system (Group A) or the Ton system (Group B). After entry into the cell, the killing domain can effect bactericidal action, through multiple modes such as membrane damage, or by interfering in metabolic pathways, and DNase or RNase activities.

Susceptibility to bacteriocins is primarily driven by the presence of cell surface receptor and translocation proteins expressed by susceptible bacteria, and to a lesser extent by the absence of a cognate immunity protein. Hence most bacteriocins exhibit a narrow coverage. Although bacteria can remain sensitive to a given bacteriocin even when the immunity is present, bacteria lacking its cognate receptor will be completely insensitive to the bacteriocin. Bacteriocins utilize only a single cell surface receptor and a single translocation system for cell entry in to susceptible bacteria. Any mutation(s) in genes involved in either the receptor or translocation machinery will render the bacteria resistant to bacteriocins adding to the restricted coverage. Under laboratory conditions, many bacteriocins studied so far demonstrate an in vitro frequency of resistance (FoR) of $10^{-6}$ to $10^{-7}$. Due to the dual reason of narrow coverage and higher FoR, bacteriocins were not previously considered as a therapeutic option for treating bacterial infections.

Bacteriocins of *Klebsiella* spp.: Klebicins

*Klebsiella pneumoniae* is a highly drug-resistant pathogenic bacteria. In humans, it causes serious infections including pneumonia, bacteremia and urinary tract infections. Due to high burden of antimicrobial resistance, new interventions are required for treatment of infections caused by these bacteria.

Klebicins are large molecular weight bacteriocins produced by *Klebsiella* spp. and specifically kill other susceptible members of the *Klebsiella* genus including the pathogenic *Klebsiella pneumoniae* with possible utility as a therapeutic option. However, as known for other bacteriocins, klebicins also have properties such as narrow coverage within the *Klebsiella* and high FoR. Since the clinical utility of klebicins are yet to be explored, pre-existing resistance may be very minimal and emergence of resistance will be only limited to the susceptible bacteria.

Improving Properties of Klebicins

1. Cocktails

The properties of narrow coverage, FoR could be overcome using a combination of klebicins that recognize different cell surface receptors, different mechanism of action (MoA) and contain both group A and B klebicins as individual components in the cocktail. This will enhance the utility of klebicins as therapeutic entities. Klebicins and their receptor (RD), translocation (TD) and killing domains (KD) are listed in Table 1.

TABLE 1

Natural klebicins

| Protein ID | Homolog of Klebicin Type | Receptor | Mechanism of Translocation | Mechanism of cytotoxicity | Mw/PI |
|---|---|---|---|---|---|
| P611 | Klebicin B | Not known | Not known | Dnase | 79.6/8.96 |
| P628 | Klebicin CCL | IutA | Tol | Rnase | 59.2/9.21 |
| P764 | KpneA | OmpC | Ton | Pore forming | 39.8/8.96 |
| P774 | KpneM | FhuA | Ton | Peptidoglycan synthesis inhibitor | 30.2/5.57 |
| P801 | KvarM | FhuA | Ton | Peptidoglycan synthesis inhibitor | 29.8/8.9 |

The FoR of these klebicins were studied by plating high concentrations ($>10^9$ cells) of *K. pneumoniae* strain ATCC 13383 on agar plates containing 8×MIC concentrations of individual and combinations containing two klebicins. Colonies that were recovered from these plates were enumerated to determine the recovery frequency which will correspond to the highest possible FoR (Table 2). With single klebicins, the FoR was in the range of $10^{-6}$ to $10^{-7}$ indicating possible emergence of resistance during therapy. However, when the plating was done on a combination of two klebicins, all combinations except P774 and P801 reduced FoR to $<10^{-9}$ demonstrating that the appropriate klebicin combinations can mitigate emergence of resistance. The combination of P774 and P801 did not reduce FoR possibly due to the identical MoA—both P774 and P801 recognize the same cell surface receptor and utilize TonB pathway for translocation. Hence, combination of klebicins with different MoA in a cocktail will aid in mitigating the FoR.

TABLE 2

Frequency of resistance (FoR) of natural klebicins individually and in combinations

| Klebicins and combinations @ 8X | Recovery Frequency |
|---|---|
| P628 | ~$1 \times 10^{-7}$ |
| P764 | ~$1 \times 10^{-7}$ |
| P774 | ~$1 \times 10^{-6}$ |
| P801 | ~$5 \times 10^{-7}$ |
| P628 + P764 | $<10^{-9}$ |
| P628 + P774 | $<10^{-9}$ |
| P774 + P764 | $<10^{-9}$ |
| P801+ P628 | $<10^{-9}$ |
| P801 + P764 | $<10^{-9}$ |
| P801 + P774 | ~$5 \times 10^{-7}$ |

Although the combination approach will not only help mitigate the resistance problem but also improve overall coverage of klebicins, there are few limitations for a cocktail approach. This includes increased cost of goods due to production and processing of multiple proteins, finding compatible storage buffers and conditions, challenges in formulation and establishing quality control parameters for multiple proteins.

To overcome these challenges, a novel strategy is to combine the properties of multiple klebicins into a single klebicin by protein engineering. This can be achieved by fusing or swapping domains from different klebicins to generate chimeric fusions with desired properties. Klebicins, like other bacteriocins, are multidomain protein structures that have evolved through natural evolution to recognize and kill susceptible bacteria. These are multidomain protein structures that fold into active confirmation and function as a single unit, there is no available information on whether generic protein engineering strategies such as domain swapping or domain additions will yield active proteins. Therefore, the combinations of domains or strategies that would work cannot be predicted a priori.

2. Chimeric Fusions

Chimeric klebicins with properties of combination of multiple klebicins will be generated empirically. The expected outcome is to have chimeric klebicins with improved coverage and FoR, as observed with a combination. Since the coverage of natural bacteriocins are limited by the single cell surface receptor recognition, the chimeric fusion strategy will be to design and engineer klebicins that can recognize multiple cell surface receptors and/or utilize both Tol and Ton pathways for translocation.

Figure 2:
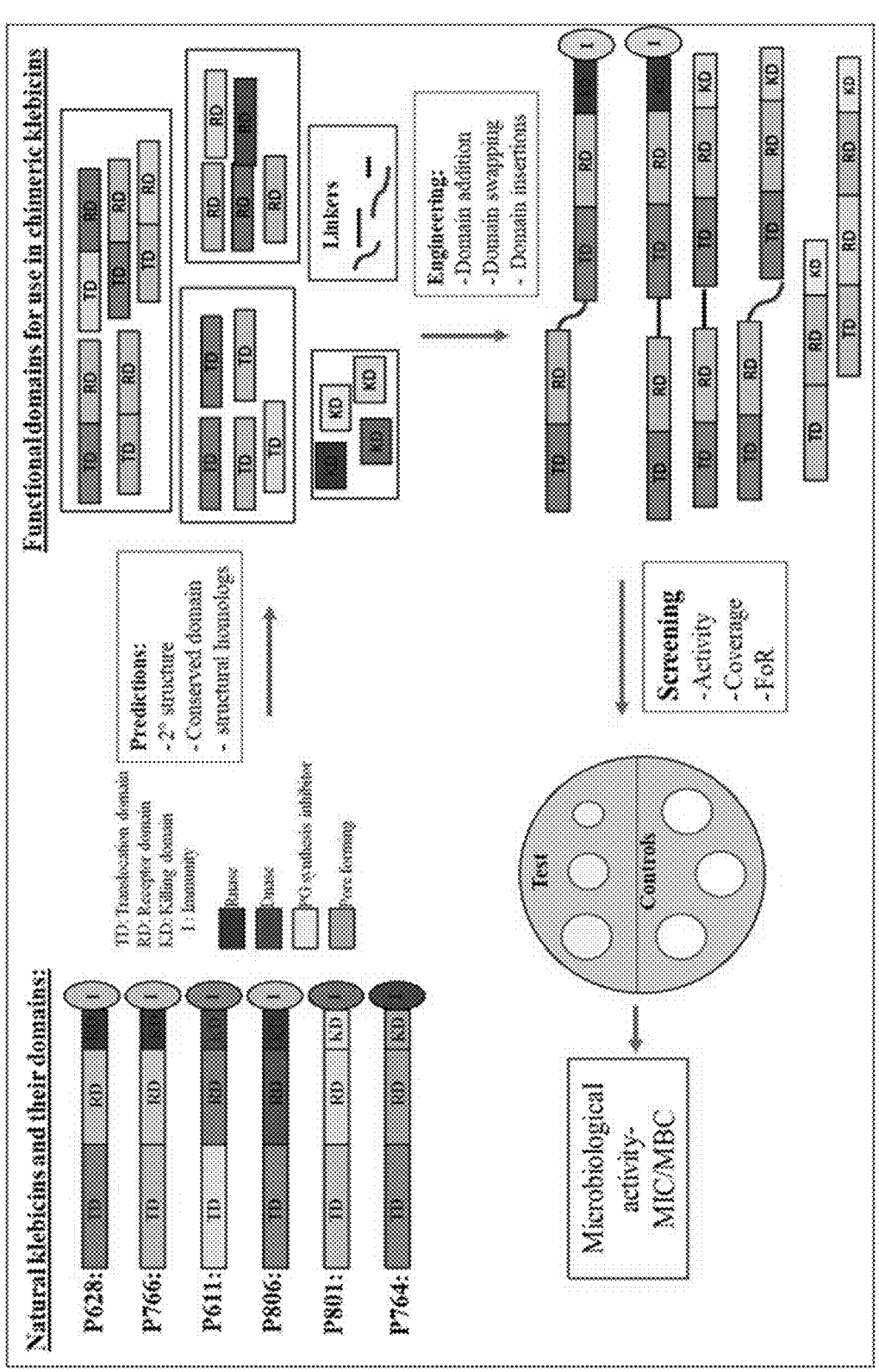
FIG. 2. Workflow for generating chimeric klebicins.

Strategies included adding the translocation domain (TD) and receptor binding domain (RD) of a klebicin, alone or together to another klebicin, inserting a RD from one klebicin into another klebicin to generate a twin RD, replacing the RD or KD of one klebicin with another one and fusing two klebicins together to make a single protein. Chimeric fusion workflow is depicted in FIG. 2.

Several chimeric klebicins were generated with domains from different klebicins fused together. Some of the chimeric fusions were active and showed antibacterial activity on a lawn of *K. pneumoniae* strain ATCC13883 (Table 3).

TABLE 3

Engineered klebicins generated by domain shuffling/domain
additions; FL: Full Length, TD:
Translocation domain, RD: Receptor
binding domain, KD: Killing domain, CD: Catalytic domain

| Sl. | Protein | Domain details | Antibacterial activity on *K. pneumoniae* |
|---|---|---|---|
| 1 | P771 | P764 TD RD + P628 FL | Yes |
| 2 | P772 | P764 TD RD-Flexible linker + P628 FL | Yes |
| 3 | P777 | P764 TD RD-Rigid linker + P628 FL | Yes |
| 4 | P775 | P628 TD RD-Rigid linker + P764 FL | Yes |
| 5 | P776 | P628 TD RD-Flexible linker + P764 FL | Yes |
| 6 | P780 | P774 TD RD-Rigid linker + P628 FL | Yes |
| 7 | P781 | P628 TD RD-Flexible linker + P774 FL | No |
| 8 | P782 | P774 TD RD-Flexible linker + P628 FL | Yes |
| 9 | P784 | P628 TD RD-Rigid linker + P774 FL | No |
| 10 | P787 | P764 TD RD-Flexible linker + P774 FL | No |
| 11 | P789 | P764 TD RD-Rigid linker + P774 FL | No |
| 12 | P788 | P764 TD -Rigid linker + P628 FL | Yes |
| 13 | P792 | P764-Rigid Linker + P774 FL | Yes |
| 14 | P795 | P764-Flexible Linker + P774 FL | Yes |
| 15 | P805 | P628 Δ7 | Yes |
| 16 | P806 | P628 Δ25 | Yes |
| 17 | P810 | P764 TD RD-P774 RD-P764 KD (Twin RD) | Yes |
| 18 | P812 | P628 TD RD-Rigid Linker-P764 KD | Yes |
| 19 | P818 | P764 TD-P774 RD + P764 KD | No |
| 20 | P819 | P774 TD-P764 RD + P774 KD | No |
| 21 | P820 | P764 TD RD-Rigid Linker-P628 Δ25 | Yes |
| 22 | P822 | P801 TD RD-Rigid Linker + P764 KD | No |
| 23 | P821 | P628 TD RD-Rigid Linker + P801 FL | Yes |
| 24 | P823 | P628 TD RD-Flexible Linker + P801 FL | Yes |
| 25 | P835 | P628 TD RD + P801 FL | Yes |
| 26 | P836 | P628 TD RD-4X Rigid Linker + P801 FL | Yes |
| 27 | P837 | P628 TD RD-2X Flexible Linker + P801 FL | Yes |
| 28 | P842 | P628 FL + P801 FL | Yes |
| 29 | P845 | P628 FL-Flexible Linker + P801 FL | Yes |
| 30 | P862 | P628 FL-Rigid Linker + P801 FL | Yes |
| 31 | P863 | P764 FL-Rigid Linker + P801 FL | Yes |
| 32 | P864 | P764 FL-Flexible Linker + P801 FL | Yes |
| 33 | P870 | P764 FL-4X Rigid Linker + P801 FL | Yes |
| 34 | P867 | 1-53 amino acids of P849 (P801 homolog from *K. quasipneumoniae*) replaced with 1-22 amino acids of P801 | Yes |
| 35 | P875 | P801-Rigid Linker + GP36CD | Yes |
| 36 | P889 | P764-GP36CD | Yes |
| 37 | P891 | P764-Flexible Linker + GP36CD | Yes |
| 38 | P892 | P764-TDRD-Rigid Linker + GP36 CD | Yes |

Note:
Constructs #1, 2, 3, 6, 8, 12, 15 and 16 listed in Table 3 are expressed along with the immunity protein of P628.

31 of 38 engineered klebicins demonstrated antibacterial activity proving that protein engineering strategies can be applied to generate active chimeric klebicins. It is also noticeable that a few of the chimeric molecules lost activity, indicating that not all engineered klebicins retain activity.

Example 1: P775 (P628 TD RD-Rigid Linker+P764 FL)

Figure 3A:
FIGS. 3A-3D. Details of P775 with domain architecture (FIG. 3A), protein expression profile (FIG. 3B), purified protein profile (FIG. 3C) and activity on *K. pneumoniae* ATCC13883 by lawn inhibition assay (FIG. 3D).
Figure 3B:
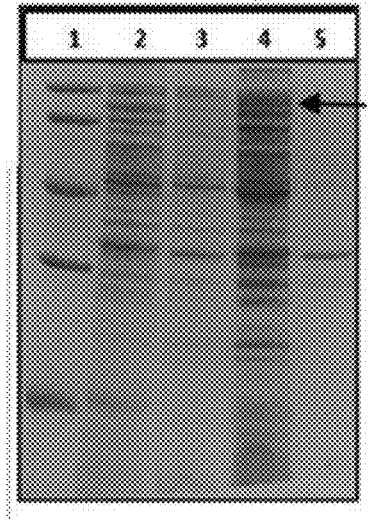
Figure 3C:
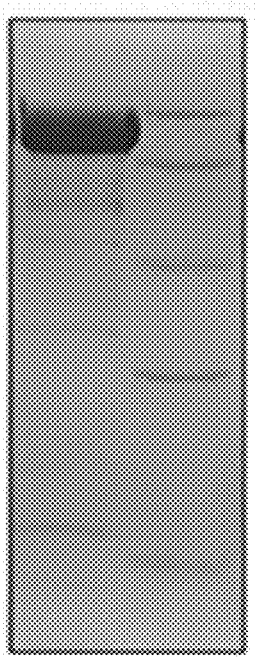
Figure 3D:
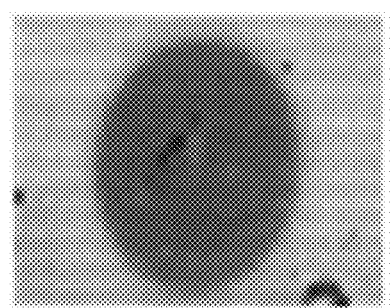

P775 was generated by fusing the TD and RD region of P628 with full length (FL) P764 with the aid of a rigid linker. This construct will have two translocation and receptor binding units that can recognize two different cell surface receptors and translocation machinery. P628 TD RD region and P764 were PCR amplified separately and fused together by synthesis by overlap extension (SOE) PCR (FIG. 3A). The fusion gene was cloned into pET26b expression vector, sequence confirmed and protein expression done in *E. coli* expression strain ER2566 (FIG. 3B). The expressed protein was purified by a two-step ion-exchange chromatography to obtain ~90% homogenous protein (FIG. 3C) and 2-5 µg of the purified protein was active on *K. pneumoniae* ATCC13883 lawn (FIG. 3D). The MIC of P775 was 5 µg/mL on ATCC13883 in iron-deficient Cas amino acids growth media.

Figure 4:
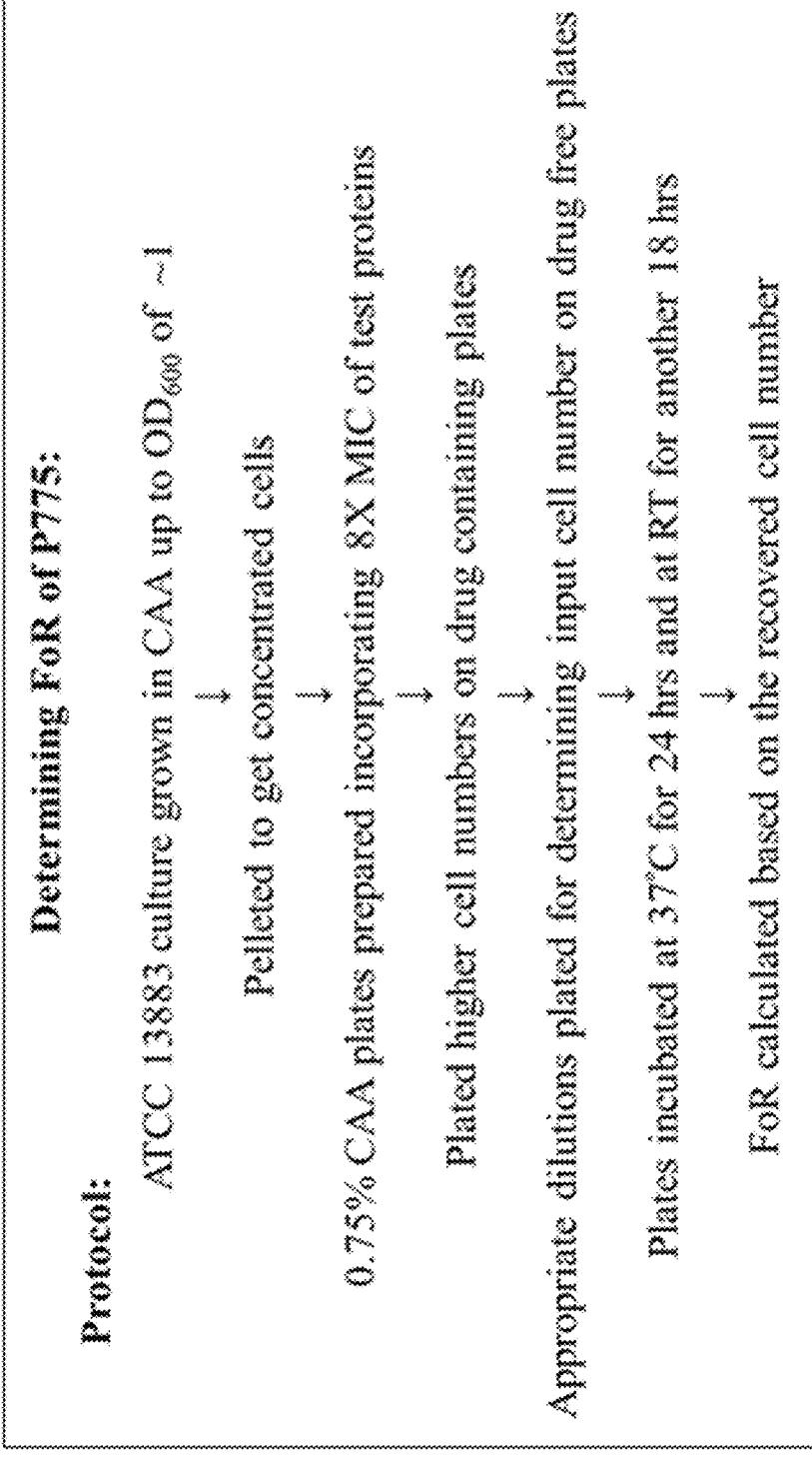
FIG. 4. Protocol for Frequency of Resistance (FoR) studies of klebicins.

Since P775 harbours the TD and RD of two different klebicins and yet retains activity, P775 may demonstrate properties of both proteins. This was determined by FoR studies as described in FIG. 4.

While the FoR of P628 and P764 were in the expected range of about $10^{-7}$, the FoR of P775 was much lower at $3 \times 10^{-10}$ (Table 4).

TABLE 4

FoR of natural klebicins P628, P764 and chimeric klebicin P775

| Proteins | Recovery Frequency |
|---|---|
| P628 | ~6.4 × $10^{-7}$ |
| P764 | ~1 × $10^{-7}$ |
| P775 | 3.1 × $10^{-10}$ |

These results indicate: (1) FoR of P775 is ~$10^{-10}$, which is significantly lesser than individual klebicins P628 and P764. This could be attributed to the combination of properties of both P628 and P764. (2) P775 behaves like a combination of two klebicins in reducing the FoR.

Activity of P775 on P628 Resistant Mutants of ATCC13883

Since P775 demonstrated properties of both P628 and P764 by FoR studies, the activity of P775 was determined on P628 resistant mutants.

Spontaneous mutants of ATCC13883 that are resistant to klebicin P628 were isolated previously by plating high cell numbers of this strain on P628 embedded agar plates. These mutants were confirmed as P628 resistant by MIC studies. Two of the P628-resistant mutants of ATCC13883 strain, P628R 32.1 and P628R 32.3 were selected for testing activity of P775 along with their wild-type (WT) strain. Lawn inhibition assay and MIC were done for this. Lawn inhibition was done by placing 10 µg of P775 (FIG. 5A) and an MIC was done according to the CLSI protocol with test growth media casamino acids (CAA) (FIG. 5B).

These results indicate that P775 possesses antibacterial activity on P628-resistant mutants of ATCC13883. Taken together, the FoR studies and activity on P628-resistant mutants, P775 exhibits properties of two klebicins.

Example 2: P810 (P764 TD RD-P774 RD-P764 KD)

Another strategy is to engineer klebicins to bind to multiple cell surface receptors that can eventually aid in improved coverage as well as reduce FoR. A klebicin with two receptor-binding domains, which bind to two different cell surface receptors, was designed with P764 as the backbone molecule incorporating the receptor binding domain of P774. For this, DNA sequence of the receptor binding domain from klebicin P774 was PCR amplified and cloned into P764, downstream of its own receptor binding region. The fusion protein, termed P810, was expressed in *E. coli* protein expression strain ER2566 (FIG. 6) and the protein of ~50 kDa was expressed in the soluble fraction of the cell and was also found be active on *K. pneumoniae* strain ATCC13883 by a lawn inhibition assay.

These results indicate that P810 is active on *K. pneumoniae*.

Example 3: P821 (P628 TD RD-Rigid Linker+P801 FL)

P821 was generated by fusing the TD and RD region of P628 with full length (FL) P801 with the aid of a rigid linker. This construct will have two translocation and receptor binding units that can recognize two different cell surface receptors and translocation machinery. P628 TD RD region and P801 were PCR amplified separately and fused together by synthesis by overlap extension (SOE) PCR. The fusion protein, termed P810, was expressed in *E. coli* protein expression strain ER2566 (FIG. 7) and the protein of ~78 kDa was expressed in the soluble fraction of the cell and was also found be active on *K. pneumoniae* strain ATCC13883 by a lawn inhibition assay.

These results indicate that P821 is active on *K. pneumoniae*.

MIC and Bactericidal Activity of P821

The MIC of P821 was determined according to a modified CLSI protocol in growth media, casamino acid media (CAA) and fetal calf serum (FCS). In CAA the MIC was 6 μg/mL and in FCS it was 12 μg/mL, demonstrating the activity of P821 in both growth media and in the presence of serum.

Figure 8A:
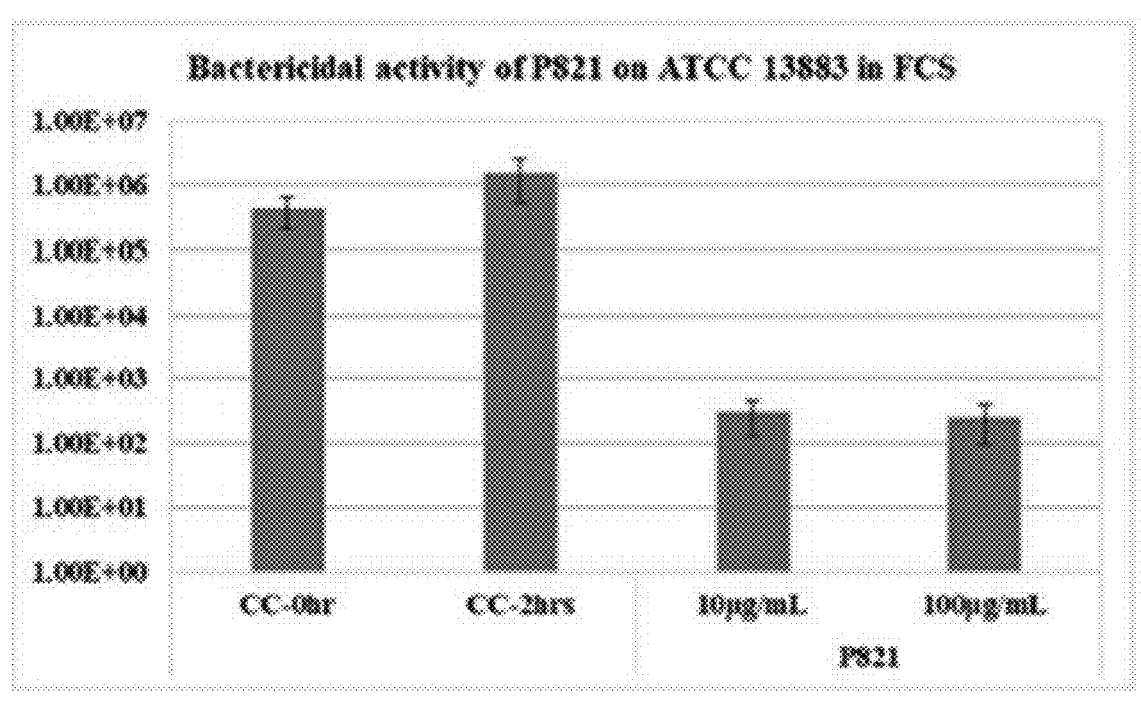
FIGS. 8A-8B. Bactericidal activity of P821 on *K. pneumoniae* strains ATCC13883 (FIG. 8A) and B2101 (FIG. 8B).
Figure 8B:
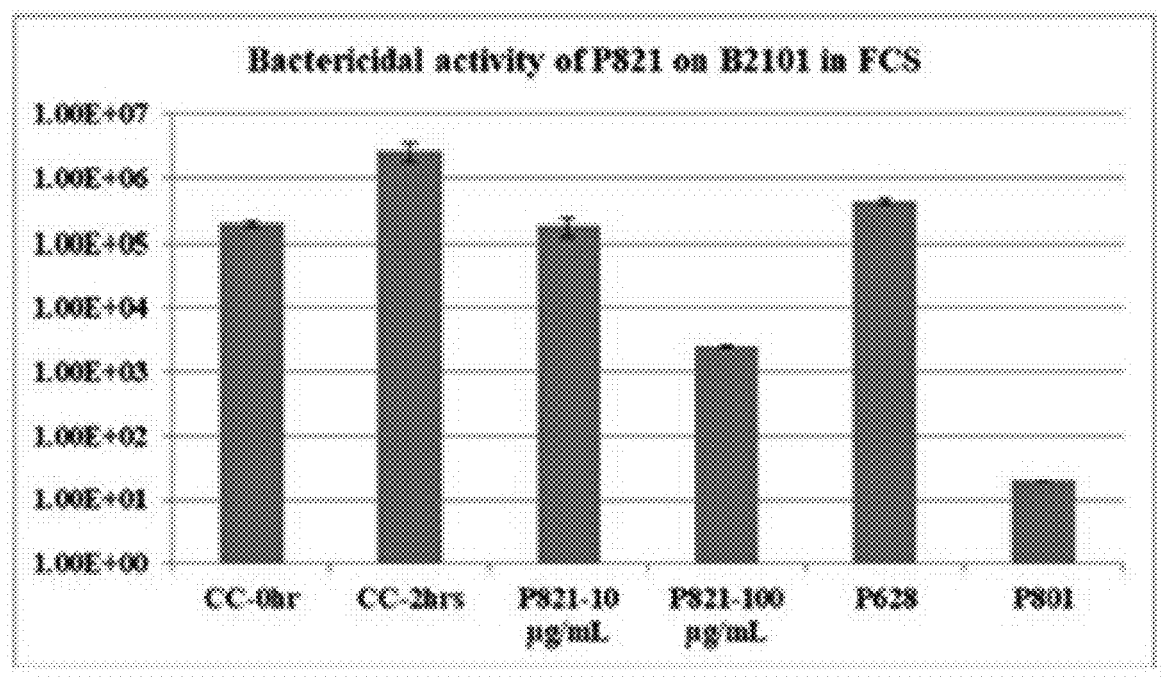

Since P821 is a chimeric fusion of two different klebicins, P628 and P801, to determine whether the fusion has properties of both proteins, the bactericidal activity of P821 was determined on different strains of *K. pneumoniae* with different sensitivity patterns. ATCC13883 and B2101 were chosen for the first set of experiments. While the strain ATCC13883 is sensitive to both P628 and P801, the strain B2101 is sensitive to only P801. Bactericidal activity was determined by a cell killing assay where in ~$10^6$ CFU/mL of both ATCC13883 and B2101 were treated with 10 and 100 μg/mL of P821 in a volume of 200 μL at 37° C. for 2 h and the remaining number of cells were determined by plating out appropriate dilutions and incubating the plates at 37° C. for 18 h. The bactericidal activity of P628 and P801 on B2101 was determined in the same experiment. 100 μg/mL of both P628 and P801 were used. The results indicate that P821 brought about >3 log reduction in CFU with ATCC13883 even with 10 μg/mL of the purified protein (FIG. 8A). With B2101, ~2 log CFU reduction was obtained with 100 μg/mL of P821. While 100 μg/mL of P628 did not kill B2101, >3 log CFU reduction was obtained with 100 μg/mL of P801 (FIG. 8B). P821 killed *K. pneumoniae* strains and the activity was similar to P801.

When a similar experiment was conducted with P628 sensitive-P801 insensitive isolate-B2265, no killing was observed suggesting that the protein did not exhibit P628 activity.

Example 4: P823 (P628 TD RD-Flexible Linker+P801 FL)

Figure 9A:
FIGS. 9A-9C. Details of P823 with domain architecture (FIG. 9A), protein expression profile (FIG. 9B) and activity on *K. pneumoniae* ATCC13883 by lawn inhibition assay (FIG. 9C).
Figure 9B:
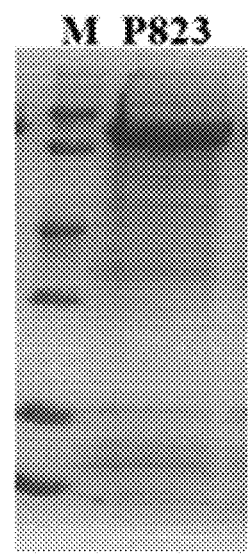
Figure 9C:
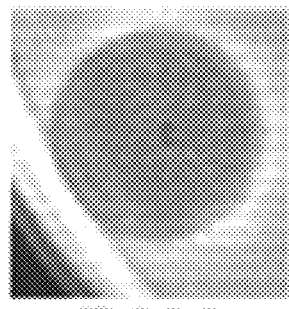

P823 was generated by fusing the TD and RD region of P628 with full length (FL) P801 with the aid of a flexible linker. This construct will have two translocation and receptor binding units that can recognize two different cell surface receptors and translocation machinery. P628 TD RD region and P801 were PCR amplified separately and fused together by synthesis by overlap extension (SOE) PCR. This fusion protein was expressed in *E. coli* protein expression strain ER2566 (FIG. 9) and the protein of ~78 kDa was expressed in the soluble fraction of the cell and was also found be active on *K. pneumoniae* strain ATCC13883 by a lawn inhibition assay.

These results indicate that P823 is active on *K. pneumoniae*.

Example 5: P835 (P628 TD RD+P801 FL); P836 (P628 TD RD-4× Rigid Linker+P801 FL); P837 (P628 TD RD-2× Flexible Linker+P801 FL)

Figures 10A, 10B:
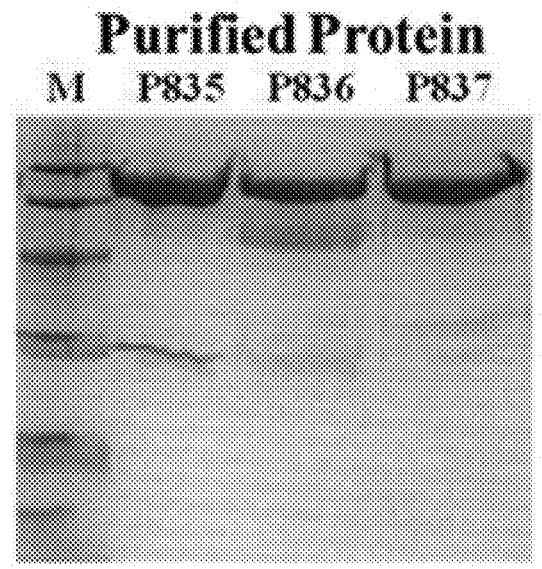
FIGS. 10A-10D. Details of P835, P836, and P837 with domain architecture (FIG. 10A), purified protein profile (FIG. 10B) and activity on *K. pneumoniae* ATCC13883 by lawn inhibition assay (FIG. 10C). Bactericidal activity of P836 by CFU drop assay (FIG. 10D)

P835, P836, and P837 were generated by fusing the P628TDRD to the N-terminus of Full length P801 without a linker, with a 4× rigid linker, and with a 2× Flexible linker in between, respectively. These constructs have two translocation and receptor binding units that can recognize two different cell surface receptors and translocation machinery. P628 TD RD region and P801 were PCR amplified separately using appropriate primers with the linkers and fused together by synthesis by overlap extension (SOE) PCR (FIG. 10A). The proteins were expressed in *E. coli* and purified using ion exchange chromatography (FIG. 10B). Purified proteins were then taken forward for testing.

Figure 10C:
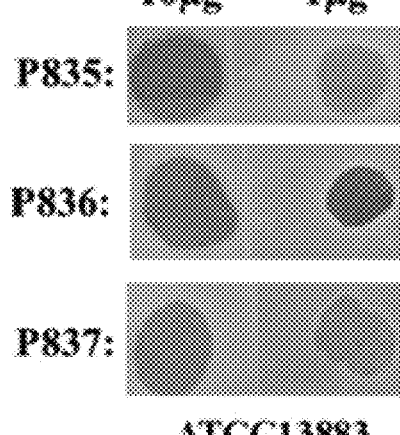
Figure 10D:
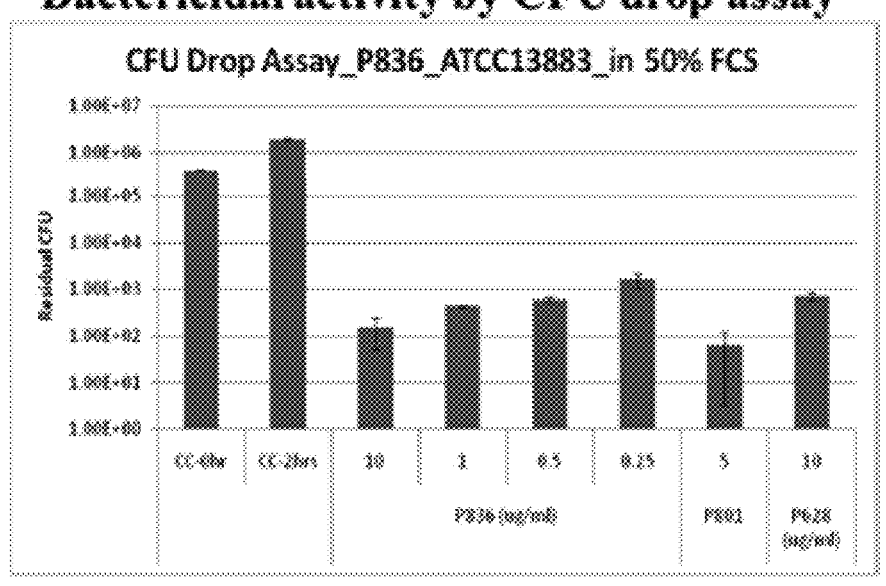

10 μg and 1 μg of the purified proteins were placed on lawns of *Klebsiella* isolates. The plates were incubated at 30° C. for 16-18 hrs. The fusion proteins showed inhibition zone on the bacterial lawn indicating the fusion was active (FIG. 10C). P836 was active in physiologically relevant condition like serum and exhibited a rapid killing even with in a 2 hrs CFU drop assay (FIG. 10D).

Example 6: P845 (P628 FL-Flexible Linker+P801 FL); P862 (P628 FL-Rigid Linker+P801 FL)

Figure 11A:
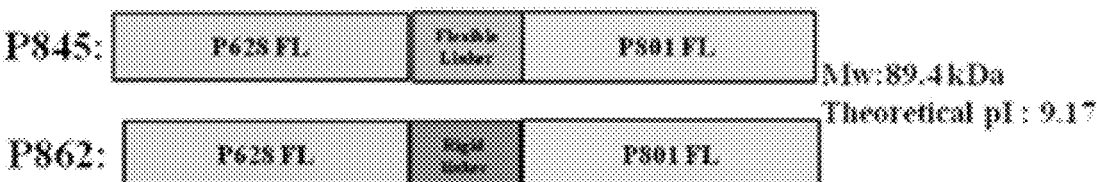
FIGS. 11A-11D. Details of P845 and P862 with domain architecture (FIG. 11A), purified protein profile (FIG. 11B) and activity on *K. pneumoniae* ATCC13883 by lawn inhibition assay (FIG. 11C). Assessment of hybrid activity (FIG. 11D).
Figure 11B:
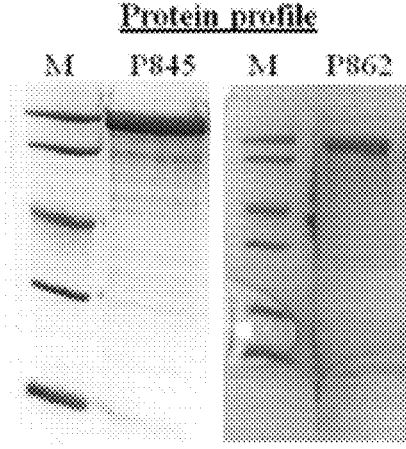

P845 and P862 were generated by fusing the P628 full length to the N-terminus of Full length P801 with a flexible and rigid linker in between respectively (FIG. 11A). P845 and P862 were expressed in *E. coli* and purified using ion exchange chromatography (FIG. 11B). Purified proteins were then taken forward for testing and compared against P836 to check if there is any improvement in the activity or coverage by extending P628 to full length in P836.

Figure 11C:

P845 and P862 were tested by lawn inhibition assay. 20 μg of the purified P845 and P862 were placed on lawns of *Klebsiella* isolates. The plates were incubated at 30° C. for 16-18 hrs. P845 and P862 showed inhibition zone on the bacterial lawn indicating the fusions were active (FIG. 11C).

MICs of P836, P845 and P862 were tested in CAA and 10% FCS against ATCC13883, P845 and P862 gave improved MIC in CAA as compared to P836 and is active even in the presence of serum (Table 5).

TABLE 5

| MICs of P836, P845 and P862 in CAA and 10% FCS on strain ATCC13883 | | |
| --- | --- | --- |
| Protein | CAA(μg/ml) | CAA+ 10% FCS(μg/ml) |
| P836 | >256 | 4-8 |
| P845 | 4-8 | 4-8 |
| P862 | 4-8 | 4-8 |

Figure 11D:
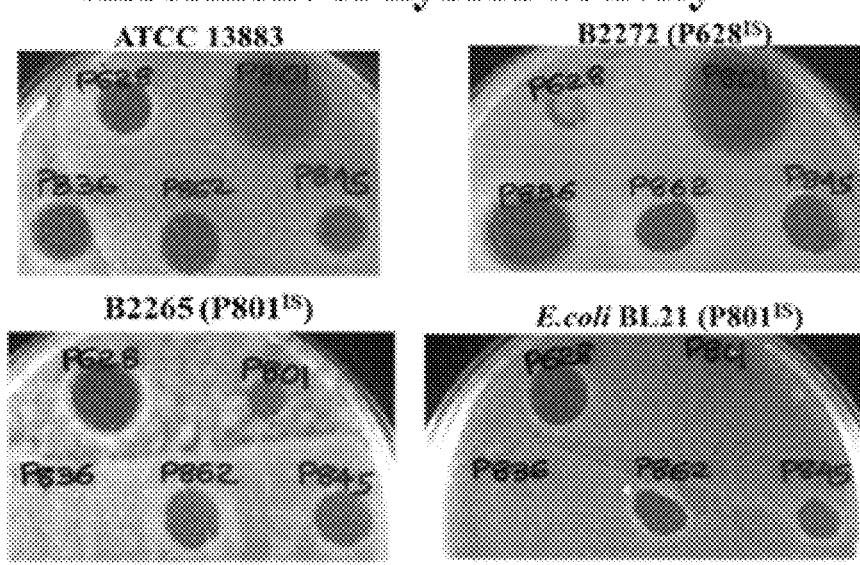

The hybrid properties of chimeras were assessed by testing the lawn inhibition activity on P801 insensitive-P628 sensitive isolates and P801 sensitive-P628 insensitive isolates (S-sensitive and IS-insensitive). The isolates chosen were ATCC13883 (Reference standard), B2272 (P801$^S$-P628$^{IS}$), B2265 (P801$^{IS}$-P628$^S$). Additionally, *E. coli* was also included for testing since only P628 is active on it. P836 behaved like P801, exhibiting activity only on P801 sensitive isolates and not on P801$^{IS}$-P628$^{S}$. However, P845 and P862 were active on both P801$^{S}$-P628$^{IS}$ and P628 P801$^{IS}$-P628$^{S}$ isolates and on *E. coli* also, indicating that these chimeras harbor properties of both P628 and P801 in a single molecule resulting in improved coverage over the individual klebicins alone (FIG. 11D).

Example 7: P863 (P764 FL-Rigid Linker+P801 FL)

Figure 12A:
FIGS. 12A-12C. Details of P863 with domain architecture (FIG. 12A), purified protein profile (FIG. 12B) lawn inhibition assay and assessment of hybrid activity (FIG. 12C).
Figure 12B:
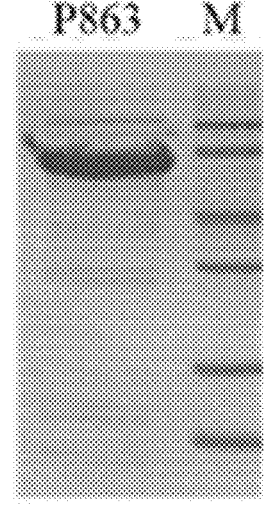
Figure 12C:
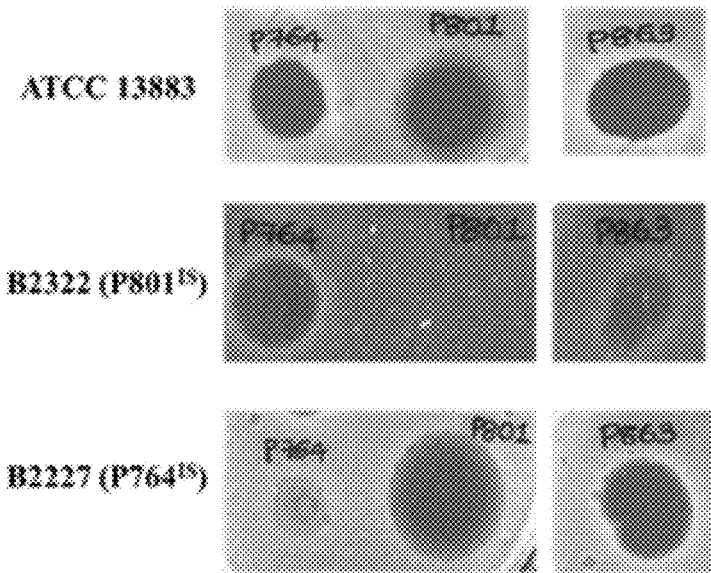

P863 was generated by fusing the P764 full length to the Full length of P801 with a 2× rigid linker in between (FIG. 12A). P863 was expressed in *E. coli* and purified using ion exchange chromatography (FIG. 12B). Purified protein was then taken forward for testing. 20 μg of the purified P863 was placed on lawns of *Klebsiella* isolates and the plates were incubated at 30° C. for 16-18 hrs. P863 was active by lawn inhibition assay on strains that were sensitive to P764 but insensitive to P801 and also on strains that were insensitive to P764 and sensitive to P801, indicating that P863 possesses hybrid properties of both P764 and P801 in a single molecule (FIG. 12C). P863 was active even in the presence of serum and gave MIC of 4 μg/ml in CAA and 1 μg/ml with 10% FCS (Fetal Calf Serum) on ATCC 13883.

Example 8: P867 (Engineered to Improve Potency)

Figures 13A, 13B:
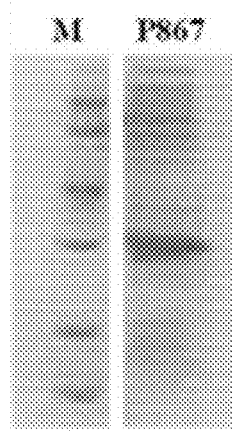
FIGS. 13A-13C. Details of P867 with domain architecture (FIG. 13A), purified protein profile (FIG. 13B). Activity by lawn inhibition assay (FIG. 13C).
Figure 13C:
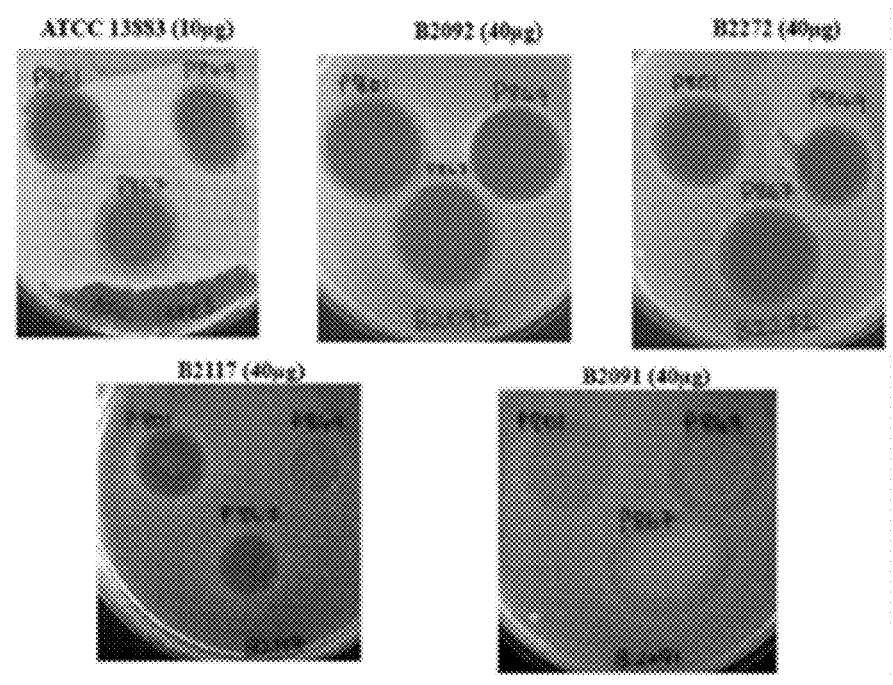

P867 was generated by replacing the first 53 amino acids of P849 (P801 homolog that gave no MIC in CAA) with the first 1-22 amino acids (consisting of TonB motif) of P801 (FIG. 13A). P867 was expressed in *E. coli* and purified using ion exchange chromatography (FIG. 13B). Purified protein was then taken forward for testing. P867 was placed on lawns of *Klebsiella* isolates and the plates were incubated at 30° C. for 16-18 hrs. P867 was active on the tested P801 sensitive isolates (FIG. 13C). P867 was found to be potent in MIC studies suggesting that the engineering of P849 by introduction of P801 TonB motif has enhanced the activity (Table 6). Activity of P867 was retained in different serum matrices with MIC of 0.5 and 0.07 μg/ml in 50% FCS and 50% human serum respectively on *K. pneumoniae* strain ATCC13883.

TABLE 6

| MIC (μg/mL) in CAA on *K. pneumoniae* | | |
| --- | --- | --- |
| Proteins | ATCC13883 | B2092 |
| P801 | 1 | 1 |
| P849 | >256 | >256 |
| P867 | 1 | 0.25 |

Example 9: P870 (P764FL-4× Rigid Linker+P801FL)

Figure 14A:
FIGS. 14A-14C. Details of P870 with domain architecture (FIG. 14A), purified protein profile (FIG. 14B). Activity by lawn inhibition assay (FIG. 14C).
Figure 14B:
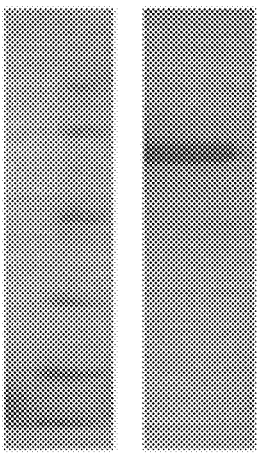
Figure 14C:
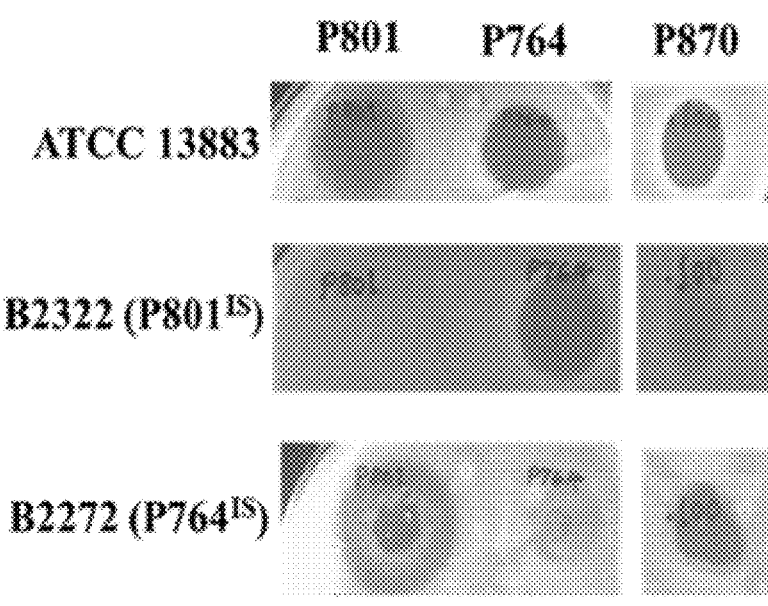

P870 was generated by fusing the P764 full length to the N-terminus of Full length of P801 with a 4× rigid linker in between (FIG. 14A). P870 was expressed in *E. coli* and was purified using ion exchange chromatography to greater than 90% homogeneity (FIG. 14B). Purified protein was then taken forward for testing. 20 μg of purified P870 was placed on lawns of *Klebsiella pneumoniae* isolates and the plates were incubated at 30° C. for 16-18 hrs. P870 was active by lawn inhibition assay and the spot clearance was observed on both P764$^{IS}$ and P801$^{IS}$ suggesting hybrid activity of protein (FIG. 14C). The activity was retained in the presence of sera (Table 7).

TABLE 7

| MICs of P870 | | |
| --- | --- | --- |
| MIC (μg/mL) of P870 | | |
| Strains | CAA | 10% FCS |
| ATCC13883 | >128 | 1 |
| B2221 | 8 | 16 |
| B2281 | 32 | 32 |

Example 10: P875 (P801FL-Rigid Linker+GP36 CD)

Figure 15A:
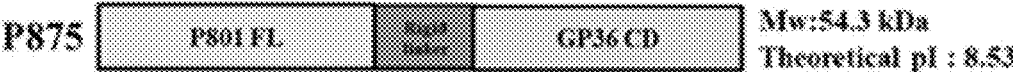
FIGS. 15A-15C. Details of P875 with domain architecture (FIG. 15A), purified protein profile (FIG. 15B). Activity by lawn inhibition assay (FIG. 15C).
Figure 15B:
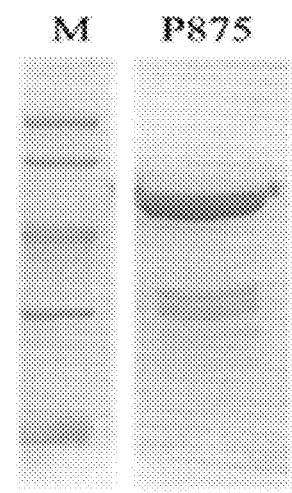
Figure 15C:
Figure 15C:
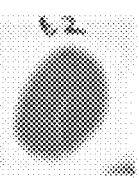

P875 was generated by fusing the GP36 CD (P200), the catalytic domain of the structural lysozyme from *P. aeruginosa* phage P134 to the C-terminus of Full length P801 (FIG. 15A). GP36 CD has muralytic activity and degrades Gram-negative peptidoglycan only when the cells are devoid of outer membrane. P875 was expressed in *E. coli* and was purified using ion exchange chromatography (FIG. 15B). The antimicrobial activity of P875 was evaluated by placing 40 μg of the purified P875 on lawns of *Klebsiella pneumoniae* strains and incubating at 30° C. for 16-18 hrs. P875 showed inhibition zone on the bacterial lawn indicating the fusion was active (FIG. 15C). P875 was highly potent in the presence of 10% FCS and was active on a number of clinical isolates of *Klebsiella pneumoniae* (KP) (Table 8).

TABLE 8

| MIC of P875 on ATCC 13883 and clinical isolates | | |
| --- | --- | --- |
| Sl. No. | KP isolates | MIC (μg/mL) in 10% FCS |
| 1 | ATCC13883 | 0.125 |
| 2 | B2091 | >256 |
| 3 | B2101 | 4 |
| 4 | B2104 | 0.5 |
| 5 | B2113 | >256 |
| 6 | B2117 | >256 |
| 7 | B2123 | 8 |
| 8 | B2151 | 32 |
| 9 | B2253 | 4 |
| 10 | B2556 | 2/4 |
| 11 | B2560 | 8 |
| 12 | B2161 | >256 |
| 13 | B2170 | 0.25 |
| 14 | B2208 | 4/8 |
| 15 | B2261 | 8 |
| 16 | NDM1 KL6 | >256 |
| 17 | B2187 | 4 |
| 18 | B2221 | 4/8 |
| 19 | B2245 | 16 |
| 20 | B2267 | 0.5/1 |
| 21 | B2281 | 16 |

Example 11: P889 (P764 FL+GP36 CD); P891 (P764FL-Flexible Linker+GP36 CD); P892 (P764-Rigid Linker+GP36 CD)

P889 was generated by fusing the GP36 CD (P200), the catalytic domain of the structural lysozyme from *P. aerugi-*

Figures 17A, 17B, 17C:
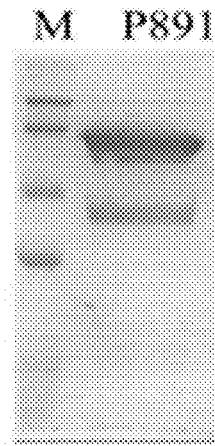
FIGS. 17A-17C. Details of P891 with domain architecture (FIG. 17A), purified protein profile (FIG. 17B). Activity by lawn inhibition assay (FIG. 17C).
Figure 18A:
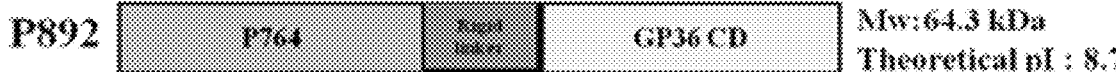
FIGS. 18A-18C. Details of P892 with domain architecture (FIG. 18A), purified protein profile (FIG. 18B). Activity by lawn inhibition assay (FIG. 18C).
Figure 18B:
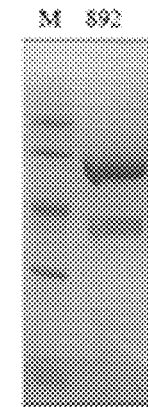
Figure 18C:
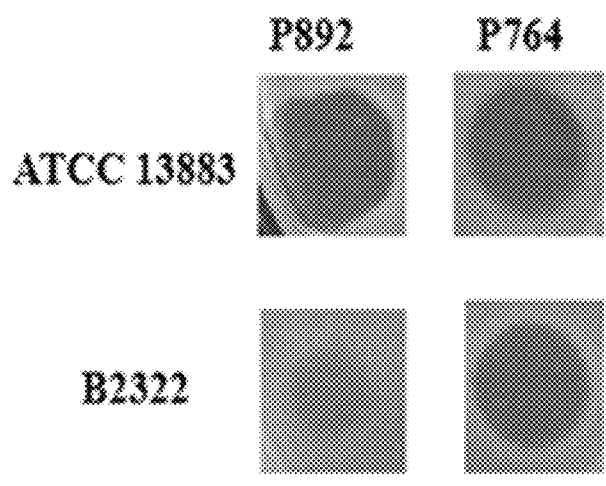

*nosa* phage P134 to the C-terminus of Full length P764. P891 and P892 were generated by fusing the GP36 CD (P200) the catalytic domain of the structural lysozyme from *P. aeruginosa* phage P134 to the C-terminus of Full length P764 with a Flexible linker and a Rigid in between respectively (FIGS. 16A, 17A & 18A). GP36 CD has muralytic activity and degrades Gram-negative peptidoglycan only when the cells are devoid of outer membrane. P889, P891, and P892 were expressed in *E. coli* and were purified by ion exchange chromatography (FIGS. 16B, 17B & 18B). Antimicrobial activity were evaluated by placing 10 μg of purified proteins on the lawns of *Klebsiella pneumoniae* strains and incubating at 30° C. for 16-18 hrs. P889, P891, and P892 showed inhibition zones on the bacterial lawn indicating that the fusion proteins were active (FIG. 16C, 17C, 18C). P889, P891, and P892 showed potent activity by MIC assay on clinical isolates of *Klebsiella pneumoniae* in the presence of FCS (Table 9).

TABLE 9

| MIC of P889, P891, and P892 in 10% FCS against ATCC13883 and clinical isolates | | | |
|---|---|---|---|
| Strains | P889 MIC (μg/mL) | P891 MIC (μg/mL) | P892 MIC(μg/mL) |
| ATCC 13883 | <0.06 | <0.06 | <0.015 |
| B2139 | 1 | 0.5 | 2 |
| B2167 | <0.06 | <0.008 | 0.03 |
| B2236 | 0.25 | 0.015 | 0.06 |

All patents, patent applications, and other publications, including GenBank Accession Numbers, cited in this application are incorporated by reference in the entirety for all purposes.

SEQUENCE LISTING

```
Sequence total quantity: 77
SEQ ID NO: 1              moltype = AA  length = 808
FEATURE                  Location/Qualifiers
source                   1..808
                         mol_type = protein
                         organism = synthetic construct
SEQUENCE: 1
MPEETLTVVG GGNNSCNVSW GGGNGNNGGA GYSGKYGGTS YEGATSMLKL NDRVLIQLYL  60
CNPLNPDYIG APWGSDKDAE SIIRANRDKA GKFKANIQNW KTSGTGSLGS PVVGKSYSSG  120
DVDTYSVSFG KEKYNVLYNR KKDSFTTAYV DGGANKPEHS SGGDGRGPGN SGLGHNGGQA  180
SGNVNGTSGK GGPSSGGGTD PNSGPGWGTT HTPNGDIHNY NPGEFGNGGS KPGGNGGNSG  240
NHSGSSGGGQ SSATAMAFGL PALATPGAEG LALSVSGDAL SAAVADVLAA LKGPFKFGLW  300
GIAIYGVLPS EIAKDDPKMM SKIVTSLPAD TVTETPVSSL PLDQATVSVT KRVADIVKDE  360
RQHIAVVTGR PMSVPVVDAK PTKRPGVFSV SIPGLPSLQV SVPKGVPAAK APPKGIIAEK  420
GDSRPAGFTA GGNSREAVIR FPKESGQKPV YVSVTDVLTP AQVKQRLEEE KRRQQAWDAA  480
HPEEGLKREY DKAKAELDAE DKNIATLNSR IASTEKAIPG ARAAVQEADK KVKEAEANKD  540
DFVTYNPPHE YGSGWQDQVR YLDKDIQNQN EKLKAAQTSL NEMNESLSRD KAALSGAMES  600
RKQKEKKAKD AENKLNEEKK KPRKGTKDYG HDYFPDPKTE DIKGLGELKE GKPKTPKQGG  660
GGKRARWYGD KKRKIYEWDS QHGELEGYRA SDGEHLGAFD PKTGKQVKGP DPKRNIKKYL  720
EVSMGLKLNL TWFDKKTEEF KGGEYSKDFG DDGSVIESLG MPLKDNINNG WFDVEKSWVS  780
ILQPHFKNVI DISKFDYFVS FDYRDGNW                                     808

SEQ ID NO: 2              moltype = DNA  length = 2427
FEATURE                  Location/Qualifiers
source                   1..2427
                         mol_type = other DNA
                         organism = synthetic construct
SEQUENCE: 2
atgcctgaag aaacattgac tgtcgtaggt ggtggtaata acagctgtaa tgttagctgg  60
ggtggtggca atggtaacaa cggtggtgct ggctattctg gtaaatacgg tggtactagc  120
tatgaaggtg caactagtat gttgaagttg aatgaccgtg ttttaattca gctttatctt  180
tgcaatccgc ttaacccaga ttatattgga gcaccttggg gcagtgataa agatgcagaa  240
tcaattatca gagctaacag agataaagca ggaaagttca aggctaatat tcagaactgg  300
aaaacaagcg gtacaggttc tttaggtagc cctgtagttg ggaaatctta tagctcaggt  360
gatgtagata cttattcggt tagcttcgga aaagaaaaat acaatgtcct gtataaccgt  420
aaaaaagact cttttactac agcttatgtc gatggcggcg caaataaacc tgagcatagt  480
ggtggagacg gacgaggtcc gggtaattca ggtctgggac acaatggtgg tcaggccagt  540
gggaatgtga acggtacatc aggtaaaggt ggcccttcat caggtggtgg tacggatcca  600
aacagcgggc cgggctgggg tacgacgcat acacctaacg gggatattca taactataac  660
ccggggggagt ttggtaacgg cgggagtaaa cccggtggta atggcggtaa cagcggcaat  720
catagcggga gctctggtcg cggacagtct tcggccaccg cgatggcctt cggtctgcct  780
gccttggcca ctccgggggc tgaaggactg gctttatccg tttccggcga tgcgttgtcg  840
gccgctgttg ctgatgtgct ggctgccctg aaaggtccgt ttaagtttgg tctgtggggg  900
attgcgattt acggagtgct gccttctgag atagcaaaag atgatccgaa aatgatgtca  960
aaaatcgtga cgtcattgcc ggcagacacg gtaacggaga cgccggtcag ctccctgccg  1020
ctggaccagg cgacggtcag cgtcactaaa cgtgtggcgg atattgtgaa ggacgagcgg  1080
cagcatattg cggttgtcac cggccggcca atgagtgttc ctgtggtgga tgcgaaaccg  1140
acaaaacgtc cgggggtatt cagtgtgtcg attccgggtc tcccgtctct gcaggtgagc  1200
gtacctaaag gtgttccggc cgcgaaagcc ccgcaaaag gcattattgc tgaaaaaggt  1260
gattcacgtc cggctggttt tacggccggt gttaactccc gtgaagccgt tattcgtttc  1320
ccgaaagaga gcggacagaa accggtctat gtgtcggtga cggatgttct tactccggca  1380
caggtaaaac agcgtctgga ggaagaaaag cgtcgccagc aggcatggga cgctgctcac  1440
ccggaagagg ggctgaaaag agagtatgat aaagcgaaag ctgagctgga tgctgaagat  1500
aaaaatattg cgaccttaaa cagtcgcatt gcatcgcacg agaaggcgat ccccggtgca  1560
agggctgctg ttcaggaagc cgataaaaag gtaaaagagg cagaggcaaa taaagatgat  1620
```

```
tttgtgactt ataacccgcc tcatgaatat ggctccgggt ggcaggatca ggttcgctat  1680
cttgataagg atattcagaa tcagaatgag aaattaaaag ctgcccagac atctttaaac  1740
gaaatgaatg aatccttatc cagggataag gctgcgcttt ccggggcgat ggagagccgg  1800
aaacaaaagg agaaaaaagc gaaggatgca gaaaataaat taaatgagga aaagaaaaaa  1860
cctcgtaagg gaactaaaga ttacggccat gattattttc ctgatcccaa gactgaagat  1920
attaaggggt tgggagagtt gaaagagggt aaacctaaaa cccctaaaca aggtggtggt  1980
ggtaagcggg cccgatggta tggtgataaa aagcgtaaaa tttatgaatg ggattcccag  2040
cacggtgagc ttgaagggta ccgcgccagt gatggcgaac acctcggggc attcgatcca  2100
aaaacgggta agcaggttaa agggccggat ccaaaacgaa acattaaaaa atatctttaa  2160
gaggtaagta tgggacttaa attaaattta acctggtttg ataagaaaac cgaagagttt  2220
aaaggtggtg aatactcaaa agacttcggt gatgatggtt ctgtcattga aagtctgggg  2280
atgcctttaa aggataatat taataatggt tggtttgatg ttgaaaaatc atgggtttcg  2340
atattacagc cacacttaa aaatgtaatc gatattagta aatttgatta ctttgtatca  2400
tttgattatc gggatggtaa ctggtaa                                      2427

SEQ ID NO: 3        moltype = AA    length = 815
FEATURE             Location/Qualifiers
source              1..815
                    mol_type = protein
                    organism = synthetic construct
SEQUENCE: 3
MPEETLTVVG GGNNSCNVSW GGGNGNNGGA GYSGKYGGTS YEGATSMLKL NDRVLIQLYL   60
CNPLNPDYIG APWGSDKDAE SIIRANRDKA GKFKANIQNW KTSGTGSLGS PVVGKSYSSG  120
DVDTYSVSFG KEKYNVLYNR KKDSFTTAYV DGGANKPEHS GSGSASGSGG DGRGPGNSGL  180
GHNGGQASGN VNGTSGKGGP SSGGGTDPNS GPGWGTTHTP NGDIHNYNPG EFGNGGSKPG  240
GNGGNSGNHS GSSGGGQSSA TAMAFGLPAL ATPGAEGLAL SVSGDALSAA VADVLAALKG  300
PFKFGLWGIA IYGVLPSEIA KDDPKMMSKI VTSLPADTVT ETPVSSLPLD QATVSVTKRV  360
ADIVKDERQH IAVVTGRPMS VPVVDAKPTK RPGVFSVSIP GLPSLQVSVP KGVPAAKAPP  420
KGIIAEKGDS RPAGFTAGGN SREAVIRFPK ESGQKPVYVS VTDVLTPAQV KQRLEEEKRR  480
QQAWDAAHPE EGLKREYDKA KAELDAEDKN IATLNSRIAS TEKAIPGARA AVQEADKKVK  540
EAEANKDDFV TYNPPHEYGS GWQDQVRYLD KDIQNQNEKL KAAQTSLNEM NESLSRDKAA  600
LSGAMESRKQ KEKKAKDAEN KLNEEKKKPR KGTKDYGHDY FPDPKTEDIK GLGELKEGKP  660
KTPKQGGGGK RARWYGDKKR KIYEWDSQHG ELEGYRASDG EHLGAFDPKT GKQVKGPDPK  720
RNIKKYLEVS MGLKLNLTWF DKKTEEFKGG EYSKDFGDDG SVIESLGMPL KDNINNGWFD  780
VEKSWVSILQ PHFKNVIDIS KFDYFVSFDY RDGNW                             815

SEQ ID NO: 4        moltype = DNA    length = 2448
FEATURE             Location/Qualifiers
source              1..2448
                    mol_type = other DNA
                    organism = synthetic construct
SEQUENCE: 4
atgcctgaag aaacattgac tgtcgtaggt ggtggtaata acagctgtaa tgttagctgg   60
ggtggtggca atggtaacaa cggtggtgct ggctattctg gtaaatacgg tggtactagc  120
tatgaaggtg caactagtat gttgaagttg aatgaccgtg tttaattca gctttatctt  180
tgcaatccgc ttaacccaga ttatattgga gcaccttggg cagtgataa agatgcagaa  240
tcaattatca gagctaacag agataaagca ggaaagttca aggctaatat tcagaactgg  300
aaaacaagcg gtacaggttc tttaggtagc cctgtagttg ggaaatctta tagctcaggt  360
gatgtagata cttattcggt tagcttcgga aaagaaaaat acaatgtcct gtataaccgt  420
aaaaaagact ctttttactac agcttatgtc gatggcggcg caaatacc tgagcatggc  480
tccggatcgg cttctgggag tggtggagac ggacgaggtc cgggtaattc aggtctggga  540
cacaatggtg gtcaggccag tgggaatgtg aacggtacat caggtaaagg tggcccttca  600
tcaggtggtg gtacggatcc aaacagcggg ccgggctggg gtacgacgca tacacctaac  660
ggggatattc ataactataa cccggggag tttggtaacg gcgggagtaa acccggtggt  720
aatggcggta acagcggcaa tcatagcggg agctctgggt gcggacagtc ttcggccagc  780
gcgatggcct tcggtctgcc tgccttggcc actccggggg ctgaaggact ggctttatcc  840
gtttccggcg atgcgttgtc ggccgctgtt gctgatgtgc tggctgccct gaaaggtccg  900
tttaagtttg gtctgtgggg gattgcgatt tacgagtgc tgccttctga tagcaaaa  960
gatgatccga aaatgatgtc aaaaatcgtg acgtcattgc cggcagacac ggtaacggag  1020
acgccggtca gctccctgcc gctggaccag gcgacggtca gcgtcactaa acgtgtggcg  1080
gatattgtga aggacgagcg gcagcatatt gcggttgtca ccggccggcc aatgagtgtt  1140
cctgtggtg atgcgaaacc gacaaaacgt ccggggtat tcagtgtgtc gattccgggt  1200
ctcccgtctc tgcaggtgag cgtacctaaa ggtgttccgg ccgcgaaagc cccgccaaaa  1260
ggcattattg ctgaaaaagg tgattcacgt ccggctggt ttacggccgg tggtaactcc  1320
cgtgaagccg ttattcgttt cccgaaagag agcggacaga aaccggtcta tgtgtcggtg  1380
acggatgttc ttactccggc acaggtaaaa cagcgtctgg aggaagaaaa gcgtcgccag  1440
caggcatggg acgctgctca cccggaagag gggctgaaaa gagagtatga taaagcgaaa  1500
gctgagctgg atgctgaaga taaaaatatt gcgaccttaa acagtcgcat tgcatcgaca  1560
gagaaggcaa tccccggtgc aagggctgct gttcaggaag ccgataaaaa ggtaaaagag  1620
gcagaggcaa ataaagatga ttttgtgact tataacccgc ctcatgaata tggctccggg  1680
tggcaggatc aggttcgcta tcttgataag gatattcaga atcagaatga gaaattaaaa  1740
gctgcccaga catctttaaa cgaaatgaat gaatccttat ccagggataa ggctgcgctt  1800
tccggggcga tggagagccg gaaacaaaag gagaaaaaag cgaaggatgc agaaaataaa  1860
ttaaatgagg aaaagaaaaa acctcgtaag ggaactaaag attacggcca ttgattattt  1920
cctgatccca agactgaaga tattaagggg ttgggagagt tgaaagaggg taaacctaaa  1980
accctaaac aaggtggtgg tggtaagcgg gcccgatggt atggtgataa aaagcgtaaa  2040
atttatgaat gggattccca gcacggtgag cttgaaggg accgcgccag tgatggcgaa  2100
cacctcgggg cattcgatcc aaaaacgggt aagcaggtta aagggccgga tccaaaacga  2160
aacattaaaa aatatcttta agaggtaagt atgggactta aattaaattt aacctggttt  2220
```

-continued

```
gataagaaaa ccgaagagtt taaaggtggt gaatactcaa aagacttcgg tgatgatggt  2280
tctgtcattg aaagtctggg gatgccttta aaggataata ttaataatgg ttggtttgat  2340
gttgaaaaat catgggtttc gatattacag ccacacttta aaaatgtaat cgatattagt  2400
aaatttgatt actttgtatc atttgattat cgggatggta actggtaa              2448
```

```
SEQ ID NO: 5              moltype = AA   length = 818
FEATURE                   Location/Qualifiers
source                    1..818
                          mol_type = protein
                          organism = synthetic construct
SEQUENCE: 5
MPEETLTVVG GGNNSCNVSW GGGNGNNGGA GYSGKYGGTS YEGATSMLKL NDRVLIQLYL   60
CNPLNPDYIG APWGSDKDAE SIIRANRDKA GKFKANIQNW KTSGTGSLGS PVVGKSYSSG  120
DVDTYSVSFG KEKYNVLYNR KKDSFTTAYV DGGANKPEHS EAAAKEAAAK SGGDGRGPGN  180
SGLGHNGGQA SGNVNGTSGK GGPSSGGGTD PNSGPGWGTT HTPNGDIHNY NPGEFGNGGS  240
KPGGNGGNSG NHSGSSGGGQ SSATAMAFGL PALATPGAEG LALSVSGDAL SAAVADVLAA  300
LKGPFKFGLW GIAIYGVLPS EIAKDDPKMM SKIVTSLPAD TVTETPVSSL PLDQATVSVT  360
KRVADIVKDE RQHIAVVTGR PMSVPVVDAK PTKRPGVFSV SIPGLPSLQV SVPKGVPAAK  420
APPKGIIAEK GDSRPAGFTA GGNSREAVIR FPKESGQKPV YVSVTDVLTP AQVKQRLEEE  480
KRRQQAWDAA HPEEGLKREY DKAKAELDAE DKNIATLNSR IASTEKAIPG ARAAVQEADK  540
KVKEAEANKD DFVTYNPPHE YGSGWQDQVR YLDKDIQNQN EKLKAAQTSL NEMNESLSRD  600
KAALSGAMES RKQKEKKAKD AENKLNEEKK KPRKGTKDYG HDYFPDPKTE DIKGLGELKE  660
GKPKTPKQGG GGKRARWYGD KKRKIYEWDS QHGELEGYRA SDGEHLGAFD PKTGKQVKGP  720
DPKRNIKKYL EVSMGLKLNL TWFDKKTEEF KGGEYSKDFG DDGSVIESLG MPLKDNINNG  780
WFDVEKSWVS ILQPHFKNVI DISKFDYFVS FDYRDGNW                          818
```

```
SEQ ID NO: 6              moltype = DNA   length = 2457
FEATURE                   Location/Qualifiers
source                    1..2457
                          mol_type = other DNA
                          organism = synthetic construct
SEQUENCE: 6
atgcctgaag aaacattgac tgtcgtaggt ggtggtaata acagctgtaa tgttagctgg   60
ggtggtggca atggtaacaa cggtggtgct ggctattctg gtaaatacgg tggtactagc  120
tatgaaggtg caactagtat gttgaagttg aatgaccgtg ttttaattca gctttatctt  180
tgcaatccgc ttaacccaga ttatattgga gcaccttggg gcagtgataa agatgcagaa  240
tcaattatca gagctaacag agataaagca ggaaagttca aggctaatat tcagaactgg  300
aaaacaagcg gtacaggttc tttaggtagc cctgtagttg gaaatctta tagtctcaggt  360
gatgtagata cttattcggt tagcttcgga aagaaaaat acaatgtcct gtataaccgt  420
aaaaaagact cttttactac agcttatgtc gatggcggcg caaataaacc tgagcatgaa  480
gccgctgcca aggaggcggc cgctaaaagt ggtggagacg gacgaggtcc gggtaattca  540
ggtctgggac acaatggtgg tcaggccagt gggaatgtga acggtacatc aggtaaaggt  600
ggcccttcat caggtggtgg tacggatcca aacagcggc cgggctgggg tacgacgcat  660
acacctaacg gggatattca taactataac ccggggagt ttggtaacgg cgggagtaaa  720
cccggtggta atgccggtaa cagcggcaat catagcggga gctctggtgg cggacagtct  780
tcggccaccg cgatggcctt cggtctgcct gccttggcca ctccggggc tgaaggactg  840
gctttatccg tttccggcga tgcgttgtcg gccgctgttg ctgatgtgct ggctgccctg  900
aaaggtccgt ttaagtttgg tctgtggggg attgcgattt acggagtgct gccttctgag  960
atagcaaaag atgatccgaa aatgatgtca aaaatcgtga cgtcattgcc ggcagacacg  1020
gtaacggaga cgccggtcag ctccctgccg ctggaccagg cgacggtcag cgtcactaaa  1080
cgtgtggcgg atattgtgaa ggacgagcgg cagcatattg cggttgtcac cggccggcat  1140
atgagtgttc ctgtggtgga tgcgaaaccg acaaaacgtc cggggggtatt cagtgtgtcg  1200
attccgggtc tcccgtctct gcaggtgagc gtacctaaag gtgttccggc cgcgaaagcc  1260
ccgccaaaag gcattattgc tgaaaaaggt gattcacgtc cggctggttt tacggccggt  1320
ggtaactccc gtgaagccgt tattcgtttc ccgaaagaga gcggacagaa accggtctat  1380
gtgtcggtga cggatgttct tactccggca caggtaaaac agcgtctgga ggaagaaaag  1440
cgtcgccagc aggcatggga cgctgctcac ccggaagagg ggctgaaaag agagtatgat  1500
aaagcgaaag ctgagctgga tgctgaagat aaaaatattg cgaccttaaa cagtcgcatt  1560
gcatcgacag agaaggcgat ccccggtgca agggctgctg ttcaggaagc cgataaaaag  1620
gtaaaagagg cagaggcaaa taaagatgat tttgtgactt ataacccgcc tcatgaatat  1680
ggctccgggt ggcaggatca ggttcgctat cttgataagg atattcagaa tcagaatgag  1740
aaattaaaag ctgcccagac atctttaaac gaaatgaatg aatccttatc cagggataag  1800
gctgcgcttt ccggggcgat ggagagccgg aaacaaaagg agaaaaaagc gaaggatgca  1860
gaaaataaat taaatgagga aaagaaaaaa cctcgtaagg gaacgaaaga ttacggccat  1920
gattattttc ctgatcccaa gactgaagat attaaggggt tgggagagtt gaaagagggt  1980
aaacctaaaa cccctaaaca aggtggtggt ggtaagcggg cccgatggta tggtgataaa  2040
aagcgtaaaa tttatgaatg ggattcccag cacggtgagc ttgaagggta ccgcgccagt  2100
gatggcgaac acctcggggc attcgatcca aaaacgggta agcaggttaa agggccggat  2160
ccaaaacgaa acattaaaaa atatctttaa gaggtaagta tgggacttaa attaaattta  2220
acctggtttg ataagaaaac cgaagagttt aaaggtggtg aatactcaaa agacttcggt  2280
gatgatggtt ctgtcattga aagtctgggg atgcctttaa aggataatat taataatggt  2340
tggtttgatg ttgaaaaatc atgggtttcg atattacagc cacactttaa aaatgtaatc  2400
gatattagta aatttgatta ctttgtatca tttgattatc gggatggtaa ctggtaa     2457
```

```
SEQ ID NO: 7              moltype = AA   length = 846
FEATURE                   Location/Qualifiers
source                    1..846
                          mol_type = protein
                          organism = synthetic construct
```

```
SEQUENCE: 7
MSGGDGRGPG NSGLGHNGGQ ASGNVNGTSG KGGPSSGGGT DPNSGPGWGT THTPNGDIHN  60
YNPGEFGNGG SKPGGNGGNS GNHSGSSGGG QSSATAMAFG LPALATPGAE GLALSVSGDA  120
LSAAVADVLA ALKGPFKFGL WGIAIYGVLP SEIAKDDPKM MSKIVTSLPA DTVTETPVSS  180
LPLDQATVSV TKRVADIVKD ERQHIAVVTG RPMSVPVVDA KPTKRPGVFS VSIPGLPSLQ  240
VSVPKGVPAA KAPPKGIIAE KGDSRPAGFT AGGNSREAVI RFPKESGQKP VYVSVTDVLT  300
PAQVKQRLEE EKRRQQAWDA AHPEEGLKRE YDKAKAELDA EDKNIATLNS RIASTEKAIP  360
GARAAVQEAD KKVKEAEANK DDFVTYNPPH EYGSGWQDQV RYLDKDIQNQ NEKLKAAQTS  420
LNEMNESLSR DKAALSGAME SRKQKEKKAK DAENKLNEEK EAAAKEAAAK PEETLTVVGG  480
GNNSCNVSWG GGNGNNGGAG YSGKYGGTSY EGATSMLKLN DRVLIQLYLC NPLNPDYIGA  540
PWGSDKDAES IIRANRDKAG KFKANIQNWK TSGTGSLGSP VVGKSYSSGD VDTYSVSFGK  600
EKYNVLYNRK KDSFTTAYVD GGANKPEHSM KDQAIAVVKL YLLNESQASV IDTTSGIITD  660
SGKTLSGKLG DKYNTLAKEA ADNIKNFQGK KLRSFNDAMA SINELANNPK MKLSQADKTV  720
VSNALKQMDL SALADRFKGL EKAFTWGDRL LKAEKIREGV VTGITTGDWQ KLAFEVEAMY  780
LSGVAGAVAL GITTAMISTV AVALSLPAVA VSALTVVSVI GISILTSYID ADKAKALNNA  840
VLGLFK                                                              846

SEQ ID NO: 8          moltype = DNA   length = 2541
FEATURE               Location/Qualifiers
source                1..2541
                      mol_type = other DNA
                      organism = synthetic construct
SEQUENCE: 8
atgagtggtg gagacggacg aggtccgggt aattcaggtc tgggacacaa tggtggtcag  60
gccagtggga atgtgaacgg tacatcaggt aaaggtggcc cttcatcagg tggtggtacg  120
gatccaaaca gcgggccggg ctggggtacg acgcatcac ctaacgggga tattcataac  180
tataacccgg gggagtttgg taacggcggg agtaaacccg gtggtaatgg cggtaacagc  240
ggcaatcata gcgggagctc tggtggcgga cagtcttcgg ccaccgcgat ggccttcggt  300
ctgcctgcct tggccactcc gggggctgaa ggactggctt tatccgtttc cggcgatgcg  360
ttgtcggccg ctgttgctga tgtgctggct gccctgaaga gtcgtttaa gtttggtctg  420
tgggggattg cgatttacgg agtgctgcct tctgagatag caaaagatga tccgaaaatg  480
atgtcaaaaa tcgtgacgtc attgccggca gacacggtaa cggagacgcc ggtcagctcc  540
ctgccgctgg accaggcgac ggtcagcgtc actaaacgtg tggcggatat tgtgaaggac  600
gagcggcagc atattgcggt tgtcaccggc cggccaatga gtgttcctgt ggtggatgcg  660
aaaccgacaa aacgtccggg ggtattcagt gtgtcgattc cgggtctccc gtctctgcag  720
gtgagcgtac ctaaaggtgt tccggccgcg aaagccccgc caaaaggcat tattgctgaa  780
aaaggtgatt cacgtccggc tggttttacg gccggtggta actcccgtga agccgttatt  840
cgtttcccga aagagagcgg acagaaaccg gtctatgtgt cggtgacgga tgttcttact  900
ccggcacagg taaaacagcg tctggaggaa gaaaagcgtc gccagcaggc atgggacgct  960
gctcacccgg aagaggggct gaaaagagag tatgataaag cgaaagctga gctggatgct  1020
gaagataaaa atattgcgac cttaaacagt cgcattgcat cgacagagaa ggcgatcccc  1080
ggtgcaaggg ctgctgttca ggaagccgat aaaaaggtaa aagaggcaga ggcaaataaa  1140
gatgattttg tgacttataa cccgcctcat gaatatggct ccggtgggca ggatcaggtt  1200
cgctatcttg ataaggatat tcagaatcag aatgagaaat taaaagctgc ccagacatct  1260
ttaaacgaaa tgaatgaatc cttatccagg gataaggctg cgctttccgg ggcgatggag  1320
agccggaaac aaaaggagaa aaaagcgaag gatgcagaaa ataaattaaa tgaggaaaag  1380
gaagccgctg ccaaggaggc ggccgctaaa cctgaagaaa cattgactgt cgtaggtggt  1440
ggtaataaca gctgtaatgt tagctggggt ggtggcaatg gtaacaacgg tggtgctggc  1500
tattctggta aataccggtgg tactagctat gaaggtgcaa ctagtatgtt gaagttgaat  1560
gaccgtgttt taattcagct ttatctttgc aatccgctta acccagatta tattggagca  1620
ccttggggca gtgataaaga tgcagaatca attatcagag ctaacagaga taaagcagga  1680
aagttcaagg ctaatattca gaactggaaa acaagcggta caggttcttt aggtagccct  1740
gtagttggga aatcttatag ctcaggtgat gtagatactt attcggttag cttcggaaaa  1800
gaaaaataca atgtcctgta taaccgtaaa aaagactctt ttactacagc ttatgtcgat  1860
ggcggcgcaa ataaacctga gcatagcatg aaggatcagg ctattgccgt tgttaaactt  1920
taccttctca acgaaagtca ggcatccggta atcgatacta catcggggaat tattactgac  1980
tctggtaaaa ctcttagcgg gaaattaggt gataaataca cactctggc gaaagaagct  2040
gctgacaata taaaaaactt ccagggtaag aaactccgca gttttaatga tgctatggca  2100
tctattaatg aactagctaa caatccaaag atgaagttaa gtcaggcgga taaaacagtc  2160
gtttctaatg ccctcaaaca aatggatttg tcagcactag ctgaccgatt caaagggtta  2220
gagaaagcct ttacttgggg tgatcgactt cttaaagccg agaaaatcag agaaggtgtt  2280
gttactggta ttaccacagg ggactggcaa aagctggcgt ttgaggttga agctatgtac  2340
ctcagtggtg ttgctggcgc cgtagcgtta gggattacta ctgccatgat tagcacagtc  2400
gcagtcgctt tgtcacttcc agctgtagct gtctctgcgc ttactgttgt gtccgtcatt  2460
ggcatctcta ttctcacatc ttatatcgat gctgataagg ccaaagcact gaataatgca  2520
gtgcttggct tatttaaata a                                              2541

SEQ ID NO: 9          moltype = AA   length = 843
FEATURE               Location/Qualifiers
source                1..843
                      mol_type = protein
                      organism = synthetic construct
SEQUENCE: 9
MSGGDGRGPG NSGLGHNGGQ ASGNVNGTSG KGGPSSGGGT DPNSGPGWGT THTPNGDIHN  60
YNPGEFGNGG SKPGGNGGNS GNHSGSSGGG QSSATAMAFG LPALATPGAE GLALSVSGDA  120
LSAAVADVLA ALKGPFKFGL WGIAIYGVLP SEIAKDDPKM MSKIVTSLPA DTVTETPVSS  180
LPLDQATVSV TKRVADIVKD ERQHIAVVTG RPMSVPVVDA KPTKRPGVFS VSIPGLPSLQ  240
VSVPKGVPAA KAPPKGIIAE KGDSRPAGFT AGGNSREAVI RFPKESGQKP VYVSVTDVLT  300
PAQVKQRLEE EKRRQQAWDA AHPEEGLKRE YDKAKAELDA EDKNIATLNS RIASTEKAIP  360
```

-continued

```
GARAAVQEAD KKVKEAEANK DDFVTYNPPH EYGSGWQDQV RYLDKDIQNQ NEKLKAAQTS   420
LNEMNESLSR DKAALSGAME SRKQKEKKAK DAENKLNEEK GSGSASGPEE TLTVVGGGNN   480
SCNVSWGGGN GNNGGAGYSG KYGGTSYEGA TSMLKLNDRV LIQLYLCNPL NPDYIGAPWG   540
SDKDAESIIR ANRDKAGKFK ANIQNWKTSG TGSLGSPVVG KSYSSGDVDT YSVSFGKEKY   600
NVLYNRKKDS FTTAYVDGGA NKPEHSMKDQ AIAVVKLYLL NESQASVIDT TSGIITDSGK   660
TLSGKLGDKY NTLAKEAADN IKNFQGKKLR SFNDAMASIN ELANNPKMKL SQADKTVVSN   720
ALKQMDLSAL ADRFKGLEKA FTWGDRLLKA EKIREGVVTG ITTGDWQKLA FEVEAMYLSG   780
VAGAVALGIT TAMISTVAVA LSLPAVAVSA LTVVSVIGIS ILTSYIDADK AKALNNAVLG   840
LFK                                                                 843

SEQ ID NO: 10          moltype = DNA   length = 2532
FEATURE                Location/Qualifiers
source                 1..2532
                       mol_type = other DNA
                       organism = synthetic construct SEQUENCE: 10
atgagtggtg gagacggacg aggtccgggt aattcaggtc tgggacacaa tggtggtcag    60
gccagtggga atgtgaacgg tacatcaggt aaaggtggc cttcatcagg tggtggtacg    120
gatccaaaca gcgggccggg ctggggtacg acgcatacac ctaacgggga tattcataac    180
tataaccccg gggagtttgg taacggcggg agtaaacccg gtggtaatgg cggtaacagc    240
ggcaatcata gcgggagctc tggtggcgga cagtcttcgg ccaccgcgat ggccttcggt    300
ctgcctgcct tggccactcc gggggctgaa ggactggctt tatccgtttc cggcgatgcg    360
ttgtcggccg ctgttgctga tgtgctggct gccctgaaag tccgtttaa gtttggtctg    420
tgggggattg cgatttacgg agtgctgcct tctgagatag caaaagatga tccgaaaatg    480
atgtcaaaaa tcgtgacgtc attgccggca gacacggtaa cggagacgcc ggtcagctcc    540
ctgccgctgg accaggcgac ggtcagcgtc actaaacgtg ttgccgatat tgtgaaggac    600
gagcggcagc atattgcggt tgtcaccggc cggccaatga gtgttcctgt ggtggatgc    660
aaaccgacaa aacgtccggg ggtattcagt gtgtcgattc cgggtctccc gtctctgcag    720
gtgagcgtac ctaaaggtgt tccggccgcg aaagccccgc caaaaggcat tattgctgaa    780
aaaggtgatt cacgtccggc tggttttacg gccggtgcga actcccgtga agccgttatt    840
cgtttcccga aagagagcgg acagaaaccg gtctatgtgt cggtgacgga tgttcttact    900
ccggcacagg taaaacagcg tctggaggaa gaaaagcgtc gccagcaggc atgggacgct    960
gctcacccgg aagaggggct gaaaagagag tatgataaag cgaaagctga gctggatgct   1020
gaagataaaa atattgcgac cttaaacagt cgcattgcat cgacagagaa ggcgatcccc   1080
ggtgcaaggg ctgctgttca ggaagccgat aaaaaggtaa aagaggcaga ggcaaataaa   1140
gatgattttg tgacttataa cccgcctcat gaatatggct ccgggtggca ggatcaggtt   1200
cgctatcttg ataaggatat tcagaatcag aatgagaaat taaaagctgc ccagacatct   1260
ttaaacgaaa tgaatgaatc cttatccagg gataaggctg cgctttccgg ggcgatggag   1320
agccgaaaac aaaaggagaa aaaagcgaag gatgcagaaa ataaattaaa tgaggaaaag   1380
ggctccggat cggcttctgg gcctgaagaa acattgactg tcgtaggtgg tggtaataac   1440
agctgtaatg ttagctgggg tggtggcaat ggtaacaacg gtggtgctgg ctattctggt   1500
aaatacggtg gtactagcta tgaaggtgca actagtatgt tgaagttgaa tgaccgtgtt   1560
ttaattcagc tttatctttg caatccgctt aacccagatt atattggagc accttggggc   1620
agtgataaag atgcagaatc aattatcaga gctaacagag ataaagcagg aaagttcaag   1680
gctaatattc agaactggaa aacaagcggt acaggttctt aggtagccc tgtagttggg   1740
aaatcttata gctcaggtga tgtagatact tattcggtta gcttcggaaa agaaaaatac   1800
aatgtcctgt ataaccgtaa aaaagactct tttactacag cttatgtcga tggcggcgca   1860
aataaacctg agcatagcat gaaggatcag gctattgccg ttgttaaact ttaccttctc   1920
aacgaaagtc aggcatcggt aatcgatact acatcgggaa ttattactga ctctggtaaa   1980
actcttagcg ggaaattagg tgataaatac aacactctgg cgaaagaagc tgctgacaat   2040
ataaaaaact tccagggtaa gaaactccgc agtttttaagt atgctatggc atctattaat   2100
gaactagcta caaatccaaa gatgaagtta agtcaggcgg ataaaacagt cgtttctaat   2160
gccctcaaac aaatggattt gtcagcacta gctgaccgat tcaaaagggtt agagaaagcc   2220
tttacttggg gtgatcgact tcttaaagcc gagaaaatca gagaaggtgt tgttactggt   2280
attaccacag gggactggca aaagctggcg tttgaggttg aagctatgta cctcagtggt   2340
gttgctggcg ccgtagcgtt agggattact actgccatga ttagcacagt cgcagtcgct   2400
ttgtcacttc cagctgtagc tgtctctgcg cttactgttg tgtccgtcat tggcatctct   2460
attctcacat cttatatcga tgctgataag gccaaagcac tgaataatgc agtgcttggc   2520
ttatttaaat aa                                                       2532

SEQ ID NO: 11          moltype = AA   length = 785
FEATURE                Location/Qualifiers
source                 1..785
                       mol_type = protein
                       organism = synthetic construct SEQUENCE: 11
MSETMVVVAP PTGFEPAGYG GGLFSPSTPN NSPSQGQIFL QVTLPYYQSA KFCQDSMAWL    60
AQYVKTHGAT DPLTIQVVAN NIRYFLNADT NLCHNPRQNV WEAFHSEMTG SGPAPAKYDY   120
KSMSLKQEAA AKEAAAKSGG DGRGPGNSGL GHNGGQASGN VNGTSGKGGP SSSGGTDPNS   180
GPGWGTTHTP NGDIHNYNPG EFGNGGSKPG GNGGNSGNHS GSSGGGQSSA TAMAFGLPAL   240
ATPGAEGLAL SVSGDALSAA VADVLAALKG PFKFGLWGIA IYGVLPSEIA KDDPKMMSKI   300
VTSLPADTVT ETPVSSLPLD QATVSVTKRV ADIVKDERQH IAVVTGRPMS VPVVDAKPTK   360
RPGVFSVSIP GLPSLQVSVP KGVPAAKAPP KGIIAEKGDS RPAGFTAGGN SREAVIRFPK   420
ESGQKPVYVS VTDVLTPAQV KQRLEEEKRR QQAWDAAHPE EGLKREYDKA KAELDAEDKN   480
IATLNSRIAS TEKAIPGARA AVQEADKKVK EAEANKDDFV TYNPPHEYGS GWQDQVRYLD   540
KDIQNQNEKL KAAQTSLNEM NESLSRDKAA LSGAMESRKQ KEKKAKDAEN KLNEEKKKPR   600
KGTKDYGHDY FPDPKTEDIK GLGELKEGKP KTPKQGGGGK RARWYGDKKR KIYEWDSQHG   660
ELEGYRASDG EHLGAFDPKT GKQVKGPDPK RNIKKYLEVS MGLKLNLTWF DKKTEEFKGG   720
EYSKDFGDDG SVIESLGMPL KDNINNGWFD VEKSWVSILQ PHFKNVIDIS KFDYFVSFDY   780
```

```
RDGNW                                                            785

SEQ ID NO: 12              moltype = DNA   length = 2361
FEATURE                    Location/Qualifiers
source                     1..2361
                           mol_type = other DNA
                           organism = synthetic construct
SEQUENCE: 12
atgagcgaga ccatggttgt tgttgcgccg ccgaccggtt ttgagccggc ggggttacggt    60
ggtggcctgt tcagcccgag caccccgaac aacagcccga gccagggtca aatcttcctg   120
caagtgaccc tgccgtacta tcagagcgcg aagttttgcc aagacagcat ggcgtggctg   180
gcgcagtacg ttaaaaccca cggcgcgacc gatccgctga ccatccaagt ggttgcgaac   240
aacattcgtt acttcctgaa cgcggacacc aacctgtgcc acaacccgcg tcagaacgtg   300
tgggaggcgt ttcacagcga aatgaccggt agcggtccgg cgccggcgaa gtacgattat   360
aaaagcatga gcctgaagca agaagccgct gccaaggagg cggccgctaa aagtggtgga   420
gacgacgag gtccgggtaa ttcaggtctg ggacacaatg gtggtcaggc cagtgggaat   480
gtgaacggta tcatcaggtaa aggtggccct tcatcaggtg gtggtacgga tccaaacagc   540
gggccgggct ggggtacgac gcatacacct aacggggata ttcataacta taacccgggg   600
gagtttggta acggcgggag taaacccggt ggtaatggcg gtaacagcgg caatcatagc   660
gggagctctg gtggcggaca gtcttcggcc accgcgatgg ccttcggtct gcctgccttg   720
gccactccgg gggctgaagg actggcttta tccgtttccg gcgatgcgtt gtcggccgct   780
gttgctgatg tgctggctgc cctgaaaggt ccgtttaagt ttggtctgtg ggggattgcg   840
atttacggag tgctgccttc tgagatagca aaagatgatc cgaaaatgat gtcaaaaatc   900
gtgacgtcat tgccggcaga cacggtaacg gagacgccgg tcagctccct gccgctggac   960
caggcgacgg tcagcgtcac taaacgtgtg gcggatattg tgaaggacga gcggcagcat  1020
attgcggttg tcaccggccg gccaatgagt gttcctgtgg tggatgcgaa accgacaaaa  1080
cgtccgggg tattcagtgt gtcgattccg ggtctcccgt ctctgcaggt gagcgtacct  1140
aaaggtgttc cggccgcgaa agccccgcca aaaggcatta ttgctgaaaa aggtgattca  1200
cgtccggctg gtttttacggc cggtggtaac tcccgtgaag ccgttattcg tttcccgaaa  1260
gagagcggac agaaaccggt ctatgtgtcg gtgacggatg ttcttactcc ggcacaggta  1320
aaacagcgtc tggaggaaga aaagcgtcgc cagcaggcat gggacgctgc tcacccggaa  1380
gagggggctga aaagagagta tgataaagcg aaagctgagc tggatgctga agataaaaat  1440
attgcgacct taaacagtcg cattgcatcg acagagaagg cgatccccgg tgcaagggct  1500
gctgttcagg aagccgataa aaaggtaaaa gaggcagagg caaataaaga tgattttgtg  1560
acttataacc cgcctcatga atatggctcc gggtggcagg atcaggttcg ctatcttgat  1620
aaggatattc agaatcagaa tgagaaatta aaagctgccc agacatcttt aaacgaaatg  1680
aatgaatcct tatccaggga taaggctgcg ctttccgggg cgatggagag ccggaaacaa  1740
aaggagaaaa aagcgaagga tgcagaaaat aaattaaatg aggaaaagaa aaaacctcgt  1800
aaggaaacta aagattacgg ccatgattat tttcctgatc ccaagactga agatattaag  1860
gggttgggag agttgaaaga gggtaaacct aaaacccta aacaaggtgg tggtggtaag  1920
cgggcccgat ggtatggtga taaaaagcgt aaaatttatg aatgggattc ccagcacggt  1980
gagcttgaag ggtaccgcgc cagtgatggc gaacacctcg gggcattcga tccaaaaacg  2040
ggtaagcagg ttaaagggcc ggatccaaaa cgaaacatta aaaatatct ttaagaggta  2100
agtatgggac ttaaattaaa tttaacctgg tttgataaga aaaccgaaga gtttaaaggt  2160
ggtgaatact caaaagactt cggtgatgat ggttctgtca ttgaaagtct ggggatgcct  2220
ttaaaggata atattaataa tggttggttt gatgttgaaa aatcatgggt ttcgatatta  2280
cagccacact ttaaaaatgt aatcgatatt agtaaatttg attactttgt atcatttgat  2340
tatcgggatg gtaactggta a                                            2361

SEQ ID NO: 13              moltype = AA   length = 744
FEATURE                    Location/Qualifiers
source                     1..744
                           mol_type = protein
                           organism = synthetic construct
SEQUENCE: 13
MSGGDGRGPG NSGLGHNGGQ ASGNVNGTSG KGGPSSGGGT DPNSGPGWGT THTPNGDIHN     60
YNPGEFGNGG SKPGGNGGNS GNHSGSSGGG QSSATAMAFG LPALATPGAE GLALSVSGDA    120
LSAAVADVLA ALKGPFKFGL WGIAIYGVLP SEIAKDDPKM MSKIVTSLPA DTVTETPVSS    180
LPLDQATVSV TKRVADIVKD ERQHIAVVTG RPMSVPVVDA KPTKRPGVFS VSIPGLPSLQ    240
VSVPKGVPAA KAPPKGIIAE KGDSRPAGFT AGGNSREAVI RFPKESGQKP VYVSVTDVLT    300
PAQVKQRLEE EKRRQQAWDA AHPEEGLKRE YDKAKAELDA EDKNIATLNS RIASTEKAIP    360
GARAAVQEAD KKVKEAEANK DDFVTYNPPH EYGSGWQDQV RYLDKDIQNQ NEKLKAAQTS    420
LNEMNESLSR DKAALSGAME SRKQKEKKAK DAENKLNEEK KKPRKETKDY GHDYFPDPKT    480
EPAGYGGGLF SPSTPNNSPS QGQIFLQVTL PYYQSAKFCQ DSMAWLAQYV KTHGATDPLT    540
IQVVANNIRY FLNADTNLCH NPRQNVWEAF HSEMTGSGPA PAKYDYKSMS LKQMSGNVVT    600
PAAAFGHYLW GNGEERYVNL PDVGLKITPQ QIPELMNIVN SGVTGNIPVD LNFNHNTYDS    660
GGVIPASYLG NVSLRTIGSL NIQNSGEWTY NGVVRAYNDY YDFNLGDYRG AIAESLTYLG    720
AQFSGKPYHI AMPGEINISG AGHR                                          744

SEQ ID NO: 14              moltype = DNA   length = 2235
FEATURE                    Location/Qualifiers
source                     1..2235
                           mol_type = other DNA
                           organism = synthetic construct
SEQUENCE: 14
atgagtggtg gagacggacg aggtccgggt aattcaggtc tgggacacaa tggtggtcag     60
gccagtggga atgtgaacgg tacatcaggt aaaggtggcc cttcatcagg tggtggtacg    120
gatccaaaca gcgggccggg ctgggggtacg acgcatacac ctaacgggga tattcataac    180
tataacccgg gggagtttgg taacggcggg agtaaacccg gtggtaatgg cggtaacagc    240
```

-continued

```
ggcaatcata gcgggagctc tggtggcgga cagtcttcgg ccaccgcgat ggccttcggt   300
ctgcctgcct tggccactcc gggggctgaa ggactggctt tatccgtttc cggccgatgcg  360
ttgtcggccg ctgttgctga tgtgctggct gccctgaaag gtccgtttaa gtttggtctg   420
tggggggattg cgatttacgg agtgctgcct tctgagatag caaaagatga tccgaaaatg   480
atgtcaaaaa tcgtgacgtc attgccggca gacacggtaa cggagacgcc ggtcagctcc   540
ctgccgctgg accaggcgac ggtcagcgtc actaaacgtg tggcggatat tgtgaaggac   600
gagcggcagc atattgcggt tgtcaccggc cggccaatga gtgttcctgt ggtggatgcg   660
aaaccgacaa aacgtccggg ggtattcagt gtgtcgattc cgggtctccc gtctctgcag   720
gtgagcgtac ctaaaggtgt tccggccgcg aaagccccgc caaaaggcat tattgctaaa   780
aaaggtgatt cacgtccggc tggttttacg gccggtggta actcccgtga agccgttatt   840
cgtttcccga aagagagcgg acagaaaccg gtctatgtgt cggtgacgga tgttcttact   900
ccggcacagg taaaacagcg tctggaggaa gaaaagcgtc gccagcaggc atgggacgct   960
gctcacccgg aagaggggct gaaaagagag tatgataaag cgaaagctga gctggatgct  1020
gaagataaaa atattgcgac cttaaacagt cgcattgcat cgacacagaa gcgatccccc  1080
ggtgcaaggg ctgctgttca ggaagccgat aaaaaggtaa aagaggcaga ggcaaataaa  1140
gatgattttg tgacttataa cccgcctcat gaatatggct ccgggtggca ggatcaggtt  1200
cgctatcttg ataaggatat tcagaatcag aatgagaaat taaaagctgc ccagacatct  1260
ttaaacgaaa tgaatgaatc cttatccagg gataaggctg cgctttccgg ggcgatggag  1320
agccggaaac aaaaaggagaa aaaagcgaag gatgcagaaa ataaattaaa tgaggaaaag  1380
ggctccggat cggcttctgg gagcgagacc atggttgttg ttgcgccgcc gaccggtttt  1440
gagccggcgg gttacggtgg tggcctgttc agcccgagca ccccgaacaa cagcccgagc  1500
cagggtcaaa tcttcctgca agtgaccctg ccgtactatc agagcgcgaa gttttgccaa  1560
gacagcatgg cgtggctggc gcagtacgtt aaaacccacg gcgcgaccga tccgctgacc  1620
atccaagtgg ttgcgaacaa cattcgttac ttcctgaacg cggacaccaa cctgtgccac  1680
aacccgcgtc agaacgtgtg ggaggcgttt cacagcgaaa tgaccggtag cggtccggcg  1740
ccggcgaagt acgattataa aagcatgagc ctgaagcaaa gcggtggtaa cggtagcggg  1800
ccggcggcgg cgtttggtca ctacctgtgg ggtaacggcg aggaacgtta tgtgaacctg  1860
ccggacgttg gtctgaaaat caccccgcag caaattccgg agctgatgaa catcgtgaac  1920
agcggtgtta ccggcaacat tccggttgac ctgaactttta accacaacac ctacgatagc  1980
ggtggcgtga tcccggcgag ctatctgggt aacgttagcc tgcgtaccat cggcagcctg  2040
aacattcaga acagcggcga gtggacctac aacggcgtgg ttcgtgcgta taacgactac  2100
tatgatttca acctgggtga ttaccgtggc gcgattgcgg aaagcctgac ctatctgggc  2160
gcgcaattta gcggtaagcc gtatcacatt gcgatgccgg cgaaatcaa cattagcggt   2220
gcgggtcatc gttaa                                                    2235

SEQ ID NO: 15           moltype = AA  length = 782
FEATURE                 Location/Qualifiers
source                  1..782
                        mol_type = protein
                        organism = synthetic construct
SEQUENCE: 15
MSETMVVVAP PTGFEPAGYG GGLFSPSTPN NSPSQGQIFL QVTLPYYQSA KFCQDSMAWL   60
AQYVKTHGAT DPLTIQVVAN NIRYFLNADT NLCHNPRQNV WEAFHSEMTG SGPAPAKYDY   120
KSMSLKQGSG SASGSGGDGR GPGNSGLGHN GGQASGNVNG TSGKGGPSSG GGTDPNSGPG   180
WGTTHTPNGD IHNYNPGEFG NGGSKPGGNG GNSGNHSGSS GGGQSSATAM AFGLPALATP   240
GAEGLALSVS GDALSAAVAD VLAALKGPFK FGLWGIAIYG VLPSEIAKDD PKMMSKIVTS   300
LPADTVTETP VSSLPLDQAT VSVTKRVADI VKDERQHIAV VTGRPMSVPV VDAKPTKRPG   360
VFSVSIPGLP SLQVSVPKGV PAAKAPPKGI IAEKGDSRPA GFTAGGNSRE AVIRFPKESG   420
QKPVYVSVTD VLTPAQVKQR LEEEKRRQQA WDAAHPEEGL KREYDKAKAE LDAEDKNIAT   480
LNSRIASTEK AIPGARAAVQ EADKKVKEAE ANKDDFVTYN PPHEYGSGWQ DQVRYLDKDI   540
QNQNEKLKAA QTSLNEMNES LSRDKAALSG AMESRKQKEK KAKDAENKLN EEKKKPRKGT   600
KDYGHDYFPD PKTEDIKGLG ELKEGKPKTP KQGGGGKRAR WYGDKKRKIY EWDSQHGELE   660
GYRASDGEHL GAFDPKTGKQ VKGPDPKRNI KKYLEVSMGL KLNLTWFDKK TEEFKGGEYS   720
KDFGDDGSVI ESLGMPLKDN INNGWFDVEK SWVSILQPHF KNVIDISKFD YFVSFDYRDG   780
NW                                                                  782

SEQ ID NO: 16           moltype = DNA  length = 2352
FEATURE                 Location/Qualifiers
source                  1..2352
                        mol_type = other DNA
                        organism = synthetic construct
SEQUENCE: 16
atgagcgaga ccatggttgt tgttgcgccg ccgaccggtt ttgagccggc gggttacggt   60
ggtggcctgt tcagcccgag caccccgaac aacagcccga gatcttcctg   120
caagtgaccc tgccgtacta tcagagcgcg aagttttgcc aagacagcat ggcgtggctg   180
gcgcagtacg ttaaaaccca cggcgcgacc gatccgctga ccatccaagt ggttgcgaac   240
aacattcgtt acttcctgaa cgcggacacc aacctgtgcc acaacccgcg tcagaacgtg   300
tgggaggcgt ttcacagcga aatgaccggt agcggtccgg cgccggcgaa gtacgattat   360
aaaagcatga gcctgaagca aagcggtggt aacggtagcg gaccggcggc gacggagaca  420
ggtccgggta ttcaggtctc tgggacacaat ggtggtcagg ccagtgggaa tgtgaacggt   480
acatcaggta aaggtggccc ttcatcaggt ggtggtacgg atccaaacag cgggccgggc   540
tggggtacga cgcatacacc taacggggat attcataact ataacccggg ggagtttggt   600
aacggcggga gtaaacccgg tggtaatggc ggtaacagcg gcaatcatag cgggagctct   660
ggtggtcagt cttcggccac cgcgatggcc ttcggtctgc ctgccctggc cactccgggg   720
ggctgaagac tggctttatc cgtttcggcc gatgcgtgtc ggccgctgtt gctgat   780
gtgctgctg ccctgaaagg tccgtttaag tttggtctgt gggggattgc gatttacgga   840
gtgctgcctt ctgagatagc aaaagatgat ccgaaaatga tgtcaaaaat cgtgacgtca   900
ttgccggcag acacggtaac ggagacgccg gtcagctccc tgccgctgga ccaggcgacg   960
gtcagcgtca ctaaacgtgt ggcggatatt gtgaaggacg agcggcagca tattgcggtt  1020
```

-continued

```
gtcaccggcc ggccaatgag tgttcctgtg gtggatgcga aaccgacaaa acgtccgggg   1080
gtattcagtg tgtcgattcc gggtctcccg tctctgcagg tgagcgtacc taaaggtgtt   1140
ccggccgcga aagccccgcc aaaaggcatt attgctgaaa aaggtgattc acgtccggct   1200
ggtttttacg ccggtggtaa ctcccgtgaa gccgttattc gtttcccgaa agagagcgga   1260
cagaaaccgg tctatgtgtc ggtgacggat gttcttactc cggcacaggt aaaacagcgt   1320
ctggaggaag aaaagcgtcg ccagcaggca tgggacgctg ctcacccgga agaggggctg   1380
aaaagagagt atgataaagc gaaagctgag ctggatgctg aagataaaaa tattgcgacc   1440
ttaaacagtc gcattgcatc gacagagaag gcgatccccg tgcaagggc tgctgttcag   1500
gaagccgata aaaaggtaaa agaggcgag gcaaataaat atgattttgt gacttataac   1560
ccgcctcatg aatatggctc cgggtgggcag gatcaggttc gctatcttga taaggatatt   1620
cagaatcaga atgagaaatt aaaagctgcc cagacatctt taaacgaaat gaatgaatcc   1680
ttatccaggg ataaggctgc gctttccggg gcgatggaga gccggaaaca aaaggagaaa   1740
aaagcgaagg atgcagaaaa taaattaaat gaggaaaaga aaaaacctcg taagggaact   1800
aaagattacg gccatgatta ttttcctgat cccaagactg aagatattaa ggggttggga   1860
gagttgaaag agggtaaacc taaaacccct aaacaaggtg gtggtggtaa gcgggcccga   1920
tggtatggtg ataaaaagcg taaaatttat gaatgggatt cccagcacgg tgagcttgaa   1980
gggtaccgcg ccagtgatgg cgaacacctc gggcattcg atccaaaaac gggtaagcag   2040
gttaaagggc cggatccaaa acgaaacatt aaaaaatatc tttaagaggt aagtatggga   2100
cttaaattaa atttaacctg gtttgataag aaaaccgaag agtttaaagg tggtgaatac   2160
tcaaaagact tcggtgatga tggttctgtc attgaaagtc tggggatgcc tttaaaggat   2220
aatattaata atggttggtt tgatgttgaa aaatcatggg tttcgatatt acagccacac   2280
tttaaaaatg taatcgatat tagtaaattt gattactttg tatcatttga ttatcgggat   2340
ggtaactggt aa                                                       2352
```

```
SEQ ID NO: 17          moltype = AA   length = 747
FEATURE                Location/Qualifiers
source                 1..747
                       mol_type = protein
                       organism = synthetic construct
SEQUENCE: 17
MSGGDGRGPG NSGLGHNGGQ ASGNVNGTSG KGGPSSGGGT DPNSGPGWGT THTPNGDIHN   60
YNPGEFGNGG SKPGGNGGNS GNHSGSSGGG QSSATAMAFG LPALATPGAE GLALSVSGDA   120
LSAAVADVLA ALKGPFKFGL WGIAIYGVLP SEIAKDDPKM MSKIVTSLPA DTVTETPVSS   180
LPLDQATVSV TKRVADIVKD ERQHIAVVTG RPMSVPVVDA KPTKRPGVFS VSIPGLPSLQ   240
VSVPKGVPAA KAPPKGIIAE KGDSRPAGFT AGGNSREAVI RFPKESGQKP VYVSVTDVLT   300
PAQVKQRLEE EKRRQQAWDA AHPEEGLKRE YDKAKAELDA EDKNIATLNS RIASTEKAIP   360
GARAAVQEAD KKVKEAEANK DDFVTYNPPH EYGSGWQDQV RYLDKDIQNQ NEKLKAAQTS   420
LNEMNESLSR DKAALSGAME SRKQKEKKAK DAENKLNEEK EAAAKEAAAK SETMVVVAPP   480
TGFEPAGYGG GLFSPSTPNN SPSQGQIFLQ VTLPYYQSAK FCQDSMAWLA QYVKTHGATD   540
PLTIQVVANN IRYFLNADTN LCHNPRQNVW EAFHSEMTGS GPAPAKYDYK SMSLKQMSGN   600
VVTPAAAFGH YLWGNGEERY VNLPDVGLKI TPQQIPELMN IVNSGVTGNI PVDLNFNHNT   660
YDSGGVIPAS YLGNVSLRTI GSLNIQNSGE WTYNGVVRAY NDYYDFNLGD YRGAIAESLT   720
YLGAQFSGKP YHIAMPGEIN ISGAGHR                                       747
```

```
SEQ ID NO: 18          moltype = DNA   length = 2244
FEATURE                Location/Qualifiers
source                 1..2244
                       mol_type = other DNA
                       organism = synthetic construct
SEQUENCE: 18
atgagtggtg gagacggacg aggtccgggt aattcaggtc tgggacacaa tggtggtcag   60
gccagtggga atgtgaacgg tacatcaggt aaaggtggcc cttcatcagg tggtggtacg   120
gatccaaaca gcgggccggg ctggggtacg acgcatacac ctaacgggga tattcataac   180
tataacccgg gggagtttgg taacggcggg agtaaaccg gtggtaatgg cggtaacagc   240
ggcaatcata gcgggagctc tggtggcgga cagtcttcgg gccaccgcat ggccttcggt   300
ctgcctgcct tggccactcc gggggctgaa gactggctt tatccgtttc cggcgatgcg   360
ttgtcggccg ctgttgctga tgtgctggct gccctgaaag tccgtttaa gtttggtctg   420
tggggggattc gatttacgg agtgctgcct tctgagatag caaaagatga tccgaaaatg   480
atgtcaaaa tcgtgacgtc attgccggca gacacggtaa cggagacgcc ggtcagctcc   540
ctgccgctgg accaggcgac ggtcagcgtc actaaacgtg tggcggatat tgtgaaggac   600
gagcggcagc atattgcggt tgtcaccggc cggccaatga gtgttcctgt ggtggatgcg   660
aaaccgacaa aacgtccggg ggtattcagt gtgtcgattc cgggtctccc gtctctgcag   720
gtgagcgtac ctaaaggtgt tccggccgcg aaagccccgc caaaaggcat tattgctgaa   780
aaaggtgatt cacgtccggc tggttttacg ccggtggt actcccgtgaa gccgttatt   840
cgtttcccga aagagagcgg acagaaaccg gtctatgtgt cggtgacgga tgttcttact   900
ccggcacagg taaaacagcg tctggaggaa gaaaagcgtc gccagcaggc atgggacgct   960
gctcacccgg aagaggggct gaaaagagag tatgataaag cgaaagctga gctggatgct   1020
gaagataaaa atattgcgac cttaaacagt cgcattgcat cgacagagag ggcgatcccc   1080
gtgcaaggg ctgctgttca ggaagccgat aaaaaggtaa aagaggcga gcaaataaa   1140
gatgattttg tgacttataa cccgcctcat gaatatggct ccgggtggca ggatcaggtt   1200
cgctatcttg ataaggatat tcagaatcag aatgagaaat taaaagctgc ccagacatct   1260
ttaaacgaaa tgaatgaatc cttatccagg gataaggctg cgctttccgg ggcgatggag   1320
agccggaaac aaaaggagaa aaaagcgaag gatgcagaaa ataaattaaa tgaggaaaag   1380
aaaaaacctc gtaagggaac taaagattac ggccatgatt attttcctga tcccaagact   1440
gaagatatta aggggttttg agccgcgggg ttacggtggt ggctgttca gcccgagcac   1500
agcccgagcc agggtcaaat cttcctgcaa gtgaccctgc cgtactatca gagcgcgaag   1560
ttttgccaag acagcatggc gtggctggcg cagtacgtta aaacccacgg cgcgaccgat   1620
ccgctgacca tccaagtggt tgcgaacaac attcgttact tcctgaacgc ggacaccaac   1680
ctgtgccaca acccgcgtca gaacgtgtgg gaggcgtttc acagcgaaat gaccggtagc   1740
```

```
ggtccggcgc cggcgaagta cgattataaa agcatgagcc tgaagcaaat gagcggtaac   1800
gtggttaccc cggcggcggc gtttggtcac tacctgtggg gtaacggcga ggaacgttat   1860
gtgaacctgc cggacgttgg tctgaaaatc accccgcagc aaattccgga gctgatgaac   1920
atcgtgaaca gcggtgttac cggcaacatt ccggttgacc tgaactttaa ccacaacacc   1980
tacgatagcg gtggcgtgat cccggcgagc tatctgggtaa acgttagcct gcgtaccatc   2040
ggcagcctga acattcagaa cagcggcgag tggacctaca acggcgtggt tcgtgcgtat   2100
aacgactact atgatttcaa cctgggtgat taccgtggcg cgattgcgga aagcctgacc   2160
tatctgggcg cgcaatttag cggtaagccg tatcacattg cgatgccggg cgaaatcaac   2220
attagcggtg cgggtcatcg ttaa                                         2244
```

SEQ ID NO: 19            moltype = AA   length = 444
FEATURE                  Location/Qualifiers
source                   1..444
                         mol_type = protein
                         organism = synthetic construct
SEQUENCE: 19
```
MPEETLTVVG GGNNSCNVSW GGGNGNNGGA GYSGKYGGTS YEGATSMLKL NDRVLIQLYL   60
CNPLNPDYIG APWGSDKDAE SIIRANRDKA GKFKANIQNW KTSGTGSLGS PVVGKSYSSG   120
DVDTYSVSFG KEKYNVLYNR KKDSFTTAYV DGGANKPEHS GSGSASGSET MVVVAPPTGF   180
EPAGYGGGLF SPSTPNNSPS QGQIFLQVTL PYYQSAKFCQ DSMAWLAQYV KTHGATDPLT   240
IQVVANNIRY FLNADTNLCH NPRQNVWEAF HSEMTGSGPA PAKYDYKSMS LKQMSGNVVT   300
PAAAFGHYLW GNGEERYVNL PDVGLKITPQ QIPELMNIVN SGVTGNIPVD LNFNHNTYDS   360
GGVIPASYLG NVSLRTIGSL NIQNSGEWTY NGVVRAYNDY YDFNLGDYRG AIAESLTYLG   420
AQFSGKPYHI AMPGEINISG AGHR                                         444
```

SEQ ID NO: 20            moltype = DNA   length = 1332
FEATURE                  Location/Qualifiers
source                   1..1332
                         mol_type = other DNA
                         organism = synthetic construct
SEQUENCE: 20
```
atgcctgaag aaacattgac tgtcgtaggt ggtggtaata acagctgtaa tgttagctgg   60
ggtggtggca atggtaacaa cggtggtgct ggctattctg gtaaatacgg tggtactagc   120
tatgaaggtg caactagtat gttgaagttg aatgaccgtg ttttaattca gctttatctt   180
tgcaatccgc ttaacccaga ttatattgga gcaccttggg gcagtgataa agatgcagaa   240
tcaattatca gagctaacag agataaagca ggaaagttca aggctaatat tcagaactgg   300
aaaacaagcg gtacaggttc tttaggtagc cctgtagttg ggaaatctta tagctcaggt   360
gatgtagata cttattcggt tagcttcgga aaagaaaaat acaatgtcct gtataaccgt   420
aaaaaagact cttttactac agcttatgtc gatggcgggc caaataaacc tgagcatggc   480
tccggatcgg cttctgggag cgagaccatg gttgttgttg cgccgccgac cggttttgag   540
ccggcgggtt acggtggtgg cctgttcagc ccgagcaccc cgaacaacag cccgagccag   600
ggtcaaatct tcctgcaagt gaccctgccg tactatcaga gcgcgaagtt ttgccaagac   660
agcatggcgt ggctggcgca gtacgttaaa acccacggcg cgaccgatcc gctgaccatc   720
caagtggttg cgaacaacat tcgttacttc ctgaacgcgg acaccaacct gtgccacaac   780
ccgcgtcaga acgtgtggga ggcgtttcac agcgaaatga ccggtagcgg tccggcgccg   840
gcgaagtacg attataaaag catgagcctg aagcaaatga gcggtaacgt ggttaccccg   900
gcggcggcgt ttggtcacta cctgtggggt aacggcgaag aacgttatgt gaacctgccg   960
gacgttggtc tgaaaatcac cccgcagcaa attccggagc tgatgaacat cgtgaacagc   1020
ggtgttaccg gcaacattcc ggttgacctg aactttaacc acaacaccta cgatagcggt   1080
ggcgtgatcc cggcgagcta tctgggtaac gttagcctgc gtaccatcgg cagcctgaac   1140
attcagaaca gcggcgagtg gacctacaac ggcgtgtataa ndyyd fnlgd yrg...   1200
gatttcaacc tgggtgatta ccgtggcgcg attgcggaaa gcctgaccta tctgggcgcg   1260
caatttagcg gtaagccgta tcacattgcg atgccgggcg aaatcaacat tagcggtgcg   1320
ggtcatcgtt aa                                                     1332
```

SEQ ID NO: 21            moltype = AA   length = 447
FEATURE                  Location/Qualifiers
source                   1..447
                         mol_type = protein
                         organism = synthetic construct
SEQUENCE: 21
```
MPEETLTVVG GGNNSCNVSW GGGNGNNGGA GYSGKYGGTS YEGATSMLKL NDRVLIQLYL   60
CNPLNPDYIG APWGSDKDAE SIIRANRDKA GKFKANIQNW KTSGTGSLGS PVVGKSYSSG   120
DVDTYSVSFG KEKYNVLYNR KKDSFTTAYV DGGANKPEHS EAAAKEAAAK SETMVVVAPP   180
TGFEPAGYGG GLFSPSTPNN SPSQGQIFLQ VTLPYYQSAK FCQDSMAWLA QYVKTHGATD   240
PLTIQVVANN IRYFLNADTN LCHNPRQNVW EAFHSEMTGS GPAPAKYDYK SMSLKQMSGN   300
VVTPAAAFGH YLWGNGEERY VNLPDVGLKI TPQQIPELMN IVNSGVTGNI PVDLNFNHNT   360
YDSGGVIPAS YLGNVSLRTI GSLNIQNSGE WTYNGVVRAY NDYYDFNLGD YRGAIAESLT   420
YLGAQFSGKP YHIAMPGEIN ISGAGHR                                     447
```

SEQ ID NO: 22            moltype = DNA   length = 1341
FEATURE                  Location/Qualifiers
source                   1..1341
                         mol_type = other DNA
                         organism = synthetic construct
SEQUENCE: 22
```
atgcctgaag aaacattgac tgtcgtaggt ggtggtaata acagctgtaa tgttagctgg   60
ggtggtggca atggtaacaa cggtggtgct ggctattctg gtaaatacgg tggtactagc   120
tatgaaggtg caactagtat gttgaagttg aatgaccgtg ttttaattca gctttatctt   180
```

-continued

```
tgcaatccgc ttaacccaga ttatattgga gcaccttggg gcagtgataa agatgcagaa   240
tcaattatca gagctaacag agataaagca ggaaagttca aggctaatat tcagaactgg   300
aaaacaagcg gtacaggttc tttaggtagc cctgtagttg ggaaatctta tagctcaggt   360
gatgtagata cttattcggt tagcttcgga aaagaaaaat acaatgtcct gtataaccgt   420
aaaaaagact cttttactac agcttatgtc gatggcgcg caaataaacc tgagcatgaa   480
gccgctgcca aggaggcggc cgctaaaagc gagaccatga ttgttgttgc gccgccgacc   540
ggttttgagc cggcgggtta cggtggtggc ctgttcagcc cgagcacccc gaacaacagc   600
ccgagccagg gtcaaatctt cctgcaagtg accctgccgt actatcagag cgcgaagttt   660
tgccaagaca gcatggcgtg gctggcgcag tacgttaaga cccacggcgc gaccgatccg   720
ctgaccatcc aagtggttgc gaacaacatt cgttacttcc tgaacgcgga caccaacctg   780
tgccacaacc cgcgtcagaa cgtgtgggag gcgtttcaca gcgaaatgac cggtagcggt   840
ccggcgccgg cgaagtacga ttataaaagc atgagcctga gcaaatgag cggtaacgtg   900
gttacccgg cggcggcgtt tggtcactac ctgtgggta acggcgagga acgttatgtg   960
aacctgccgg acgttggtct gaaaatcacc ccgcagcaaa ttccggagct gatgaacatc   1020
gtgaacagcg gtgttaccgg caacattccg gttgacctga actttaacca caacacctac   1080
gatagcggtg gcgtgatccc ggcgagctat ctgggtaacg ttagcctgcg taccatcggc   1140
agcctgaaca ttcagaacag cggcgagtgg acctacaacg cgtggttcg tgcgtataac   1200
gactactatg atttcaacct gggtgattac cgtggcgcga ttgcggaaag cctgacctat   1260
ctgggcgcgc aatttagcgg taagccgtat cacattgcga tgccgggcga aatcaacatt   1320
agcggtgcgg gtcatcgtta a                                              1341
```

```
SEQ ID NO: 23          moltype = AA  length = 696
FEATURE                Location/Qualifiers
source                 1..696
                       mol_type = protein
                       organism = synthetic construct
SEQUENCE: 23
MPEETLTVVG GGNNSCNVSW GGGNGNNGGA GYSGKYGGEA AAKEAAAKSG GDGRGPGNSG   60
LGHNGGQASG NVNGTSGKGG PSSGGGTDPN SGPGWGTTHT PNGDIHNYNP GEFGNGGSKP   120
GGNGGNSGNH SGSSGGGQSS ATAMAFGLPA LATPGAEGLA LSVSGDALSA AVADVLAALK   180
GPFKFGLWGI AIYGVLPSEI AKDDPKMMSK IVTSLPADTV TETPVSSLPL DQATVSVTKR   240
VADIVKDERQ HIAVVTGRPM SVPVVDAKPT KRPGVFSVSI PGLPSLQVSV PKGVPAAKAP   300
PKGIIAEKGD SRPAGFTAGG NSREAVIRFP KESGQKPVYV SVTDVLTPAQ VKQRLEEEKR   360
RQQAWDAAHP EEGLKREYDK AKAELDAEDK NIATLNSRIA STEKAIPGAR AAVQEADKKV   420
KEAEANKDDF VTYNPPHEYG SGWQDQVRYL DKDIQNQNEK LKAAQTSLNE MNESLSRDKA   480
ALSGAMESRK QKEKKAKDAE NKLNEEKKKP RKGTKDYGHD YFPDPKTEDI KGLGELKEGK   540
PKTPKQGGGG KRARWYGDKK RKIYEWDSQH GELEGYRASD GEHLGAFDPK TGKQVKGPDP   600
KRNIKKYLEV SMGLKLNLTW FDKKTEEFKG GEYSKDFGDD GSVIESLGMP LKDNINNGWF   660
DVEKSWVSIL QPHFKNVIDI SKFDYFVSFD YRDGNW                             696
```

```
SEQ ID NO: 24          moltype = DNA  length = 2094
FEATURE                Location/Qualifiers
source                 1..2094
                       mol_type = other DNA
                       organism = synthetic construct
SEQUENCE: 24
atgcctgaag aaacattgac tgtcgtaggt ggtggtaata acagctgtaa tgttagctgg   60
ggtggtggca atggtaacaa cggtggtgct ggctattctg gtaaatacgg tggtgaagcc   120
gctgccaagg aggcggccgc taaaagtggt ggagacggac gaggtccggg taattcaggt   180
ctgggacaca tggtggtca ggccagtggg aatgtgaacg gtacatcagg taaaggtggc   240
ccttcatcag gtggtggtac ggatccaaac agcgggccgg gctggggtac gacgcataca   300
cctaacgggg atattcataa ctataacccg ggggagtttg gtaacggcgg gagtaaaccc   360
ggtggtaatg gcggtaacag cggcaatcat agcgggagct ctggtggcgg acagtcttcg   420
gccaccgcga tggccttcgg tctgcctgcc ttggccactc cggggctga aggactggct   480
ttatccgttt ccggcgatgc gttgtcggcc gctgttgctg atgtgctggc tgccctgaaa   540
ggtccgtttta agtttggtct gtgggggatt gcgatttacg gagtgctgcc ttctgagata   600
gcaaaagatg atccgaaaat gatgtcaaaa atcgtgacgt cattgccggc agacacggta   660
acggagacgc cggtcagctc cctgccgctg accaggcga cggtcagcgt cactaaacgt   720
gtggcggata ttgtgaagga cgagcggcag catattgcgg ttgtcaccgg ccggccaatg   780
agtgttcctg tggtggatgc gaaaccgaca aaacgtccgg gggtattcag tgtgtcgatt   840
ccgggtctcc cgtctctgca ggtgagcgta cctaaaggtg ttccggccgc gaaagccccg   900
ccaaaaggca ttattgctga aaaaggtgat tcacgtccgg ctggttttac ggccggtggt   960
aactcccgtg aagccgttat tcgtttcccg aaagagagcg gacagaaacc ggtctatgtg   1020
tcggtgacgg atgttcttac tccggcacag gtaaaacagc gtctggagga agaaaagcgt   1080
cgccagcagg catgggacgc tgctcacccg aagagggggc tgaaaagaga gtatgataaa   1140
gcgaaagctg agctggatgc tgaagataaa aatattgcga ccttaaacag tcgcattgca   1200
tcgacagaga aggcgatccc cggtgcaagg gctgctgttc aggaagccga taaaaaggta   1260
aaagaggcag aggcacaaataa agatgatttt gtgacttata cccgcctca tgaatatggc   1320
tccgggtggc aggatcaggt tcgctatctt gataaggata ttcagaatca gaatgagaaa   1380
ttaaaagctg cccagacatc tttaaacgaa atgaatgaat ccttatccag ggataaggct   1440
gcgctttccg gggcgatgga gagccggaaa caaaaggaga aaaaagcgaa ggatgcagaa   1500
aataaattaa atgaggaaaa gaaaaaacct cgtaaggaa ctaaagatta cggccatgat   1560
tattttcctg atcccaagac tgaagatatt aaggggttgg gagagttgaa agagggtaaa   1620
cctaaaaccc ctaaacaagg tggtggtggt aagcggcgc gatggtatgg tgataaaaag   1680
cgtaaaattt atgaatggga ttcccagcac ggtgagcttg aagggtaccg cgccagtgat   1740
ggcgaacacc tcgggcatt cgatccaaaa acgggtaagc aggttaaagg gccggatcca   1800
aaacgaaaca ttaaaaaata tctttaagag gtaagtatgg gacttaaatt aaatttaacc   1860
tggtttgata agaaaaccga gagtttaaa ggtggtgaat actcaaaaga cttcggtgat   1920
gatggttctg tcattgaaag tctggggatg cctttaaagg ataatattaa taatggttgg   1980
```

-continued

```
tttgatgttg aaaaatcatg ggtttcgata ttacagccac actttaaaaa tgtaatcgat   2040
attagtaaat ttgattactt tgtatcattt gattatcggg atggtaactg gtaa          2094

SEQ ID NO: 25              moltype = AA   length = 664
FEATURE                    Location/Qualifiers
source                     1..664
                           mol_type = protein
                           organism = synthetic construct
SEQUENCE: 25
MPEETLTVVG GGNNSCNVSW GGGNGNNGGA GYSGKYGGTS YEGATSMLKL NDRVLIQLYL    60
CNPLNPDYIG APWGSDKDAE SIIRANRDKA GKFKANIQNW KTSGTGSLGS PVVGKSYSSG    120
DVDTYSVSFG KEKYNVLYNR KKDSFTTAYV DGGANKPEHS MKDQAIAVVK LYLLNESQAS    180
VIDTTSGIIT DSGKTLSGKL GDKYNTLAKE AADNIKNFQG KKLRSFNDAM ASINELANNP    240
KMKLSQADKT VVSNALKQMD LSALADRFKG LEKAFTWGDR LLKAEKIREG VVTGITTGDW    300
QKLAFEVEAM YLSGVAGAVA LGITTAMIST VAVALSLPAV AVSALTVVSV IGISILTSYI    360
DADKAKALNN AVLGLFKEAA AKEAAAKSET MVVVAPPTGF EPAGYGGGLF SPSTPNNSPS    420
QGQIFLQVTL PYYQSAKFCQ DSMAWLAQYV KTHGATDPLT IQVVANNIRY FLNADTNLCH    480
NPRQNVWEAF HSEMTGSGPA PAKYDYKSMS LKQMSGNVVT PAAAFGHYLW GNGEERYVNL    540
PDVGLKITPQ QIPELMNIVN SGVTGNIPVD LNFNHNTYDS GGVIPASYLG NVSLRTIGSL    600
NIQNSGEWTY NGVVRAYNDY YDFNLGDYRG AIAESLTYLG AQFSGKPYHI AMPGEINISG    660
AGHR                                                                 664

SEQ ID NO: 26              moltype = DNA   length = 1995
FEATURE                    Location/Qualifiers
source                     1..1995
                           mol_type = other DNA
                           organism = synthetic construct
SEQUENCE: 26
atgcctgaag aaacattgac tgtcgtaggt ggtggtaata acagctgtaa tgttagctgg   60
ggtggtggca atggtaacaa cggtggtgct ggctattctg gtaaatacgg tggtactagc   120
tatgaaggtg caactagtat gttgaagttg aatgaccgtg ttttaattca gctttatctt   180
tgcaatccgc ttaacccaga ttatattgga gcaccttggg gcagtgataa agatgcagaa   240
tcaattatca gagctaacag agataaagca ggaaagttca aggctaatat tcagaactgg   300
aaaacaagcg gtacaggttc tttaggtagc cctgtagttg ggaaatctta tagctcaggt   360
gatgtagata cttattcggt tagcttcgga aagaaaaat acaatgtcct gtataaccgt    420
aaaaaagact cttttactac agcttatgtc gatggcggcg caaataaacc tgagcatagc   480
atgaaggatc aggctattgc cgttgttaaa ctttaccttc tcaacgaaag tcaggcatcg   540
gtaatcgata ctacatcggg aattattact gactctggta aaactcttag cgggaaatta   600
ggtgataaat acaacactct ggcgaaagaa gctgctgaca atattaaaaa cttccaggqt    660
aagaaactcc gcagtttaa tgatgctatg gcatctatta tgaactagc taacaatcca    720
aagatgaagt taagtcaggc ggataaaaca gtcgtttcta atgccctcaa acaaatggat   780
ttgtcagcac tagctgaccg attcaaaggg ttagagaaag cctttacttg gggtgatcga   840
cttcttaaag ccgagaaaat cagagaaggt gttgttactg gtattaccac aggggactgg   900
caaaagctgg cgtttgaggt tgaagctatg tacctcagtg gtgttgctgg cgccgtagcg   960
ttagggatta ctactgccat gattagcaca gtcgcagtcg ctttgtcact tccagctgta   1020
gctgtctctg cgcttactgt tgtgtccgtc attggcatct ctattctcac atcttatatc   1080
gatgctgata aggccaaagc actgaataat gcagtgcttg gcttatttaa agaagccgct   1140
gccaaggagg cggccgctaa aagcgagacc atggttgttg ttgcgccgcc gaccggtttt   1200
gagccggcgg gttacggtgg tggcctgttc agcccgagca ccccgaacaa cagcccgagc   1260
cagggtcaaa tcttcctgca agtgaccctg ccgtactatc agagcgcgaa gtttgccaa    1320
gacagcatgg cgtggctggc gcagtacgtt aaaacccacg gcgcgaccga tccgctgacc   1380
atccaagtgg ttgcgaacaa cattcgttac ttcctgaacg cggacaccaa cctgtgccaa   1440
aacccgcgtc agaacgtgtg ggaggcgttt cacagcgaaa tgaccggtag cggtccggcg   1500
ccggcgaagt acgattataa aagcatgagc ctgaagcaaa tgagcggtaa cgtggttacc   1560
ccggcgggca cgtttggtca tacctgtgg ggtaacggcg aggaacgtta tgtgaacctg    1620
ccggacgttg gtctgaaaat cacccccgcag caaattccgg agctgatgaa catcgtgaac   1680
agcggtgtta ccggcaacat tccggttgac ctgaacttta ccacaacac ctacgatagc    1740
ggtggcgtga tcccggcgag ctatctgggt aacgttagcc tgcgtaccat cggcagcctg   1800
aacattcaga acagcggcga gtggacctgg aacggcgtg ttcgtgcgta taacgactac    1860
tatgatttca acctgggtga ttaccgtggc gcgattgcgg aaagcctgac ctatctgggc   1920
gcgcaatta gcggtaagcc gtatcacatt gcgatgccgg gcgaaatcaa cattagcggt    1980
gcgggtcatc gttaa                                                    1995

SEQ ID NO: 27              moltype = AA   length = 661
FEATURE                    Location/Qualifiers
source                     1..661
                           mol_type = protein
                           organism = synthetic construct
SEQUENCE: 27
MPEETLTVVG GGNNSCNVSW GGGNGNNGGA GYSGKYGGTS YEGATSMLKL NDRVLIQLYL    60
CNPLNPDYIG APWGSDKDAE SIIRANRDKA GKFKANIQNW KTSGTGSLGS PVVGKSYSSG    120
DVDTYSVSFG KEKYNVLYNR KKDSFTTAYV DGGANKPEHS MKDQAIAVVK LYLLNESQAS    180
VIDTTSGIIT DSGKTLSGKL GDKYNTLAKE AADNIKNFQG KKLRSFNDAM ASINELANNP    240
KMKLSQADKT VVSNALKQMD LSALADRFKG LEKAFTWGDR LLKAEKIREG VVTGITTGDW    300
QKLAFEVEAM YLSGVAGAVA LGITTAMIST VAVALSLPAV AVSALTVVSV IGISILTSYI    360
DADKAKALNN AVLGLFKGSG SASGSETMVV VAPPTGFEPA GYGGGLFSPS TPNNSPSQGQ    420
IFLQVTLPYY QSAKFCQDSM AWLAQYVKTH GATDPLTIQV VANNIRYFLN ADTNLCHNPR    480
QNVWEAFHSE MTGSGPAPAK YDYKSMSLKQ MSGNVVTPAA AFGHYLWGNG EERYVNLPDV    540
GLKITPQQIP ELMNIVNSGV TGNIPVDLNF NHNTYDSGGV IPASYLGNVS LRTIGSLNIQ    600
```

```
NSGEWTYNGV VRAYNDYYDF NLGDYRGAIA ESLTYLGAQF SGKPYHIAMP GEINISGAGH  660
R                                                                 661

SEQ ID NO: 28          moltype = DNA  length = 1986
FEATURE                Location/Qualifiers
source                 1..1986
                       mol_type = other DNA
                       organism = synthetic construct
SEQUENCE: 28
atgcctgaag aaacattgac tgtcgtaggt ggtggtaata acagctgtaa tgttagctgg  60
ggtggtggca atggtaacaa cggtggtgct ggctattctg gtaaatacgg tggtactagc  120
tatgaaggtg caactagtat gttgaagttg aatgaccgtg ttttaattca gctttatctt  180
tgcaatccgc ttaacccaga ttatattgga gcaccttggg cagtgataaa agatgcagaa  240
tcaattatca gagctaacag agataaagca ggaaagttca aggctaatat tcagaactgg  300
aaaacaagcg gtacaggttc tttaggtagc cctgtagttg ggaaatctta tagctcaggt  360
gatgtagata cttattcggt tagcttcgga aaagaaaat acaatgtcct gtataaccgt  420
aaaaaagact ctttttactac agcttatgtc gatggcggcg caaataaacc tgagcatagc  480
atgaaggatc aggctattgc cgttgttaaa ctttaccttc tcaacgaaag tcaggcatcg  540
gtaatcgata ctacatcggg aattattact gactctggta aaactcttag cgggaaatta  600
ggtgataaat acaacactct ggcgaaagaa gctgctgaca atataaaaaa cttccagggt  660
aagaaactcc gcagttttaa tgatgctatg gcatctatta tgaactagc taacaatcca  720
aagatgaagt taagtcaggc ggataaaaca gtcgtttcta atgccctcaa acaaatggat  780
ttgtcagcac tagctgaccg attcaaaggg ttagagaaag cctttacttg gggtgatcga  840
cttcttaaag ccgagaaat cagagaaggt gttgttactg gtattaccac aggggactgg  900
caaaagctgg cgtttgaggt tgaagctatg tacctcagtg gtgttgctgg cgccgtagcg  960
ttagggatta ctactgccat gattagcaca gtcgcagtca ctttgtcact tccagctgta  1020
gctgtctctg cgcttactgt tgtgtccgtc attggcatct ctattctcac atcttatatc  1080
gatgctgata aggccaaagc actgaataat gcagtgcttg gcttatttaa aggctccgga  1140
tcggcttctg ggagcgagac catggttgtt gttgcgccgc cgaccggttt tgagccggcg  1200
ggttacggtg gtggcctgtt cagcccgagc accccgacca acagcccgag ccagggtcaa  1260
atcttcctgc aagtgaccct gccgtactat cagagcgcga agttttgcca agacagcatg  1320
gcgtggctgg cgcagtacgt taaaaacccac ggcgcgaccg atccgctgac catccaagtg  1380
gttgcgaaca acattcgtta cttcctgaac gcggacacca acctgtgcca caacccgcgt  1440
cagaacgtgt gggaggcgtt tcacagcgaa atgaccggta gcggtccggc gccggcgaag  1500
tacgattata aaagcatgag cctgaagcaa atgagcggta acgtggttac cccggcgggt  1560
gcgtttggtc actacctgtg gggtaacggc gaggaacgtt atgtgaacct gccggacgtt  1620
ggtctgaaaa tcacccgca gcaaattccg gagctgatga acatcgtgaa cagcggtgtt  1680
accggcaaca ttccggttga cctgaacttt aaccacaaca cctacgatag cggtggcgtg  1740
atcccggcga gctatctggg taacgttagc ctgcgtacca tcggcagcct gaacattcaa  1800
aacagcggcg agtggaccta caacggcgtg gttcgtgcgt ataacgacta ctatgatttc  1860
aacctgggtg attaccgtgg cgcgattgcg gaaagcctga cctatctggg cgcgcaattt  1920
agcggtaagc cgtatcacat tgcgatgccg ggcgaaatca acattagcgg tgcgggtcat  1980
cgttaa                                                             1986

SEQ ID NO: 29          moltype = AA  length = 643
FEATURE                Location/Qualifiers
source                 1..643
                       mol_type = protein
                       organism = synthetic construct
SEQUENCE: 29
MGPGNSGLGH NGGQASGNVN GTSGKGGPSS GGGTDPNSGP GWGTTHTPNG DIHNYNPGEF  60
GNGGSKPGGN GGNSGNHSGS SGGGQSSATA MAFGLPALAT PGAEGLALSV SGDALSAAVA  120
DVLAALKGPF KFGLWGIAIY GVLPSEIAKD DPKMMSKIVT SLPADTVTET PVSSLPLDQA  180
TVSVTKRVAD IVKDERQHIA VVTGRPMSVP VVDAKPTKRP GVFSVSIPGL PSLQVSVPKG  240
VPAAKAPPKG IIAEKGDSRP AGFTAGGNSR EAVIRFPKES GQKPVYVSVT DVLTPAQVKQ  300
RLEEEKRRQQ AWDAAHPEEG LKREYDKAKA ELDAEDKNIA TLNSRIASTE KAIPGARAAV  360
QEADKKVKEA EANKDDFVTY NPPHEYGSGW QDQVRYLDKD IQNQNEKLKA AQTSLNEMNE  420
SLSRDKAALS GAMESRKQKE KKAKDAENKL NEEKKKPRKG TKDYGHDYFP DPKTEDIKGL  480
GELKEGKPKT PKQGGGGKRA RWYGDKKRKI YEWDSQHGEL EGYRASDGEH LGAFDPKTGK  540
QVKGPDPKRN IKKYLEVSMG LKLNLTWFDK KTEEFKGGEY SKDFGDDGSV IESLGMPLKD  600
NINNGWFDVE KSWVSILQPH FKNVIDISKF DYFVSFDYRD GNW                    643

SEQ ID NO: 30          moltype = DNA  length = 1935
FEATURE                Location/Qualifiers
source                 1..1935
                       mol_type = other DNA
                       organism = synthetic construct
SEQUENCE: 30
atgggtccgg gtaattcagg tctgggacac aatggtggtc aggccagtgg gaatgtgaac  60
ggtacatcag gtaaaggtgg cccttcatca ggtggtggta cggatccaaa cagcgggccg  120
ggctggggta cgacgcatac acctaacggg gatattcata ctataaaccc gggggagttt  180
ggtaacggcg ggagtaaaac cggtggtaat ggcggtaaca cggcaatca tagcgggagc  240
tctggtggcg gacagtcttc ggccaccgcg atggccttcg gtctgcctgc cttggccact  300
ccggggctg aaggactggc tttatccgtt tccggcgatg cgttgtcggc cgctgttgct  360
gatgtgctgg ctgccctgaa aggtccgttt aagtttggtc tgtggggat tgcgatttac  420
ggagtgctgc cttctgagat agcaaaagat gatccgaaaa tgatgtcaaa atcgtgacg  480
tcattgccca cagacacggt aacgagacg ccggtcagct ccctgccgct ggaccaggcg  540
acggtcagcg tcactaaacg tgtggcggat attgtgaagg acgagcggca gcatattgcg  600
gttgtcaccg gccggccaat gagtgttcct gtggtggatg cgaaaccgac aaaacgtccg  660
```

```
ggggtattca gtgtgtcgat tccgggtctc ccgtctctgc aggtgagcgt acctaaaggt   720
gttccggccg cgaaagcccc gccaaaaggc attattgctg aaaaaggtga ttcacgtccg   780
gctggtttta cggccggtgg taactcccgt gaagccgtta ttcgtttccc gaaagagagc   840
ggacagaaac cggtctatgt gtcggtgacg gatgttctta ctccggcaca ggtaaaacag   900
cgtctggagg aagaaaagcg tcgccagcag gcatgggacg ctgctcaccc ggaagagggg   960
ctgaaaagag agtatgataa agcgaaagct gagctggatg ctgaagataa aaatattgcg  1020
accttaaaca gtcgcattgc atcgacagag aaggcgatcc ccggtgcaag ggctgctgtt  1080
caggaagcca ataaaaaggt aaaagaggca gaggcaaata aagatgattt tgtgacttat  1140
aacccgcctc atgaatatgg ctccgggtgg caggatcagg ttcgctatct tgataaggat  1200
attcagaatc agaatgagaa attaaaagct gcccagacat ctttaaacga aatgaatgaa  1260
tccttatcca gggataaggc tgcgcttttcc ggggcgatgg agagccggaa acaaaaggag  1320
aaaaaagcga aggatgcaga aaataaatta aatgaggaaa agaaaaaacc tcgtaaggga  1380
actaaagatt acggccatga ttattttcct gatcccaaga ctgaagatat taaggggttg  1440
ggagagttga aagagggtaa acctaaaacc cctaaacaag gtggtggtgg taagcgggcc  1500
cgatggtatg gtgataaaaa gcgtaaaatt tatgaatggg attcccagca cggtgagctt  1560
gaaggggtacc gcgccagtga tggcgaacac ctcgggggcat tcgatccaaa aacgggtaag  1620
caggttaaag ggccggatcc aaaacgaaac attaaaaaat atctttaaga ggtaagtatg  1680
ggacttaaat taaatttaac ctggtttgat aagaaaaccg aagagtttaa aggtggtgaa  1740
tactcaaaag acttcggtga tgatggttct gtcattgaaa gtctggggat gcctttaaag  1800
gataatatta ataatggttg gtttgatgtt gaaaaatcat gggtttcgat attacagcca  1860
cactttaaaa atgtaatcga tattagtaaa tttgattact ttgtatcatt tgattatcgg  1920
gatggtaact ggtaa                                                   1935
```

```
SEQ ID NO: 31              moltype = AA  length = 625
FEATURE                    Location/Qualifiers
source                     1..625
                           mol_type = protein
                           organism = synthetic construct
SEQUENCE: 31
MNGTSGKGGP SSGGGTDPNS GPGWGTTHTP NGDIHNYNPG EFGNGGSKPG GNGGNSGNHS  60
GSSGGGGQSSA TAMAFGLPAL ATPGAEGLAL SVSGDALSAA VADVLAALKG PFKFGLWGIA  120
IYGVLPSEIA KDDPKMMSKI VTSLPADTVT ETPVSSLPLD QATVSVTKRV ADIVKDERQH  180
IAVVTGRPMS VPVVDAKPTK RPGVFSVSIP GLPSLQVSVP KGVPAAKAPP KGIIAEKGDS  240
RPAGFTAGGN SREAVIRFPK ESGQKPVYVS VTDVLTPAQV KQRLEEEKRR QQAWDAAHPE  300
EGLKREYDKA KAELDAEDKN IATLNSRIAS TEKAIPGARA AVQEADKKVK EAEANKDDFV  360
TYNPPHEYGS GWQDQVRYLD KDIQNQNEKL KAAQTSLNEM NESLSRDKAA LSGAMESRKQ  420
KEKKAKDAEN KLNEEKKKPR KGTKDYGHDY FPDPKTEDIK GLGELKEGKP KTPKQGGGGK  480
RARWYGDKKR KIYEWDSQHG ELEGYRASDG EHLGAFDPKT GKQVKGPDPK RNIKKYLEVS  540
MGLKLNLTWF DKKTEEFKGG EYSKDFGDDG SVIESLGMPL KDNINNGWFD VEKSWVSILQ  600
PHFKNVIDIS KFDYFVSFDY RDGNW                                        625
```

```
SEQ ID NO: 32              moltype = DNA  length = 1881
FEATURE                    Location/Qualifiers
source                     1..1881
                           mol_type = other DNA
                           organism = synthetic construct
SEQUENCE: 32
atgaacggta catcaggtaa aggtggccct tcatcaggtg gtggtacgga tccaaacagc   60
gggccgggct ggggtacgac gcatacacct aacggggata ttcataacta taacccgggg   120
gagtttggta acggcgggag taaacccggt ggtaatggcg gtaacagcgg caatcatagc   180
gggagctctg gtggcggaca gtcttcggcc accgcgatgg ccttcggtct gcctgccttg   240
gccactccgg gggctgaagg actggcttta tccgtttccg gcgatgcgtt gtcggccgct   300
gttgctgatg tgctggctgc cctgaaaggt ccgtttaagt ttggtctgtg ggggattgcg   360
atttacggag tgctgccttc tgagatagca aaagatgatc cgaaaatgat gtcaaaaatc   420
gtgacgtcat tgccggcaga cacggtaacg gagacgccgg tcagctccct gccgctggac   480
caggcgacgg tcagcgtcac taaacgtgtg gcggatattg tgaaggacga gcggcagcat   540
attgcggttg tcaccggccg gccaatgagt gttcctgtgg tggatgcgaa accgacaaaa   600
cgtccggggg tattcagtgt gtcgattccg ggtctcccgt ctctgcaggt gagcgtacct   660
aaaggtgttc cggccgcgaa agcccccgcca aaaggcatta ttgctgaaaa aggtgattca   720
cgtccgggtg gttttacggc cggtggtaac tcccgtgaag ccgttattcg tttcccgaaa   780
gagagcggac agaaaccggt ctatgtgtcg gtgacggatg ttcttactcc ggcacaggta   840
aaacagcgtc tggaggaaga aaagcgtcgc cagcaggcat gggacgctgc tcacccggaa   900
gaggggctga aaagagagta tgataaagcg aaagctgagc tggatgctga agataaaaat   960
attgcgacct taaacagtcg cattgcatcg acagagaagg cgatcccccgg tgcaagggct  1020
gctgttcagg aagccgataa aaaggtaaaa gaggcagagg caaataaaga tgattttgtg  1080
acttataacc cgcctcatga atatggctcc gggtggcagg atcaggttcg ctatcttgat  1140
aaggatattc agaatcagaa tgagaaatta aaagctgccc agacatcttt aaacgaaatg  1200
aatgaatcct tatccaggga taaggctgcg cttttccgggg cgatggagag ccggaaacaa  1260
aaggagaaaa aagcgaagga tgcagaaaat aaattaaatg aggaaaagaa aaaacctcgt  1320
aagggaacta agattacggg ccatgattat tttcctgatc ccaagactga agatattaag  1380
gggtgggggag agttgaaaga gggtaaacct aaaaccccta acaaggtggt ggtggtaag  1440
cgggcccgat ggtatggtga taaaaagcgt aaaatttatg aatgggattc ccagcacggt  1500
gagcttgaag gtaccgcgc cagtgatggc gaacacctcg gggcattcga tccaaaaacg  1560
ggtaagcagg ttaaagggcc ggatccaaaa cgaaacatta aaaaatatct taagaggtaa  1620
agtatgggac ttaaattaaa tttaacctgg tttgataaga aaccgaaga gtttaaaggt  1680
ggtgaatact caaagacttt cggtgatgat ggttctgtca ttgaaagtct ggggatgcct  1740
ttaaaggata tattaataa tggttggttt gatgttgaaa aatcatgggt ttcgatatta  1800
cagccacact ttaaaaatgt aatcgatatt agtaaatttg attactttgt atcatttgat  1860
tatcgggatg gtaactggta a                                           1881
```

-continued

```
SEQ ID NO: 33          moltype = AA   length = 470
FEATURE                Location/Qualifiers
source                 1..470
                       mol_type = protein
                       organism = synthetic construct
SEQUENCE: 33
MPEETLTVVG GGNNSCNVSW GGGNGNNGGA GYSGKYGGTS YEGATSMLKL NDRVLIQLYL  60
CNPLNPDYIG APWGSDKDAE SIIRANRDKA GKFKANIQNW KTSGTGSLGS PVVGKSYSSG  120
DVDTYSVSFG KEKYNVLYNR KKDSFTTAYV DGGANKPEHS QGQIFLQVTL PYYQSAKFCQ  180
DSMAWLAQYV KTHGATDPLT IQVVANNIRY FLNADTNLCH NPRQNVWEAF HSEMTGSGPA  240
PAKYDYKSMS LKQMKDQAIA VVKLYLLNES QASVIDTTSG IITDSGKTLS GKLGDKYNTL  300
AKEAADNIKN FQGKKLRSFN DAMASINELA NNPKMKLSQA DKTVVSNALK QMDLSALADR  360
FKGLEKAFTW GDRLLKAEKI REGVVTGITT GDWQKLAFEV EAMYLSGVAG AVALGITTAM  420
ISTVAVALSL PAVAVSALTV VSVIGISILT SYIDADKAKA LNNAVLGLFK            470

SEQ ID NO: 34          moltype = DNA   length = 1413
FEATURE                Location/Qualifiers
source                 1..1413
                       mol_type = other DNA
                       organism = synthetic construct
SEQUENCE: 34
atgcctgaag aaacattgac tgtcgtaggt ggtggtaata acagctgtaa tgttagctgg  60
ggtggtggca atggtaacaa cggtggtgct ggctattctg gtaaatacgg tggtactagc  120
tatgaaggtg caactagtat gttgaagttg aatgaccgtg tttttaattca gctttatctt  180
tgcaatccgc ttaacccaga ttatattgga gcaccttggg gcagtgataa agatgcagaa  240
tcaattatca gagctaacag agataaagca ggaaagttca aggctaatat tcagaactgg  300
aaaacaagcg gtacaggttc tttaggtagc cctgtagttg ggaaatctta tagctcaggt  360
gatgtagata cttattcggt tagcttcgga aaagaaaaat acaatgtcct gtataaccgt  420
aaaaaagact cttttactac agcttatgtc gatggcggcg caaataaacc tgagcatagc  480
cagggtcaaa tcttcctgca agtgaccctg ccgtactatc agagcgcgaa gttttgccaa  540
gacagcatgg cgtggctggc gcagtacgtt aaaacccacg gcgcgaccga tccgctgacc  600
atccaagtgg ttgcgaacaa cattcgttac ttcctgaacg cggacaccaa cctgtgccac  660
aacccgcgtc agaacgtgtg ggaggcgttt cacagcgaaa tgaccggtag cggtccggcg  720
ccggcgaagt acgattataa aagcatgagc ctgaagcaaa tgaaggatca ggctattgcc  780
gttgttaaac tttaccttct caacgaaagt caggcatcgg taatcgatac tacatcggga  840
attattactg actctggtaa aactcttagc gggaaattag gtgataaata caacactctg  900
gcgaaagaag ctgctgacaa tataaaaaac ttccaggggta agaaactccg cagttttaat  960
gatgctatgg catctattaa tgaactagct aacaatccaa agatgaagtt aagtcaggcg  1020
gataaaacag tcgtttctaa tgccctcaaa caaatggatt tgtcagcact agctgaccga  1080
ttcaaagggt tagagaaagc ctttacttgg ggtgatcgac ttcttaaagc cgagaaaatc  1140
agagaaggtg ttgttactgg tattaccaca ggggactggc aaaagctggc gtttgaggtt  1200
gaagctatgt acctcagtgg tgttgctggc gccgtaagcg tagggattac tactgccatg  1260
attagcacag tcgcagtcgc tttgtcactt ccagctgtag ctgtctctgc gcttactgtt  1320
gtgtccgtca ttggcatctc tattctcaca tcttatatcg atgctgataa ggccaaagca  1380
ctgaataatg cagtgcttgg cttatttaaa taa                               1413

SEQ ID NO: 35          moltype = AA   length = 687
FEATURE                Location/Qualifiers
source                 1..687
                       mol_type = protein
                       organism = synthetic construct
SEQUENCE: 35
MSGGDGRGPG NSGLGHNGGQ ASGNVNGTSG KGGPSSGGGT DPNSGPGWGT THTPNGDIHN  60
YNPGEFGNGG SKPGGNGGNS GNHSGSSGGG QSSATAMAFG LPALATPGAE GLALSVSGDA  120
LSAAVADVLA ALKGPFKFGL WGIAIYGVLP SEIAKDDPKM MSKIVTSLPA DTVTETPVSS  180
LPLDQATVSV TKRVADIVKD ERQHIAVVTG RPMSVPVVDA KPTKRPGVFS VSIPGLPSLQ  240
VSVPKGVPAA KAPPKGIIAE KGDSRPAGFT AGGNSREAVI RFPKESGQKP VYVSVTDVLT  300
PAQVKQRLEE EKRRQQAWDA AHPEEGLKRE YDKAKAELDA DKNIATLNS RIASTEKAIP  360
GARAAVQEAD KKVKEAEANK DDFVTYNPPH EYGSGWQDQV RYLDKDIQNQ NEKLKAAQTS  420
LNEMNESLSR DKAALSGAME SRKQKEKKAK DAENKLNEEK EAAAKEAAAK MKDQAIAVVK  480
LYLLNESQAS VIDTTSGIIT DSGKTLSGKL GDKYNTLAKE AADNIKNFQG KKLRSFNDAM  540
ASINELANNP KMKLSQADKT VVSNALKQMD LSALADRFKG LEKAFTWGDR LLKAEKIREG  600
VVTGITTGDW QKLAFEVEAM YLSGVAGAVA LGITTAMIST VAVALSLPAV AVSALTVVSV  660
IGISILTSYI DADKAKALNN AVLGLFK                                      687

SEQ ID NO: 36          moltype = DNA   length = 2064
FEATURE                Location/Qualifiers
source                 1..2064
                       mol_type = other DNA
                       organism = synthetic construct
SEQUENCE: 36
atgagtggtg gagacggacg aggtccgggt aattcaggtc tgggacacaa tggtggtcag  60
gccagtggga atgtgaacgg tacatcaggt aaaggtggcc cttcatcagg tggtggtacg  120
gatccaaaca gcgggccggg ctggggtacg acgcatacac ctaacgggga tattcataac  180
tataaccccg gggagtttgg taacggcggg agtaaacccg gtggtaatgg cggtaacagc  240
ggcaatcata gcgggagctc tggtggcgga cagtcttcgg ccaccgcgat ggccttcggt  300
ctgcctgcct ggccactcc gggggctgaa ggactggctt atccgtttc cggcgatgcg  360
ttgtcggccg ctgttgctga tgtgctggct gccctgaaag tccgtttaa gtttggtctg  420
```

-continued

```
tgggggattg cgatttacgg agtgctgcct tctgagatag caaaagatga tccgaaaatg    480
atgtcaaaaa tcgtgacgtc attgccggca gacacggtaa cggagacgcc ggtcagctcc    540
ctgccgctgg accaggcgac ggtcagcgtc actaaacgtg tggcggatat tgtgaaggac    600
gagcggcagc atattgcggt tgtcaccggc cggccaatga gtgttcctgt ggtggatgcg    660
aaaccgacaa aacgtccggg ggtattcagt gtgtcgattc cgggtctccc gtctctgcag    720
gtgagcgtac ctaaaggtgt tccggccgcg aaagccccgc caaaaggcat tattgctgaa    780
aaaggtgatt cacgtccggc tggtttttacg gccggtggta actcccgtga agccgttatt    840
cgtttcccga aagagagcgg acagaaaccg gtctatgtgt cggtgacgga tgttcttact    900
ccggcacagg taaaacagcg tctggaggaa gaaaagcgtc gccagcaggc atgggacgct    960
gctcacccgg aagaggggct gaaaagagag tatgataaag cgaaagctga gctggatgct   1020
gaagataaaa atattgcgac cttaaacagt cgcattgcat cgacagagaa ggcgatcccc   1080
ggtgcaaggg ctgctgttca ggaagccgat aaaaaggtaa aagaggcaga ggcaaataaa   1140
gatgattttg tgacttataa cccgcctcat gaatatggct ccgggtggca ggatcaggtt   1200
cgctatcttg ataaggatat tcagaatcag aatgagaaat taaaagctgc ccagacatct   1260
ttaaacgaaa tgaatgaatc cttatccagg gataaggctg cgctttccgg ggcgatggag   1320
agccggaaac aaaaggagaa aaaagcgaag gatgcagaaa ataaattaaa tgaggaaaag   1380
gaagccgctg ccaaggaggc ggccgctaaa atgaaggatc aggctattgc cgttgttaaa   1440
ctttaccttc tcaacgaaag tcaggcatcg gtaatcgaat ctcatcgg aattattact   1500
gactctggta aaactcttag cgggaaatta ggtgataaat acaacactct ggcgaaagaa   1560
gctgctgaca atataaaaaa cttccagggt aagaaactcc gcagtttaa tgatgctatg   1620
gcatctatta tgaactagc taacaatcca aagatgaagt taagtcaggc ggataaaaca   1680
gtcgtttcta atgccctcaa acaaatggat ttgtcagcac cagctgacc attcaaaggg   1740
ttagagaaag cctttacttg gggtgatcga cttcttaaag ccgagaaaat cagagaaggt   1800
gttgttactg gtattaccac aggggactgg caaaagctgg cgtttgaggt tgaagctatg   1860
tacctcagtg gtgttgctgg cgccgtagcg ttagggatta ctactgccat gattagcaca   1920
gtcgcagtcg cttttgtcact tccagctgta gctgtctctg cgcttactgt tgtgtccgtc   1980
attggcatct ctattctcac atcttatatc gatgctgata aggccaaagc actgaataat   2040
gcagtgcttg gcttatttaa ataa                                          2064
```

```
SEQ ID NO: 37          moltype = AA   length = 348
FEATURE                Location/Qualifiers
source                 1..348
                       mol_type = protein
                       organism = synthetic construct
SEQUENCE: 37
MPEETLTVVG GGNNSCNVSW GGGNGNNGGA GYSGKYGGTP SQGQIFLQVT LPYYQSAKFC    60
QDSMAWLAQY VKTHGATDPL TIQVVANNIR YFLNADTNLC HNPRQNVWEA FHSEMTGSGP   120
APAKYDYKSM SLKLQAIAVV KLYLLNESQA SVIDTTSGII TDSGKTLSGK LGDKYNTLAK   180
EAADNIKNFQ GKKLRSFNDA MASINELANN PKMKLSQADK TVVSNALKQM DLSALADRFK   240
GLEKAFTWGD RLLKAEKIRE GVVTGITTGD WQKLAFEVEA MYLSGVAGAV ALGITTAMIS   300
TVAVALSLPA VAVSALTVVS VIGISILTSY IDADKAKALN NAVLGLFK                348
```

```
SEQ ID NO: 38          moltype = DNA   length = 1047
FEATURE                Location/Qualifiers
source                 1..1047
                       mol_type = other DNA
                       organism = synthetic construct
SEQUENCE: 38
atgcctgaag aaacattgac tgtcgtaggt ggtggtaata acagctgtaa tgttagctgg    60
ggtggtggca atggtaacaa cggtggtgct ggctattctg gtaaatacgg tggtaccccg   120
agccagggtc aaatcttcct gcaagtgacc ctgccgtact atcagagcgc gaagttttgc   180
caagacagca tggcgtggct ggcgcagtac gttaaaaccc acggcgcgac cgatccgctg   240
accatccaag tggttgcgaa caacattcgt tacttcctga acgcggacac caacctgtgc   300
cacaacccgc gtcagaacgt gtgggaggcg tttcacagcg aaatgaccgg tagcggtccg   360
gcgccggcga agtacgatta taaaagcatg agcctgaagc ttcaggctat tgccgttgtt   420
aaactttacc ttctcaacga aagtcaggca tcggtaatcg atactacatc gggaattatt   480
actgactctg gtaaaactct tagcgggaaa ttaggtgata atacaacac tctggcgaaa   540
gaagctgctg acaatataaa aaacttccag ggtaagaaac tccgcagttt taatgatgct   600
atggcatcta ttaatgaact agctaacaat ccaaagatga gttaagtca ggcggataaa   660
acagtcgttt ctaatgccct caaacaaatg gatttgtcag cactagctga ccgattcaaa   720
gggttagaga aagccttac ttgggggtgat cgacttctta aagccgagaa aatcagagaa   780
ggtgttgtta ctggtattac acaggggac tggcaaaagc tggcgtttga ggttgaagct   840
atgtacctca gtggtgttgc tggcgccgta gcgttaggga ttactactgc catgattagc   900
acagtcgcag tcgctttgtc acttccagct gtagctgtct ctgcgcttac tgttgtgtcc   960
gtcattggca tctctattct cacatcttat atcgatgctg ataaggccaa agcactgaat   1020
aatgcagtgc ttggcttatt taaataa                                        1047
```

```
SEQ ID NO: 39          moltype = AA   length = 307
FEATURE                Location/Qualifiers
source                 1..307
                       mol_type = protein
                       organism = synthetic construct
SEQUENCE: 39
MSETMVVAP PTGFEPAGYG GGLFSPSTPN GTSYEGATSM LKLNDRVLIQ LYLCNPLNPD     60
YIGAPWGSDK DAESIIRANR DKAGKFKANI QNWKTSGTGS LGSPVVGKSY SSGDVDTYSV   120
SFGKEKYNVL YNRKKDSFTT AYVDGGANKP EHSMKLMSGN VVTPAAAFGH YLWGNGEERY   180
VNLPDVGLKI TPQQIPELMN IVNSGVTGNI PVDLNFNHNT YDSGGVIPAS YLGNVSLRTI   240
GSLNIQNSGE WTYNGVVRAY NDYYDFNLGD YRGAIAESLT YLGAQFSGKP YHIAMPGEIN   300
ISGAGHR                                                              307
```

-continued

```
SEQ ID NO: 40              moltype = DNA  length = 924
FEATURE                    Location/Qualifiers
source                     1..924
                           mol_type = other DNA
                           organism = synthetic construct
SEQUENCE: 40
atgagcgaga ccatggttgt tgttgcgccg ccgaccggtt ttgagccggc gggttacggt  60
ggtggcctgt tcagcccgag caccccgaac ggtaccagct atgaaggtgc aactagtatg  120
ttgaagttga atgaccgtgt ttttaattcag ctttatcttt gcaatccgct taacccagat  180
tatattggag caccttgggg cagtgataaa gatgcagaat caattatcag agctaacaga  240
gataaagcag gaaagttcaa ggctaatatt cagaactgga aaacaagcgg tacaggttct  300
ttaggtagcc ctgtagttgg gaaatcttat agctcaggtg atgtagatac ttattcggtt  360
agcttcggaa aagaaaaata caatgtcctg tataaccgta aaaaagactc ttttactaca  420
gcttatgtcg atggcggcgc aaataaacct gagcatagca tgaagcttat gagcggtaac  480
gtggttaccc cggcggcggc gtttggtcac tacctgtggg gtaacggcga ggaacgttat  540
gtgaacctgc cggacgttgg tctgaaaatc accccgcagc aaattccgga gctgatgaac  600
atcgtgaaca gcggtgttac cggcaacatt ccggttgacc tgaactttaa ccacaacacc  660
tacgatagcg gtggcgtgat cccggcgagc tatctgggta acgttagcct cgctaccatc  720
ggcagcctga cattcagaa cagcggcgag tggacctaca acggcgtggt tcgtgcgtat  780
aacgactact atgatttcaa cctgggtgat taccgtggcg cgattgcgga aagcctgacc  840
tatctgggcg cgcaatttag cggtaagccg tatcacattg cgatgccggg cgaaatcaac  900
attagcggtg cgggtcatcg ttaa                                          924

SEQ ID NO: 41              moltype = AA  length = 793
FEATURE                    Location/Qualifiers
source                     1..793
                           mol_type = protein
                           organism = synthetic construct
SEQUENCE: 41
MPEETLTVVG GGNNSCNVSW GGGNGNNGGA GYSGKYGGTS YEGATSMLKL NDRVLIQLYL  60
CNPLNPDYIG APWGSDKDAE SIIRANRDKA GKFKANIQNW KTSGTGSLGS PVVGKSYSSG  120
DVDTYSVSFG KEKYNVLYNR KKDSFTTAYV DGGANKPEHE AAAKEAAAKN GTSGKGGPSS  180
GGGTDPNSGP GWGTTHTPNG DIHNYNPGEF GNGGSKPGGN GNSGNHSGS SGGGQSSATA  240
MAFGLPALAT PGAEGLALSV SGDALSAAVA DVLAALKGPF KFGLWGIAIY GVLPSEIAKD  300
DPKMMSKIVT SLPADTVTET PVSSLPLDQA TVSVTKRVAD IVKDERQHIA VVTGRPMSVP  360
VVDAKPTKRP GVFSVSIPGL PSLQVSVPKG VPAAKAPPKG IIAEKGDSRP AGFTAGGNSR  420
EAVIRFPKES GQKPVYVSVT DVLTPAQVKQ RLEEEKRRQQ AWDAAHPEEG LKREYDKAKA  480
ELDAEDKNIA TLNSRIASTE KAIPGARAAV QEADKKVKEA EANKDDFVTY NPPHEYGSGW  540
QDQVRYLDKD IQNQNEKLKA AQTSLNEMNE SLSRDKAALS GAMESRKQKE KKAKDAENKL  600
NEEKKKPRKG TKDYGHDYFP DPKTEDIKGL GELKEGKPKT PKQGGGGKRA RWYGDKKRKI  660
YEWDSQHGEL EGYRASDGEH LGAFDPKTGK QVKGPDPKRN IKKYLEVSMG LKLNLTWFDK  720
KTEEFKGGEY SKDFGDDGSV IESLGMPLKD NINNGWFDVE KSWVSILQPH FKNVIDISKF  780
DYFVSFDYRD GNW                                                      793

SEQ ID NO: 42              moltype = DNA  length = 2385
FEATURE                    Location/Qualifiers
source                     1..2385
                           mol_type = other DNA
                           organism = synthetic construct
SEQUENCE: 42
atgcctgaag aaacattgac tgtcgtaggt ggtggtaata acagctgtaa tgttagctgg  60
ggtggtggca atggtaacaa cggtggtgct ggctattctg gtaaatacgg tggtactagc  120
tatgaaggtg caactagtat gttgaagttg aatgaccgtg ttttaattca gctttatctt  180
tgcaatccgc ttaacccaga ttatattgga gcaccttggg cagtgataaa gatgcagaa  240
tcaattatca gagctaacag agataaagca ggaaagttca aggctaatat tcagaactgg  300
aaaacaagcg gtacaggttc tttaggtagc cctgtagttg ggaaatctta tagctcaggt  360
gatgtagata cttattcggt tagcttcgga aagaaaaat acaatgtcct gtataaccgt  420
aaaaaagact cttttactac agcttatgtc gatggcggca aataaaacc tgagcatgaa  480
gccgctgcca aggaggcggc cgctaaaaac ggtacatcag gtaaaggtgg cccttcatca  540
ggtggtggta cggatccaaa cagcgggccg ggctggggta cgacgcatac acctaacggg  600
gatattcata actataaccc ggggggagttt ggtaacggcg ggagtaaacc cggtggtaat  660
ggcggtaaca gcggcaatca tagcgggagc tctggtggcg acagtcttc ggccaccgcg  720
atggccttcg gtctgcctgc cttggccact ccgggggcg aaggactggc tttatccgtt  780
tccggcgatg cgttgtcggc cgctgttgct gatgtgctgg ctgccctgaa aggtccgttt  840
aagtttggtc tgtgggggat tgcgatttac ggagtgctgc cttctgagat agcaaaagat  900
gatccgaaaa tgatgtcaaa aatcgtgacg tcattgccgg cagacacggt aacggagacg  960
ccggtcagct ccctgccgct ggaccaggcg acggtcagcg tcactaaacg tgtggcggat  1020
attgtgaagg acgagcggca gcatattgcg gttgtcaccg gccggccaat gagtgttcct  1080
gtggtggatg cgaaaccgac aaaacgtccg ggggtattca gtgtgtcgat ccgggtctc  1140
ccgtctctgc aggtgagcgt acctaaaggt gttccggccg cgaaagcccc gccaaaaggc  1200
attattgcta aaaaaggtga ttcacgtccg gctggtttta cggccggtgg taactcccgt  1260
gaagccgtta ttcgtttccc gaaagagagc ggacagaaac cggtctatgt gtcggtacg  1320
gatgttctta ctccggcaca ggtaaaacag cgtctggagg aagaaaaacg tcgccaacag  1380
gcatgggacg ctgctcaccc ggaagagggg ctgaaaagag agtatgataa agcgaaagct  1440
gagctggatg ctgaagataa aaatattgcg accttaaaca gtcgcattgc atcgacagag  1500
aaggcgatcc ccggtgcaag ggctgctgtt caggaagccg ataaaaaggt aaaagaggca  1560
gaggcaaata aagatgattt tgtgacttat aacccgcctc atgaatatgg ctccgggtgg  1620
caggatcagg ttcgctatct tgataaggat attcagaatc agaatgagaa attaaaagct  1680
```

-continued

```
gcccagacat ctttaaacga aatgaatgaa tccttatcca gggataaggc tgcgcctttc  1740
ggggcgatgg agagccggaa acaaaaggag aaaaaagcga aggatgcaga aaataaatta  1800
aatgaggaaa agaaaaaacc tcgtaaggga actaaagatt acggccatga ttattttcct  1860
gatcccaaga ctgaagatat taaggggttg ggagagttga aagagggtaa acctaaaacc  1920
cctaaacaag gtggtggtgg taagcgggcc cgatggtatg gtgataaaaa gcgtaaaatt  1980
tatgaatggg attcccagca cggtgagctt gaagggtacc gcgccagtga tggcgaacac  2040
ctcgggggcat tcgatccaaa aacgggtaag caggttaaag ggccggatcc aaaacgaaac  2100
attaaaaaat atctttaaga ggtaagtatg ggacttaaat taaatttaac ctggtttgat  2160
aagaaaaccg aagagtttaa aggtggtgaa tactcaaaag acttcggtga tgatggttct  2220
gtcattgaaa gtctggggat gccttttaaag gataatatta ataatggttg gtttgatgtt  2280
gaaaaatcat gggtttcgat attacagcca cactttaaaa atgtaatcga tattagtaaa  2340
tttgattact ttgtatcatt tgattatcgg gatggtaact ggtaa            2385
```

```
SEQ ID NO: 43          moltype = AA  length = 382
FEATURE                Location/Qualifiers
source                 1..382
                       mol_type = protein
                       organism = synthetic construct
SEQUENCE: 43
MSDTMIVVAT PTPGFSYASG LTYGGGAFAG APANGPSEGQ IFFQTVLPAY QSPNLCIGQL   60
AWMTDYINKN GVGNPKTWEV ISQNVLIFCS ADTALVLNPR IAVYDGFHKT KWAPAKFNFK  120
TQSQEKFSGN VTTPIAAFGH YLWGEGKPRT VDLSSEAAAK EAAAKMKDQA IAVVKLYLLN  180
ESQASVIDTT SGIITDSGKT LSGKLGDKYN TLAKEAADNI KNFQGKKLRS FNDAMASINE  240
LANNPKMKLS QADKTVVSNA LKQMDLSALA DRFKGLEKAF TWGDRLLKAE KIREGVVTGI  300
TTGDWQKLAF EVEAMYLSGV AGAVALGITT AMISTVAVAL SLPAVAVSAL TVVSVIGISI  360
LTSYIDADKA KALNNAVLGL FK                                          382
```

```
SEQ ID NO: 44          moltype = DNA  length = 1149
FEATURE                Location/Qualifiers
source                 1..1149
                       mol_type = other DNA
                       organism = synthetic construct
SEQUENCE: 44
atgtcagata caatgatagt agttgctact ccgaccccgg gttttagcta cgcgagcggc   60
ttgacgtacg gcggtggtgc gtttgcgggt gcgcctgcga acggtccgtc ggaaggccaa  120
atctttttcc agaccgttct gccggcgtat caatccccga atctgtgtat tggtcaactg  180
gcttggatga ccgattacat taataagaac ggggtgggta acccaaaaac ctgggaagtt  240
atttcccaaa acgttctgat tttctgcagc gcggatactg ccctggtgct taatccgcgc  300
atcgcggtgt acgacggctt ccacaaaact aaatggctgc cagccaagtt caattttaaa  360
acccagagcc aggagaaatt ctctggcaac gtgaccaccc cgattgctgc cttcggccat  420
tatctgtggg gtgagggcaa gccgcgtacc gtcgacttgt ctagcgaagc cgctgccaag  480
gaggcggccg ctaaaatgaa ggatcaggct attgccgttg ttaaacttta ccttctcaac  540
gaaagtcagg catcggtaat cgatactaca tcgggaatta ttactgactc tggtaaaact  600
cttagcggga aattaggtga taaatacaac actctggcga aagaagctgc tgacaatata  660
aaaaacttcc agggtaagaa actccgcagt tttaatgatg ctatggcatc tattaatgaa  720
ctagctaaca atccaaagat gaagttaagt caggcggata aaacagtcgt ttctaatgcc  780
ctcaaacaaa tggatttgtc agcactagct gaccgattca aagggttaga gaaagccttt  840
acttggggtg atcgacttct taaagccgag aaaatcagag aaggtgttgt tactggtatt  900
accacagggg actggcaaaa gctggcgttt gaggttgaag ctatgtacct cagtggtgtt  960
gctggcgccg tagcgttagg gattactact gccatgatta gcacagtcgc agtcgctttg  1020
tcacttccag ctgtagctgt ctctgcgctt actgttgtgt ccgtcattgg catctctatt  1080
ctcacatctt atatcgatgc tgataaggcc aaagcactga ataatgcagt gcttggctta  1140
tttaaataa                                                         1149
```

```
SEQ ID NO: 45          moltype = AA  length = 745
FEATURE                Location/Qualifiers
source                 1..745
                       mol_type = protein
                       organism = synthetic construct
SEQUENCE: 45
MSGGDGRGPG NSGLGHNGGQ ASGNVNGTSG KGGPSSGGGT DPNSGPGWGT THTPNGDIHN   60
YNPGEFGNGG SKPGGNGGNS GNHSGSSGGG QSSATAMAFG LPALATPGAE GLALSVSGDA  120
LSAAVADVLA ALKGPPKFGL WGIAIYGVLP SEIAKDDPKM MSKIVTSLPA DTVTETPVSS  180
LPLDQATVSV TKRVADIVKD ERQHIAVVTG RPMSVPVVDA KPTKRPGVFS VSIPGLPSLQ  240
VSVPKGVPAA KAPPKGIIAE KGDSRPAGFT AGGNSREAVI RFPKESGQKP VYVSVTDVLT  300
PAQVKQRLEE EKRRQQAWDA AHPEEGLKRE YDKAKAELDA EDKNIATLNS RIASTEKAIP  360
GARAAVQEAD KKVKEAEANK DDFVTYNPPH EYGSGWQDQV RYLDKDIQNQ NEKLKAAQTS  420
LNEMNESLSR DKAALSGAME SRKQKEKKAK DAENKLNEEK EAAAKEAAAK SDTMIVVATP  480
TPGFSYASGL TYGGGAFAGA PANGPSEGQI FFQTVLPAYQ SPNLCIGQLA WMTDYINKNG  540
VGNPKTWEVI SQNVLIFCSA DTALVLNPRI AVYDGFHKTK WAPAKFNFKT QSQEKFSGNV  600
TTPIAAFGHY LWGEGKPRTV DLSSVGLKIQ ANQIDPVMIA VKNNAAGTYQ ISGNFNRNTF  660
IDGDIPGLYL GNITMKTEGT LKIDAKGNWN YNGVVRAFND TYDANPSTHR SKSAEDLTTL  720
LRLTQGTPYE IRIPGELKVS GSGKK                                       745
```

```
SEQ ID NO: 46          moltype = DNA  length = 2238
FEATURE                Location/Qualifiers
source                 1..2238
                       mol_type = other DNA
                       organism = synthetic construct
```

```
SEQUENCE: 46
atgagtggtg gagacggacg aggtccgggt aattcaggtc tgggacacaa tggtggtcag    60
gccagtggga atgtgaacgg tacatcaggt aaaggtggcc cttcatcagg tggtggtacg   120
gatccaaaca gcgggccggg ctggggtacg acgcatacac ctaacgggga tattcataac   180
tataacccgg gggagtttgg taacggcggg agtaaacccg gtggtaatgg cggtaacagc   240
ggcaatcata gcgggagctc tggtggcgga cagtcttcgg ccaccgcgat ggccttcggt   300
ctgcctgcct tggccactcc gggggctgaa ggactggctt tatccgtttc cggcgatgcg   360
ttgtcggccg ctgttgctga tgtgctggct gccctgaaag tccgtttaa gtttggtctg   420
tgggggattg cgatttacgg agtgctgcct tctgagatag caaaagatga tccgaaaatg   480
atgtcaaaaa tcgtgacgtc attgccggca gacacggtaa cggagacgcc ggtcagctcc   540
ctgccgctgg accaggcgac ggtcagcgtc actaaacgtg tggcggatat tgtgaaggac   600
gagcggcagc atattgcggt tgtcaccggc cggccaatga gtgttcctgt ggtggatgcg   660
aaaccgacaa aacgtccggg ggtattcagt gtgtcgattc cgggtctccc gtctctgcag   720
gtgagcgtac ctaaaggtgt tccggccgcg aaagccccgc caaaaggcat tattgctgaa   780
aaaggtgatt cacgtccggc tggttttacg gccggtggta actcccgtga agccgttatt   840
cgtttcccga aagagagcgg acagaaaccg gtctatgtgt cggtgacgga tgttctttact   900
ccggcacagg taaaacagcg tctggaggaa gaaaagcgtc gccagcaggc atgggacgct   960
gctcacccgg aagaggggct gaaaagagag tatgataaag cgaaagctga gctggatgct  1020
gaagataaaa atattgcgac cttaaacagt cgcattgcat cgacagagaa ggcgatcccc  1080
ggtgcaaggg ctgctgttca ggaagccgat aaaaaggtaa aagaggcaga ggcaaataaa  1140
gatgattttg tgacttataa cccgcctcat gaatatggct ccgggtggca ggatcaggtt  1200
cgctatcttg ataaggatat tcagaatcag aatgagaaat taaaagctgc ccagacatct  1260
ttaaacgaaa tgaatgaatc cttatccagg gataaggctg cgctttccgg ggcgatggag  1320
agccggaaac aaaaggagaa aaaagcgaag gatgcagaaa ataaattaaa tgaggaaaag  1380
gaagccgctg ccaaggaggc ggccgctaaa tcagatacaa tgatagtagt tgctactccg  1440
accccggggtt ttagctacgc gagcggcttg acgtacggcg gtggtgcttt tgcgggtgcg  1500
cctgcgaacg gtccgtcgga aggccaaatc ttttttccaga ccgttctgcc ggcgtatcaa  1560
tccccgaatc tgtgtattgg tcaactggct tggatgaccg attacattaa taagaacggg  1620
gtgggtaacc caaaaacctg ggaagttatt tcccaaaacg ttctgatttt ctgcagcgcg  1680
gatactgccc tggtgcttaa tccgcgcatc gcggtgatag acggcttcca caaaactaaa  1740
tgggcgccag ccaagttcaa ttttaaaacc cagagccagg agaaattctc tggcaacgtg  1800
accaccccga ttgctgcctt cggccattat ctgtggggtg agggcaagcc gcgtaccgtc  1860
gacttgtcta cgcgttggtct gaagatccag gcaaaccaga tcgacccggt tatgattgcg  1920
gttaaaaaca acgcagcagg cacctaccag atctccggca acttcaaccg taatacctt  1980
atcgacggcg atattccggg tttatatctg ggtaacatta ccatgaaaac ggaaggcaca  2040
ctcaagatcg acgccaaggg taattggaat tataacggtg tcgtgcgcgc gtttaacgat  2100
acctacgacg ctaatccgtc gacccaccgt agcaaaagcg cagaagatct gacgacgttg  2160
ctgcgtttga cgcaaggtac gccgtacgag atcagaatcc cgggtgagct gaaggtgagc  2220
ggtagcggca agaagtaa                                                2238

SEQ ID NO: 47        moltype = AA  length = 742
FEATURE              Location/Qualifiers
source               1..742
                     mol_type = protein
                     organism = synthetic construct
SEQUENCE: 47
MSGGDGRGPG NSGLGHNGGQ ASGNVNGTSG KGGPSSGGGT DPNSGPGWGT THTPNGDIHN    60
YNPGEFGNGG SKPGGNGGNS GNHSGSSGGG QSSATAMAFG LPALATPGAE GLALSVSGDA   120
LSAAVADVLA ALKGPFKFGL WGIAIYGVLP SEIAKDDPKM MSKIVTSLPA DTVTETPVSS   180
LPLDQATVSV TKRVADIVKD ERQHIAVVTG RPMSVPVVDA KPTKRPGVFS VSIPGLPSLQ   240
VSVPKGVPAA KAPPKGIIAE KGDSRPAGFT AGGNSREAVI RFPKESGQKP VYVSVTDVLT   300
PAQVKQRLEE EKRRQQAWDA AHPEEGLKRE YDKAKAELDA EDKNIATLNS RIASTEKAIP   360
GARAAVQEAD KKVKEAEANK DDFVTYNPPH EYGSGWQDQV RYLDKDIQNQ NEKLKAAQTS   420
LNEMNESLSR DKAALSGAME SRKQKEKKAK DAENKLNEEK GSGSASGSDT MIVVATPTPG   480
FSYASGLTYG GGAFAGAPAN GPSEGQIFFQ TVLPAYQSPN LCIGQLAWMT DYINKNGVGN   540
PKTWEVISQN VLIFCSADTA LVLNPRIAVY DGFHKTKWAP AKFNFKTQSQ EKFSGNVTTP   600
IAAFGHYLWG EGKPRTVDLS SVGLKIQANQ IDPVMIAVKN NAAGTYQISG NFNRNTFIDG   660
DIPGLYLGNI TMKTEGTLKI DAKGNWNYNG VVRAFNDTYD ANPSTHRSKS AEDLTTLLRL   720
TQGTPYEIRI PGELKVSGSG KK                                            742

SEQ ID NO: 48        moltype = DNA  length = 2229
FEATURE              Location/Qualifiers
source               1..2229
                     mol_type = other DNA
                     organism = synthetic construct
SEQUENCE: 48
atgagtggtg gagacggacg aggtccgggt aattcaggtc tgggacacaa tggtggtcag    60
gccagtggga atgtgaacgg tacatcaggt aaaggtggcc cttcatcagg tggtggtacg   120
gatccaaaca gcgggccggg ctggggtacg acgcatacac ctaacgggga tattcataac   180
tataacccgg gggagtttgg taacggcggg agtaaacccg gtggtaatgg cggtaacagc   240
ggcaatcata gcgggagctc tggtggcgga cagtcttcgg ccaccgcgat ggccttcggt   300
ctgcctgcct tggccactcc gggggctgaa ggactggctt tatccgtttc cggcgatgcg   360
ttgtcggccg ctgttgctga tgtgctggct gccctgaaag tccgtttaa gtttggtctg   420
tgggggattg cgatttacgg agtgctgcct tctgagatag caaaagatga tccgaaaatg   480
atgtcaaaaa tcgtgacgtc attgccggca gacacggtaa cggagacgcc ggtcagctcc   540
ctgccgctgg accaggcgac ggtcagcgtc actaaacgtg tggcggatat tgtgaaggac   600
gagcggcagc atattgcggt tgtcaccggc cggccaatga gtgttcctgt ggtggatgcg   660
aaaccgacaa aacgtccggg ggtattcagt gtgtcgattc cgggtctccc gtctctgcag   720
gtgagcgtac ctaaaggtgt tccggccgcg aaagccccgc caaaaggcat tattgctgaa   780
```

```
aaaggtgatt cacgtccggc tggtttttacg gccggtggta actcccgtga agccgttatt  840
cgtttcccga aagagagcgg acagaaaccg gtctatgtgt cggtgacgga tgttcttact  900
ccggcacagg taaaacagcg tctggaggaa gaaaagcgtc gccagcaggc atgggacgct  960
gctcacccgg aagaggggct gaaaagagag tatgataaag cgaaagctga gctggatgct 1020
gaagataaaa atattgcgac cttaaacagt cgcattgcat cgacagagaa ggcgatcccc 1080
ggtgcaaggg ctgctgttca ggaagccgat aaaaaggtaa aagaggcaga ggcaaataaa 1140
gatgattttg tgacttataa cccgcctcat gaatatggct ccgggtggca ggatcaggtt 1200
cgctatcttg ataaggatat tcagaatcag aatgagaaat aaaagctgc ccagacatct 1260
ttaaacgaaa tgaatgaatc cttatccagg gataaggctg cgctttccgg ggcgatggag 1320
agccggaaac aaaaggagaa aaaagcgaag gatgcagaaa ataaattaaa tgaggaaaag 1380
ggctccggat cggcttctgg gtcagataca atgatagtag ttgctactcc gaccccgggt 1440
tttagctacg cgagcggctt gacgtacggc ggtggtgcgt ttgcgggtgc gcctgcgaac 1500
ggtccgtcgg aaggccaaat cttttttccag accgttctgc cggcgtatca atccccgaat 1560
ctgtgtattg gtcaactggc ttggatgacc gattacatta ataagaacgg ggtgggtaac 1620
ccaaaaacct gggaagttat ttcccaaaac gttctgattt tctgcagcgc ggatactgcc 1680
ctggtgctta atccgcgcat cgcggtgtac gacggcttcc acaaaactaa atgggcgcca 1740
gccaagttca attttaaaac ccagagccag gagaaattct ctggcaacgt gaccaccccg 1800
attgctgcct tcggccatta tctgtggggt gagggcaagc cgcgtaccgt cgacttgtct 1860
agcgttggtc tgaagatcca ggcaaaccag atcgacccgg ttatgattgc ggttaaaaac 1920
aacgcagcag gcacctacca gatctccggc aacttcaacc gtaatacctt tatcgacggc 1980
gatattccgg gtttatatct gggtaacatt accatgaaaa cggaaggcac actcaagatc 2040
gacgccaagg gtaattggaa ttataacggt gtcgtgcgcg cgtttaacga tacctacgac 2100
gctaatccgt cgacccaccg tagcaaaagc gcagaagatc tgacgacgtt gctgcgtttg 2160
acgcaaggta cgccgtacga gatcagaatc ccgggtgagc tgaaggtgag cggtagcggc 2220
aagaagtaa                                                                                    2229
```

```
SEQ ID NO: 49          moltype = AA   length = 735
FEATURE                Location/Qualifiers
source                 1..735
                       mol_type = protein
                       organism = synthetic construct
SEQUENCE: 49
MSGGDGRGPG NSGLGHNGGQ ASGNVNGTSG KGGPSSGGGT DPNSGPGWGT THTPNGDIHN  60
YNPGEFGNGG SKPGGNGGNS GNHSGSSGGG QSSATAMAFG LPALATPGAE GLALSVSGDA 120
LSAAVADVLA ALKGPFKFGL WGIAIYGVLP SEIAKDDPKM MSKIVTSLPA DTVTETPVSS 180
LPLDQATVSV TKRVADIVKD ERQHIAVVTG RPMSVPVVDA KPTKRPGVFS VSIPGLPSLQ 240
VSVPKGVPAA KAPPKGIIAE KGDSRPAGFT AGGNSREAVI RFPKESGQKP VYVSVTDVLT 300
PAQVKQRLEE EKRRQQAWDA AHPEEGLKRE YDKAKAELDA EDKNIATLNS RIASTEKAIP 360
GARAAVQEAD KKVKEAEANK DDFVTYNPPH EYGSGWQDQV RYLDKDIQNQ NEKLKAAQTS 420
LNEMNESLSR DKAALSGAME SRKQKEKKAK DAENKLNEEK SDTMIVVATP TPGFSYASGL 480
TYGGGAFAGA PANGPSEGQI FFQTVLPAYQ SPNLCIGQLA WMTDYINKNG VGNPKTWEVI 540
SQNVLIFCSA DTALVLNPRI AVYDGFHKTK WAPAKFNFKT QSQEKFSGNV TTPIAAFGHY 600
LWGEGKPRTV DLSSVGLKIQ ANQIDPVMIA VKNNAAGTYQ ISGNFNRNTF IDGDIPGLYL 660
GNITMKTEGT LKIDAKGNWN YNGVVRAFND TYDANPSTHR SKSAEDLTTL LRLTQGTPYE 720
IRIPGELKVS GSGKK                                                                   735
```

```
SEQ ID NO: 50          moltype = DNA   length = 2208
FEATURE                Location/Qualifiers
source                 1..2208
                       mol_type = other DNA
                       organism = synthetic construct
SEQUENCE: 50
atgagtggtg gagacggacg aggtccgggt aattcaggtc tgggacacaa tggtggtcag  60
gccagtggga atgtgaacgg tacatcaggt aaaggtggcc cttcatcagg tggtggtacg 120
gatccaaaca gcgggccggg ctggggtacg acgcatacca ctaacgggga tattcataac 180
tataacccgg gggagtttgg taacggcggg agtaaacccg gtggtaatgg cggtaacagc 240
ggcaatcata cgcgggagct ctggtggcgga cagtcttcgg ccaccgcgat ggccttcggt 300
ctgcctgcct tggccactcc ggggggctgaa ggactggctt tatccgtttc cggcgatgcg 360
ttgtcggccg ctgttgctga tgtcgctggct gccctgaagg gtccgtttaa gtttggtctg 420
tgggggattg cgatttacgg agtgctgcct tctgagatag caaaagatga tccgaaaatg 480
atgtcaaaaa tcgtgacgtc attgccggca gacacggtaa cggagacgcc ggtcagctcc 540
ctgccgctgg accaggcgac ggtcagcgtc actaaacgtg tggcggatat tgtgaaggac 600
gagcggcagc atattgcggt tgtcaccggc cggccaatga gtgttcctgt ggtggatgcg 660
aaaccgacaa aacgtccggg ggtattcagt gtgtcgattc cgggtctccc gtctctgcag 720
gtgagcgtac ctaaaggtgt tccggccgcg aaagccccgc caaaaggcat tattgctgaa 780
aaaggtgatt cacgtccggc tggtttttacg gccggtggta actcccgtga agccgttatt  840
cgtttcccga aagagagcgg acagaaaccg gtctatgtgt cggtgacgga tgttcttact  900
ccggcacagg taaaacagcg tctggaggaa gaaaagcgtc gccagcaggc atgggacgct  960
gctcacccgg aagaggggct gaaaagagag tatgataaag cgaaagctga gctggatgct 1020
gaagataaaa atattgcgac cttaaacagt cgcattgcat cgacagagaa ggcgatcccc 1080
ggtgcaaggg ctgctgttca ggaagccgat aaaaaggtaa aagaggcaga ggcaaataaa 1140
gatgattttg tgacttataa cccgcctcat gaatatggct ccgggtggca ggatcaggtt 1200
cgctatcttg ataaggatat tcagaatcag aatgagaaat aaaagctgc ccagacatct 1260
ttaaacgaaa tgaatgaatc cttatccagg gataaggctg cgctttccgg ggcgatggag 1320
agccggaaac aaaaggagaa aaaagcgaag gatgcagaaa ataaattaaa tgaggaaaag 1380
tcagatacaa tgatagtagt tgctactccg accccgggtt ttagctacgc gagcggcttg 1440
acgtacggcg gtggtgcgtt tgcgggtgcg cctgcgaacg gtccgtcgga aggccaaatc 1500
ttttttccaga ccgttctgcc ggcgtatcaa tccccgaatc tgtgtattgg tcaactggct 1560
tggatgaccg attacattaa taagaacggg gtgggtaacc caaaaacctg ggaagttatt 1620
```

```
tcccaaaacg ttctgatttt ctgcagcgcg gatactgccc tggtgcttaa tccgcgcatc   1680
gcggtgtacg acggcttcca caaaactaaa tgggcgccag ccaagttcaa ttttaaaacc   1740
cagagccagg agaaattctc tggcaacgtg accaccccga ttgctgcctt cggccattat   1800
ctgtggggtg agggcaagcc gcgtaccgtc gacttgtcta gcgttggtct gaagatccag   1860
gcaaaccaga tcgacccggt tatgattgcg gttaaaaaca acgcagcagg cacctaccag   1920
atctccggca acttcaaccg taataccttt atcgacggcg atattccggg tttatatctg   1980
ggtaacatta ccatgaaaac ggaaggcaca ctcaagatcg acgccaaggg taattggaat   2040
tataacggtg tcgtgcgcgc gtttaacgat acctacgacg ctaatccgtc gacccaccgt   2100
agcaaaagcg cagaagatct gacgacgttg ctgcgtttga cgcaaggtac gccgtacgag   2160
atcagaatcc cgggtgagct gaaggtgagc ggtagcggca agaagtaa              2208
```

SEQ ID NO: 51         moltype = AA   length = 755
FEATURE               Location/Qualifiers
source                1..755
                      mol_type = protein
                      organism = synthetic construct
SEQUENCE: 51

```
MSGGDGRGPG NSGLGHNGGQ ASGNVNGTSG KGGPSSGGGT DPNSGPGWGT THTPNGDIHN   60
YNPGEFGNGG SKPGGNGGNS GNHSGSSGGG QSSATAMAFG LPALATPGAE GLALSVSGDA   120
LSAAVADVLA ALKGPFKFGL WGIAIYGVLP SEIAKDDPKM MSKIVTSLPA DTVTETPVSS   180
LPLDQATVSV TKRVADIVKD ERQHIAVVTG RPMSVPVVDA KPTKRPGVFS VSIPGLPSLQ   240
VSVPKGVPAA KAPPKGIIAE KGDSRPAGFT AGGNSREAVI RFPKESGQKP VYVSVTDVLT   300
PAQVKQRLEE EKRRQQAWDA AHPEEGLKRE YDKAKAELDA EDKNIATLNS RIASTEKAIP   360
GARAAVQEAD KKVKEAEANK DDFVTYNPPH EYGSGWQDQV RYLDKDIQNQ NEKLKAAQTS   420
LNEMNESLSR DKAALSGAME SRKQKEKKAK DAENKLNEEK EAAAKEAAAK EAAAKEAAAK   480
SDTMIVVATP TPGFSYASGL TYGGGAFAGA PANGPSEGQI FFQTVLPAYQ SPNLCIGQLA   540
WMTDYINKNG VGNPKTWEVI SQNVLIFCSA DTALVLNPRI AVYDGFHKTK WAPAKFNFKT   600
QSQEKFSGNV TTPIAAFGHY LWGEGKPRTV DLSSVGLKIQ ANQIDPVMIA VKNNAAGTYQ   660
ISGNFNRNTF IDGDIPGLYL GNITMKTEGT LKIDAKGNWN YNGVVRAFND TYDANPSTHR   720
SKSAEDLTTL LRLTQGTPYE IRIPGELKVS GSGKK                            755
```

SEQ ID NO: 52         moltype = DNA   length = 2268
FEATURE               Location/Qualifiers
source                1..2268
                      mol_type = other DNA
                      organism = synthetic construct
SEQUENCE: 52

```
atgagtggtg gagacggacg aggtccgggt aattcaggtc tgggacacaa tggtggtcag   60
gccagtggga atgtgaacgg tacatcaggt aaaggtgcc cttcatcagg tggtggtacg   120
gatccaaaca gcgggccggg ctggggtacg acgcatacac ctaacgggga tattcataac   180
tataaccccg gggagtttgg taacggcggg agtaaacccg gtggtaatgg cggtaacagc   240
ggcaatcata gcgggagctc tggtggcgga cagtcttcgg ccaccgcgat ggccttcggt   300
ctgcctgcct tggccactcc gggggctgaa ggactggctt tatccgtttc cggcgatgcg   360
ttgtcggccg ctgttgctga tgtgctggct gccctgaaag tccgtttaa gtttggtctg   420
tgggggattg cgatttacgg agtgctgcct tctgagatag caaaagatga tccgaaaatg   480
atgtcaaaaa tcgtgacgtc attgccggca gacacggtaa cggagacgcc ggtcagctcc   540
ctgccgctgg accaggcgac ggtcagcgtc actaaacgtg tggcggatat tgtgaaggac   600
gagcggcagc atattgcggt tgtcaccggc cggccaatga gtgttcctgt ggtggatgcg   660
aaaccgacaa aacgtccggg ggtattcagt gtgtcgattc cgggtctccc gtctctgcag   720
gtgagcgtac ctaaaggtgt tccggccgcg aaagccccgc caaaaggcat tattgctgaa   780
aaaggtgatt cacgtccggc tggtttacg gccggtgtga actcccgtga agccgttatt   840
cgtttcccga aagagagcgg acagaaaccg gtctatgtgt cggtgacgga tgttcttact   900
ccggcacagg taaaacagcg tctggaggaa gaaaagcgtc gccagcaggc atgggacgct   960
gctcacccgg aagaggggct gaaaagagag tatgataaag cgaaagctga gctggatgct   1020
gaagataaaa atattgcgac cttaaacagt cgcattgcat tatccggagca ggcgatcccc   1080
ggtgcaaggg ctgctgttca ggaagccgat aaaaaggtaa aagagcaga ggcaaataaa   1140
gatgattttg tgacttataa cccgcctcat gaatatggct ccgggtggca ggatcaggtt   1200
cgctatcttg ataaggatat tcagaatcag aatgagaaat aaaagctgc ccagacatct   1260
ttaaacgaaa tgaatgaatc cttatccagg gataaggctg cgctttccgg ggcgatggag   1320
agccggaaac aaaaggagaa aaaagcgaag gatgcagaaa ataaattaaa tgaggaaaag   1380
gaagccgctg ccaaggaggc ggccgctaaa gaagccgctg ccaaggaggc ggccgctaaa   1440
tcagatacaa tgatagtagt tgctactccg accccgggtt ttagctacgc gagcggcttg   1500
acgtacggcg gtggtgcgtt tgcgggtgcg cctgcgaacg tccgtcgga aggccaaatc   1560
tttttccaga ccgttctgcc ggcgtatcaa tccccgaatc tgtgtattgg tcaactggct   1620
tggatgaccg attacattaa taagaacggg gtgggtaacc caaaaacctg ggaagttatt   1680
tcccaaaacg ttctgatttt ctgcagcgcg gatactgccc tggtgcttaa tccgcgcatc   1740
gcggtgtacg acggcttcca caaaactaaa tgggcgccag ccaagttcaa ttttaaaacc   1800
cagagccagg agaaattctc tggcaacgtg accaccccga ttgctgcctt cggccattat   1860
ctgtggggtg agggcaagcc gcgtaccgtc gacttgtcta gcgttggtct gaagatccag   1920
gcaaaccaga tcgacccggt tatgattgcg gttaaaaaca acgcagcagg cacctaccag   1980
atctccggca acttcaaccg taataccttt atcgacggcg atattccggg tttatatctg   2040
ggtaacatta ccatgaaaac ggaaggcaca ctcaagatcg acgccaaggg taattggaat   2100
tataacggtg tcgtgcgcgc gtttaacgat acctacgacg ctaatccgtc gacccaccgt   2160
agcaaaagcg cagaagatct gacgacgttg ctgcgtttga cgcaaggtac gccgtacgag   2220
atcagaatcc cgggtgagct gaaggtgagc ggtagcggca agaagtaa              2268
```

SEQ ID NO: 53         moltype = AA   length = 742
FEATURE               Location/Qualifiers
source                1..742

```
                        mol_type = protein
                        organism = synthetic construct
SEQUENCE: 53
MSGGDGRGPG  NSGLGHNGGQ  ASGNVNGTSG  KGGPSSGGGT  DPNSGPGWGT  THTPNGDIHN   60
YNPGEFGNGG  SKPGGNGGNS  GNHSGSSGGG  QSSATAMAFG  LPALATPGAE  GLALSVSGDA  120
LSAAVADVLA  ALKGPFKFGL  WGIAIYGVLP  SEIAKDDPKM  MSKIVTSLPA  DTVTETPVSS  180
LPLDQATVSV  TKRVADIVKD  ERQHIAVVTG  RPMSVPVVDA  KPTKRPGVFS  VSIPGLPSLQ  240
VSVPKGVPAA  KAPPKGIIAE  KGDSRPAGFT  AGGNSREAVI  RFPKESGQKP  VYVSVTDVLT  300
PAQVKQRLEE  EKRRQQAWDA  AHPEEGLKRE  YDKAKAELDA  EDKNIATLNS  RIASTEKAIP  360
GARAAVQEAD  KKVKEAEANK  DDFVTYNPPH  EYGSGWQDQV  RYLDKDIQNQ  NEKLKAAQTS  420
LNEMNESLSR  DKAALSGAME  SRKQKEKKAK  DAENKLNEEK  GSGSASGSDT  MIVVATPTPG  480
FSYASGLTYG  GGAFAGAPAN  GPSEGQIFFQ  TVLPAYQSPN  LCIGQLAWMT  DYINKNGVGN  540
PKTWEVISQN  VLIFCSADTA  LVLNPRIAVY  DGFHKTKWAP  AKFNFKTQSQ  EKFSGNVTTP  600
IAAFGHYLWG  EGKPRTVDLS  SVGLKIQANQ  IDPVMIAVKN  NAAGTYQISG  NFNRNTFIDG  660
DIPGLYLGNI  TMKTEGTLKI  DAKGNWNYNG  VVRAFNDTYD  ANPSTHRSKS  AEDLTTLLRL  720
TQGTPYEIRI  PGELKVSGSG  KK                                               742

SEQ ID NO: 54        moltype = DNA  length = 2229
FEATURE              Location/Qualifiers
source               1..2229
                     mol_type = other DNA
                     organism = synthetic construct
SEQUENCE: 54
atgagtggtg  gagacggacg  aggtccgggt  aattcaggtc  tgggacacaa  tggtggtcag    60
gccagtggga  atgtgaacgg  tacatcaggt  aaaggtggcc  cttcatcagg  tggtggtacg   120
gatccaaaca  gcgggccggg  ctggggtacg  acgcatcac   ctaacgggga  tattcataac   180
tataacccgg  gggagtttgg  taacggcggg  agtaaacccg  gtggtaatgg  cggtaacagc   240
ggcaatcata  gcgggagctc  tggtggcgga  cagtcttcgg  ccaccgcgat  ggccttcggt   300
ctgcctgcct  tggccactcc  gggggctgaa  ggactggctt  tatccgtttc  cggcgatgcg   360
ttgtcggccg  ctgttgctga  tgtgctggct  gccctgaaag  gtccgtttaa  gtttggtctg   420
tgggggattg  cgatttacgg  agtgctgcct  tctgagatag  caaaagatga  tccgaaaatg   480
atgtcaaaaa  tcgtgacgtc  attgccggca  gacacggtaa  cggagacgcc  ggtcagctcc   540
ctgccgctgg  accaggcgac  ggtcagcgtc  actaaacgtg  tggcggatat  tgtgaaggac   600
gagcggcagc  atattgcggt  tgtcaccggc  cggccaatga  gtgttcctgt  ggtggatgcg   660
aaaccgacaa  aacgtccggg  ggtattcagt  gtgtcgattc  cgggtctccc  gtctctgcag   720
gtgagcgtac  ctaaaggtgt  tccggccgcg  aaagccccgc  caaaaggcat  tattgctgaa   780
aaaggtgatt  cacgtccggc  tggttttacg  gccggtggta  actcccgtga  agccgttatt   840
cgtttcccga  aagagagcgg  aacagaaaccg  gtctatgtgt  cggtgacgga  tgttcttact   900
ccggcacagg  taaaacagcg  tctggaggaa  gaaaagcgtc  gacagcaggc  atgggacgct   960
gctcacccgg  aagaggggct  gaaaagagag  tatgataaag  cgaaagctga  gctggatgct  1020
gaagataaaa  atattgcgac  cttaaacagt  cgcattgcat  cgacagagaa  ggcgatcccc  1080
ggtgcaaggg  ctgctgttca  ggaagccgat  aaaaaggtaa  aagaggcaga  ggcaaataaa  1140
gatgattttg  tgacttataa  cccgcctcat  gaatatggct  ccggtggaca  ggatcaggtt  1200
cgctatcttg  ataaggatat  tcagaatcag  aatgagaaat  taaaagctgc  ccagacatct  1260
ttaaacgaaa  tgaatgaatc  cttatccagg  gataaggctg  cgctttccgg  ggcgatggag  1320
agccggaaac  aaaaggagaa  aaaagcgaag  gatgcagaaa  ataaattaaa  tgaggaaaag  1380
ggctccggat  cggcttctgg  gtcagataca  atgatagtag  ttgctactcc  gaccccgggt  1440
tttagctacg  cgagcggctt  gacgtacggc  ggtggtgcg   ttgcgggtgc  gcctgcgaac  1500
ggtccgtcgg  aaggccaaat  cttttttcag  accgttctgc  cggcgtatca  atccccgaat  1560
ctgtgtattg  gtcaactggc  ttggatgacc  gattacatta  taagaacggg  ggtgggtaac  1620
ccaaaaacct  gggaagttat  ttcccaaaac  gttctgattt  tctgcagcgc  ggatactgcc  1680
ctggtgctta  atccgcgcat  cgcggtgtac  gacggcttcc  acaaaactaa  atgggcgcca  1740
gccaagttca  attttaaaac  ccagagccag  gagaaattct  ctggcaacgt  gaccaccccg  1800
attgctgcct  tcggccatta  tctgtggggt  gagggcaagc  cgcgtaccgt  cgacttgtct  1860
agcgttggtc  tgaagatcca  ggcaaaccag  atcgacccgg  ttatgattgc  ggttaaaaac  1920
aacgcagcag  gcacctacca  gatctccggc  aacttcaacc  gtaataccct  tatcgacgtc  1980
gatattccgg  gtttatatct  gggtaacatt  accatgaaaa  cggaaggcac  actcaagatc  2040
gacgccaagg  gtaattggaa  ttataacggt  gtcgtgcgcg  cgtttaacga  tacctacgac  2100
gctaatccgt  cgacccaccg  tagcaaaagc  gcagaagatc  tgacgacgtt  gctgcgtttg  2160
acgcaaggta  cgccgtacga  gatcagaatc  ccgggtgagc  tgaaggtgag  cggtagcggc  2220
aagaagtaa                                                               2229

SEQ ID NO: 55        moltype = AA  length = 836
FEATURE              Location/Qualifiers
source               1..836
                     mol_type = protein
                     organism = synthetic construct
SEQUENCE: 55
MSGGDGRGPG  NSGLGHNGGQ  ASGNVNGTSG  KGGPSSGGGT  DPNSGPGWGT  THTPNGDIHN   60
YNPGEFGNGG  SKPGGNGGNS  GNHSGSSGGG  QSSATAMAFG  LPALATPGAE  GLALSVSGDA  120
LSAAVADVLA  ALKGPFKFGL  WGIAIYGVLP  SEIAKDDPKM  MSKIVTSLPA  DTVTETPVSS  180
LPLDQATVSV  TKRVADIVKD  ERQHIAVVTG  RPMSVPVVDA  KPTKRPGVFS  VSIPGLPSLQ  240
VSVPKGVPAA  KAPPKGIIAE  KGDSRPAGFT  AGGNSREAVI  RFPKESGQKP  VYVSVTDVLT  300
PAQVKQRLEE  EKRRQQAWDA  AHPEEGLKRE  YDKAKAELDA  EDKNIATLNS  RIASTEKAIP  360
GARAAVQEAD  KKVKEAEANK  DDFVTYNPPH  EYGSGWQDQV  RYLDKDIQNQ  NEKLKAAQTS  420
LNEMNESLSR  DKAALSGAME  SRKQKEKKAK  DAENKLNEEK  KKPRKGTKDY  GHDYFPDPKT  480
EDIKGLGELK  EGKPKTPKQG  GGGKRARWYG  DKKRKIYEWD  SQHGELEGYR  ASDGEHLGAF  540
DPKTGKQVKG  PDPKRNIKKY  LSDTMIVVAT  PTPGFSYASG  LTYGGGAFAG  APANGPSEGQ  600
IFFQTVLPAY  QSPNLCIGQL  AWMTDYINKN  GVGNPKTWEV  ISQNVLIFCS  ADTALVLNPR  660
```

```
IAVYDGFHKT KWAPAKFNFK TQSQEKFSGN VTTPIAAFGH YLWGEGKPRT VDLSSVGLKI  720
QANQIDPVMI AVKNNAAGTY QISGNFNRNT FIDGDIPGLY LGNITMKTEG TLKIDAKGNW  780
NYNGVVRAFN DTYDANPSTH RSKSAEDLTT LLRLTQGTPY EIRIPGELKV SGSGKK      836

SEQ ID NO: 56          moltype = DNA  length = 2532
FEATURE                Location/Qualifiers
source                 1..2532
                       mol_type = other DNA
                       organism = synthetic construct
SEQUENCE: 56
atgagtggtg gagacggacg aggtccgggt aattcaggtc tgggacacaa tggtggtcag  60
gccagtggga atgtgaacgg tacatcaggt aaaggtggcc cttcatcagg tggtggtacg  120
gatccaaaca gcgggccggg ctggggtacg acgcatacac ctaacgggga tattcataac  180
tataacccgg gggagtttgg taacgcgggg agtaaacccg gtggtaaatg ggtgaacagc  240
ggcaatcata gcgggagctc tggtggcgga cagtcttcgg ccaccgcgat ggccttcggt  300
ctgcctgcct tggccactcc gggggctgaa ggactggctt tatccgtttc cggcgatgcg  360
ttgtcggccg ctgttgctga tgtgctggct gccctgaaag tccgtttaa gtttggtctg  420
tggggattg cgatttacgg agtgctgcct tctgagatag caaaagatga tccgaaaatg  480
atgtcaaaaa tcgtgacgtc attgccggca gacacggtaa cggagacgcc ggtcagctcc  540
ctgccgctgg accaggcgac ggtcagcgtc actaaacgtg tggcggatat tgtgaaggac  600
gagcggcagc atattgcggt tgtcaccggc cggccaatga gtgttcctgt ggtggatgcg  660
aaaccgacaa aacgtccggg ggtattcagt gtgtcgattc cgggtctccc gtctctgcag  720
gtgagcgtac ctaaaggtgt tccggccgcg aaagcccccgc caaaaggcat tattgctgaa  780
aaaggtgatt cacgtccggc tggttttacg gccggtggta actcccgtga agccgttatt  840
cgtttcccga aagagagcgg acagaaaccg gtctatgtgt cggtgacgga tgttcttact  900
ccggcacagg taaaacagcg tctggaggaa gaaaagcgtc agcagcaggc atggagacgc  960
gctcacccgg aagaggggct gaaaagagag tatgataaag cgaaagctga gctggatgct  1020
gaagataaaa atattgcgac cttaaacagt cgcattgcat cgacagagaa ggcgatcccc  1080
ggtgcaaggg ctgctgttca ggaagccgat aaaaaggtaa aagaggcaga ggcaaataaa  1140
gatgattttg tgacttataa cccgcctcat gaatatggct ccgggtggca ggatcaggtt  1200
cgctatcttg ataaggatat tcagaatcag aatgagaaat taaaagctgc ccagacatct  1260
ttaaacgaaa tgaatgaatc cttatccagg gataaggctg cgctttccgg ggcgatggag  1320
agccggaaac aaaaggagaa aaaagcgaag gatgcagaaa ataaattaaa tgaggaaaag  1380
aaaaaacctc gtaagggaac taaagattac ggccatgatt attttcctga tcccaagact  1440
gaagatatta aggggttggg agagttgaaa gagggtaaac ctaaaacccc taaacaaggt  1500
ggtggtggta agcgggcccg atggtatggt gataaaaagc gtaaaattta tgaatgggat  1560
tcccagcacg gtgagcttga agggtaccgc gccagtgatg gcgaacacct cggggcattc  1620
gatccaaaaa cgggtaagca ggttaaaggg ccggatccaa aacgaaacat taaaaaatat  1680
cttggctccg gatcggcttc tgggtcagat acaatgatag tagttgctac tccgaccccg  1740
ggttttagct acgcgagcgg cttgacgtac ggcggtggtg cgtttgcggg tgcgcctgcg  1800
aacggtccgt cggaaggcca aatcttttc cagaccgttc tgccggcgta tcaatccccg  1860
aatctgtgta ttggtcaact ggcttggatg accgattaca ttaataagaa cggggtgggt  1920
aacccaaaaa cctgggaagt tatttcccaa aacgttctga ttttctgcag cgccgatact  1980
gccctggtgc ttaatccgcg catcgcggtg tacgacggct ccacaaaac taaatgggcg  2040
ccagccaagt tcaattttaa aacccagagc caggagaaat tctctggcaa cgtgaccacc  2100
ccgattgctg ccttcggcca ttatctgtgg ggtgagggca gccgcgtac cgtcgacttg  2160
tctagcgttg gtctgaagat ccaggcaaac cagatcgacc cggttatgat tgcggttaaa  2220
aacaacgcag caggcaccta ccagatctcc ggcaacttca accgtaatac ctttatcgac  2280
ggcgatattc cgggtttata tctgggtaac attaccatga aaacgaagg cacactcaag  2340
atcgacgcca agggtaattg gaattataac ggtgtcgtgc gcgcgtttaa cgatacctac  2400
gacgctaatc cgtcgaccca ccgtagcaaa agcgcagaag atctgacgac gttgctgcgt  2460
ttgacgcaag gtacgccgta cgagatcaga atcccggggtg agctgaaggt gagcggtagc  2520
ggcaagaagt aa                                                     2532

SEQ ID NO: 57          moltype = AA  length = 843
FEATURE                Location/Qualifiers
source                 1..843
                       mol_type = protein
                       organism = synthetic construct
SEQUENCE: 57
MSGGDGRGPG NSGLGHNGGQ ASGNVNGTSG KGGPSSGGGT DPNSGPGWGT THTPNGDIHN  60
YNPGEFGNGG SKPGGNGGNS GNHSGSSGGG QSSATAMAFG LPALATPGAE GLALSVSGDA  120
LSAAVADVLA ALKGPFKFGL WGIAIYGVLP SEIAKDDPKM MSKIVTSLPA DTVTETPVSS  180
LPLDQATVSV TKRVADIVKD ERQHIAVVTG RPMSVPVVDA KPTKRPGVFS VSIPGLPSLQ  240
VSVPKGVPAA KAPPKGIIAE KGDSRPAGFT AGGNSREAVI RFPKESGQKP VYVSVTDVLT  300
PAQVKQRLEE EKRRQQAWDA AHPEEGLKRE YDKAKAELDA EDKNIATLNS RIASTEKAIP  360
GARAAVQEAD KKVKEAEANK DDFVTYNPPH EYGSGWQDQV RYLDKDIQNQ NEKLKAAQTS  420
LNEMNESLSR DKAALSGAME SRKQKEKKAK DAENKLNEEK KKPRKGTKDY GHDYFPDPKT  480
EDIKGLGELK EGKPKTPKQG GGGKRARWYG DKKRKIYEWD SQHGELEGYR ASDGEHLGAF  540
DPKTGKQVKG PDPKRNIKKY LGSGSASGSD TMIVVATPTP GFSYASGLTY GGGAFAGAPA  600
NGPSEGIFF QTVLPAYQSP NLCIGQLAWM TDYINKNGVG NPKTWEVISQ NVLIFCSADT  660
ALVLNPRIAV YDGFHKTKWA PAKFNFKTQS QEKFSGNVTT PIAAFGHYLW GEGKPRTVDL  720
SSVGLKIQAN QIDPVMIAVK NNAAGTYQIS GNFNRNTFID GDIPGLYLGN ITMKTEGTLK  780
IDAKGNWNYN GVVRAFNDTY DANPSTHRSK SAEDLTTLLR LTQGTPYEIR IPGELKVSGS  840
GKK                                                               843

SEQ ID NO: 58          moltype = DNA  length = 2532
FEATURE                Location/Qualifiers
source                 1..2532
```

```
                         mol_type = other DNA
                         organism = synthetic construct
SEQUENCE: 58
atgagtggtg gagacggacg aggtccgggt aattcaggtc tgggacacaa tggtggtcag    60
gccagtggga atgtgaacgg tacatcaggt aaaggtggcc cttcatcagg tggtggtacg   120
gatccaaaca gcgggccggg ctggggtacg acgcatacac ctaacgggga tattcataac   180
tataaccccg gggagtttgg taacggcggg agtaaacccg gtggtaatgg cggtaacagc   240
ggcaatcata gcgggagctc tggtggcgga cagtcttcgg ccaccgcgat ggccttcggt   300
ctgcctgcct tggccactcc gggggctgaa ggactggctt tatccgtttc cggcgatgcg   360
ttgtcggccg ctgttgctga tgtgctggct gccctgaaag gtccgtttaa gtttggtctg   420
tgggggattg cgatttacgg agtgctgcct tctgagatag caaaagatga tccgaaaatg   480
atgtcaaaaa tcgtgacgtc attgccggca gacacggtaa cggagacgcc ggtcagctcc   540
ctgccgctgg accaggcgac ggtcagcgtc actaaacgtg tggcggatat tgtgaaggac   600
gagcggcagc atattgcggt tgtcaccggc cggccaatga gtgttcctgt ggtggatgcg   660
aaaccgacaa aacgtccggg ggtattcagt gtgtcgattc cgggtctccc gtctctgcag   720
gtgagcgtac ctaaaggtgt tccggccgcg aaagccccgc caaaaggcat tattgctgaa   780
aaaggtgatt cacgtccggc tggttttacg gccggtggta actcccgtga agccgttatt   840
cgtttcccga aagagagcgg acagaaaccg gtctatgtgt cggtgacgga tgttcttact   900
ccggcacagg taaaacagcg tctggaggaa gaaaagcgtc gccagcaggc atgggacgct   960
gctcacccgg aagaggggct gaaaagagag tatgataaag cgaaagctga gctggatgct  1020
gaagataaaa atattgcgac cttaaacagt cgcattgcat cgacagagaa ggcgatcccc  1080
ggtgcaaggg ctgctgttca ggaagccgat aaaaaggtaa aagaggcaga agcaaataaa  1140
gatgattttg tgacttataa cccgcctcat gaatatggct ccgggtggca ggatcaggtt  1200
cgctatcttg ataaggatat tcagaatcag aatgagaaat aaaaagctgc ccagacatct  1260
ttaaacgaaa tgaatgaatc cttatccagg gataaggctg cgctttccgg ggcgatggag  1320
agccggaaac aaaaggagaa aaaagcgaag gatgcagaaa ataaattaaa tgaggaaaag  1380
aaaaaacctc gtaagggaac taaagattac ggccatgatt attttcctga tcccaagact  1440
gaagatatta aggggttggg agagttgaaa gagggtaaac ctaaaacccc taaacaaggt  1500
ggtggtggta gcgggcccg atggtatggt gataaaaagc gtaaaattta tgaatgggat  1560
tcccagcacg gtgagcttga agggtaccgc gccagtgatg gcgaacacct cggggcattc  1620
gatccaaaaa cgggtaagca ggttaaaggg ccggatccaa aacgaaacat taaaaaatat  1680
cttggctccg gatcggcttc tgggtcagat acaatgatag tagttgctac tccgacccg   1740
ggttttagct acgcgagcgg cttgacgtac ggcggtggtg cgtttgcggg tgcgcctgcg  1800
aacggtccgt cggaaggcca aatctttttc cagaccgttc tgccggcgta tcaatcccag  1860
aatctgtgta ttggtcaact ggcttggatg accgattaca ttaataagaa cggggtgggt  1920
aacccaaaaa cctgggaagt tatttcccaa aacgttctga ttttctgcag cgcggatact  1980
gccctggtgc ttaatccgcg catcgcggtg tacgacggct ccacaaaac taaatgggcg  2040
ccagccaagt tcaattttaa aacccagagc caggagaaat tctctggcaa cgttgaccac  2100
ccgattgctg ccttcggcca ttatctgtgg ggtgagggca gcaaaccgac gtcgacttg   2160
tctagcgttg gtctgaagat ccaggcaaac cagatcgacc cggttatgat tgcggttaaa  2220
aacaacgcag caggcaccta ccagatctcc ggcaacttca ccgtaatac ctttatcgac   2280
ggcgatattc cgggtttata tctgggtaac attaccatga aaacggaagg cacactcaag  2340
atcgacgcca aagggtaattg gaattataac ggtgtcgtgc gcgcgtttaa cgataccgac  2400
gacgctaatc cgtcgaccca ccgtagcaaa agcgcagaag atctgacgac gttgctgcgt  2460
ttgacgcaag gtacgccgta cgagatcaga atcccgggtg agctgaaggt gagcggtagc  2520
ggcaagaagt aa                                                      2532

SEQ ID NO: 59        moltype = AA   length = 846
FEATURE              Location/Qualifiers
source               1..846
                     mol_type = protein
                     organism = synthetic construct
SEQUENCE: 59
MSGGDGRGPG NSGLGHNGGQ ASGNVNGTSG KGGPSSGGGT DPNSGPGWGT THTPNGDIHN    60
YNPGEFGNGG SKPGGNGGNS GNHSGSSGGG QSSATAMAFG LPALATPGAE GLALSVSGDA   120
LSAAVADVLA ALKGPFKFGL WGIAIYGVLP SEIAKDDPKM MSKIVTSLPA DTVTETPVSS   180
LPLDQATVSV TKRVADIVKD ERQHIAVVTG RPMSVPVVDA KPTKRPGVFS VSIPGLPSLQ   240
VSVPKGVPAA KAPPKGIIAE KGDSRPAGFT AGGNSREAVI RFPKESGQKP VYVSVTDVLT   300
PAQVKQRLEE EKRRQQAWDA AHPEEGLKRE YDKAKAELDA EDKNIATLNS RIASTEKAIP   360
GARAAVQEAD KKVKEAEANK DDFVTYNPPH EYGSGWQDQV RYLDKDIQNQ NEKLKAAQTS   420
LNEMNESLSR DKAALSGAME SRKQKEKKAK DAENKLNEEK KKPRKGTKDY GHDYFPDPKT   480
EDIKGLGELK EGKPKTPKQG GGGKRARWYG DKKRKIYEWD SQHGELEGYR ASDGEHLGAF   540
DPKTGKQVKG PDPKRNIKKY LEAAAKEAAA KSDTMIVVAT PTPGFSYASG LTYGGGAFAG   600
APANGPSEGQ IFFQTVLPAY QSPNLCIGQL AWMTDYINKN GVGNPKTWEV ISQNVLIFCS   660
ADTALVLNPR IAVYDGFHKT KWAPAKFNFK TQSQEKFSGN VTTPIAAFGH YLWGEGKPRT   720
VDLSSVGLKI QANQIDPVMI AVKNNAAGTY QISGNFNRNT FIDGDIPGLY LGNITMKTEG   780
TLKIDAKGNW NYNGVVRAFN DTYDANPSTH RSKSAEDLTT LLRLTQGTPY EIRIPGELKV   840
SGSGKK                                                             846

SEQ ID NO: 60        moltype = DNA   length = 2541
FEATURE              Location/Qualifiers
source               1..2541
                     mol_type = other DNA
                     organism = synthetic construct
SEQUENCE: 60
atgagtggtg gagacggacg aggtccgggt aattcaggtc tgggacacaa tggtggtcag    60
gccagtggga atgtgaacgg tacatcaggt aaaggtggcc cttcatcagg tggtggtacg   120
gatccaaaca gcgggccggg ctggggtacg acgcatacac ctaacgggga tattcataac   180
tataaccccg gggagtttgg taacggcggg agtaaacccg gtggtaatgg cggtaacagc   240
```

```
ggcaatcata gcgggagctc tggtggcgga cagtcttcgg ccaccgcgat ggccttcggt    300
ctgcctgcct tggccactcc gggggctgaa ggactggctt tatccgtttc cggccgatgcg   360
ttgtcggccg ctgttgctga tgtgctggct gccctgaaag gtccgtttaa gtttggtctg    420
tggggattg cgatttacgg agtgctgcct tctgagatag caaaagatga tccgaaaatg     480
atgtcaaaaa tcgtgacgtc attgccggca gacacggtca cggagacgcc ggtcagctcc    540
ctgccgctgg accaggcgac ggtcagcgtc actaaacgtg tggcggatat tgtgaaggac   600
gagcggcagc atattgcggt tgtcaccggc cggccaatga gtgttcctgt ggtggatgcg    660
aaaccgacaa aacgtccggg ggtattcagt gtgtcgattc cgggtctccc gtctctgcag   720
gtgagcgtac ctaaaggtgt tccggccgcg aaagccccgc caaaaggcat tattgctgaa   780
aaaggtgatt cacgtccggc tggttttacg gccggtggta actcccgtga agccgttatt   840
cgtttcccga aagagagcgg acagaaaccg gtctatgtgt cggtgacgga tgttcttact   900
ccggcacagg taaaacagcg tctggaggaa gaaaagcgtc gccagcaggc atgggacgct    960
gctcacccgg aagaggggct gaaaagagag tatgataaag cgaaagctga gctggatgct   1020
gaagataaaa atattgcgac cttaaacagt cgcattgcat cgacagagaa ggcgatcccc    1080
ggtgcaaggg ctgctgttca ggaagccgat aaaaaggtaa aagaggcaga ggcaaataaa   1140
gatgattttg tgacttataa cccgcctcat gaatatggct ccgggtggca ggatcaggtt    1200
cgctatcttg ataaggatat tcagaatcag aatgagaaat taaaagctgc ccagacatct    1260
ttaaacgaaa tgaatgaatc cttatccagg gataaggctg cgctttccgg ggcgatggag   1320
agccggaaac aaaaggagaa aaaagcgaag gatgcagaaa ataaattaaa tgaggaaaag   1380
aaaaaacctc gtaagggaac taaagattac ggccatgatt attttcctga tcccaagact   1440
gaagatatta aggggttggg agagttgaaa gagggtaaac ctaaaacccc taaacaaggt   1500
ggtggtggta agcgggcccg atggtatggt gataaaaagc gtaaaattta tgaatgggat   1560
tcccagcacg gtgagcttga agggtaccgc gccagtgatg gcgaacacct cggggcattc   1620
gatccaaaaa cgggtaagca ggttaaaggg ccggatccaa aacgaaacat taaaaaatat   1680
cttgaagccg ctgccaagga ggcggccgct aaatcagata caatgatagt agttgctact   1740
ccgaccccgg gttttagcta cgcgacgcgc ttgacgtacg gcggtggtgc gtttgcgggt   1800
gcgcctgcga acggtccgtc ggaaggccaa atcttttttcc agaccgttct gccggcgtat   1860
caatccccga atctgtgtat tggtcaactg gcttggatga ccgattacat taataagaac   1920
ggggtgggta acccaaaaac ctgggaagtt atttcccaaa acgttctgat tttctgcagc   1980
gcggatactg ccctggtgct taatccgcgc atcgcggtgt acgacggctt ccacaaaact   2040
aaatgggcgc cagccaagtt caattttaaa acccagagcc aggagaaatt ctctggcaac   2100
gtgaccaccc cgattgctgc cttcggccat tatctgtggg gtgagggcaa gccgcgtacc   2160
gtcgacttgt ctagcgttgg tctgaagatc caggcaaacc agatcgaccc ggttatgatt   2220
gcggttaaaa acaacgcagc aggcacctac cagatctccg gcaacttcaa ccgtaatacc   2280
tttatcgacg gcgatattcc gggtttatat ctgggtaaca ttaccatgaa aaccgaaggc   2340
acactcaaga tcgacgccaa gggtaattgg aattataacg gtgtcgtgcg cgcgtttaac    2400
gatacctacg acgctaatcc gtcgacccac cgtagcaaaa gcgcagaaga tctgacgacg   2460
ttgctgcgtt tgacgcaagg tacgccgtac gagatcagaa tcccgggtga gctgaaggtg   2520
agcggtagcg gcaagaagta a                                              2541
```

```
SEQ ID NO: 61         moltype = AA  length = 662
FEATURE               Location/Qualifiers
source                1..662
                      mol_type = protein
                      organism = synthetic construct
SEQUENCE: 61
MPEETLTVVG GGNNSCNVSW GGGNGNNGGA GYSGKYGGTS YEGATSMLKL NDRVLIQLYL     60
CNPLNPDYIG APWGSDKDAE SIIRANRDKA GKFKANIQNW KTSGTGSLGS PVVGKSYSSG    120
DVDTYSVSFG KEKYNVLYNR KKDSFTTAYV DGGANKPEHS MKDQAIAVVK LYLLNESQAS    180
VIDTTSGIIT DSGKTLSGKL GDKYNTLAKE AADNIKNFQG KKLRSFNDAM ASINELANNP    240
KMKLSQADKT VVSNALKQMD LSALADRFKG LEKAFTWGDR LLKAEKIREG VVTGITTGDW    300
QKLAFEVEAM YLSGVAGAVA LGITTAMIST VAVALSLPAV AVSALTVVSV IGISILTSYI    360
DADKAKALNN AVLGLFKEAA AKEAAAKSDT MIVVATPTPG FSYASGLTYG GGAFAGAPAN    420
GPSEGQIFFQ TVLPAYQSPN LCIGQLAWMT DYINKNGVGN PKTWEVISQN VLIFCSADTA    480
LVLNPRIAVY DGFHKTKWAP AKFNFKTQSQ EKFSGNVTTP IAAFGHYLWG EGKPRTVDLS    540
SVGLKIQANQ IDPVMIAVKN NAAGTYQISG NFNRNTFIDG DIPGLYLGNI TMKTEGTLKI    600
DAKGNWNYNG VVRAFNDTYD ANPSTHRSKS AEDLTTLLRL TQGTPYEIRI PGELKVSGSG    660
KK                                                                  662
```

```
SEQ ID NO: 62         moltype = DNA  length = 1989
FEATURE               Location/Qualifiers
source                1..1989
                      mol_type = other DNA
                      organism = synthetic construct
SEQUENCE: 62
atgcctgaag aaacattgac tgtcgtaggt ggtggtaata cagctgtaa tgttagctgg      60
ggtggtggca atggtaacaa cggtggtgct ggctattctg gtaaatacgg tggtactagc    120
tatgaaggtg caactagtat gttgaagttg aatgaccgtg ttttaattca gctttatctt    180
tgcaatccgc ttaacccaga ttatattgga gcaccttggg gcagtgataa agatgcagaa    240
tcaattatca gagctaacag agataaagca ggaaagttca aggctaatat tcagaactgg    300
aaaacaagcg gtacaggttc tttaggtagc cctgtagttg ggaaatctta tagctcaggt    360
gatgtagata cttattcggt tagcttcgga aaagaaaaat acaatgtcct gtataaccgt    420
aaaaaagact cttttactac agcttatgtc gatggcggcg caaataaacc tgagcatagc    480
atgaaggatc aggctattgc cgttgttaaa ctttaccttc tcaacgaaag tcaggcatcg    540
gtaatcgata ctacatcggg aattattact gactctggta aaactcttag cgggaaatta    600
ggtgataaat acaacactct ggcgaaagaa gctgctgaca atataaaaaa cttccagggt    660
aagaaactcc gcagttttaa tgatgctatg gcatctatta tgaactagc taacaatcca     720
aagatgaagt taagtcaggc ggataaaaca gtcgtttcta tgcccctcaa acaaatggat    780
ttgtcagcac tagctgaccg attcaaaggg ttagagaaag cctttacttg gggtgatcga    840
```

```
cttcttaaag ccgagaaaat cagagaaggt gttgttactg gtattaccac aggggactgg   900
caaaagctgg cgtttgaggt tgaagctatg tacctcagtg gtgttgctgg cgccgtagcg   960
ttagggatta ctactgccat gattagcaca gtcgcagtcg ctttgtcact tccagctgta  1020
gctgtctctg cgcttactgt tgtgtccgtc attggcatct ctattctcac atcttatatc  1080
gatgctgata aggccaaagc actgaataat gcagtgcttg gcttatttaa agaagccgct  1140
gccaaggagg cggccgctaa atcagataca atgatagtag ttgctactcc gaccccgggt  1200
tttagctacg cgagcggctt gacgtacggc ggtggtgcgt ttgcgggtgc gcctgcgaac  1260
ggtccgtcg aaggccaaat cttttccag accgttctgc cggcgtatca atccccgaat    1320
ctgtgtattg gtcaactggc ttggatgacc gattacatta ataagaacgg ggtgggtaac  1380
ccaaaaacct gggaagttat ttcccaaaac gttctgattt tctgcagcgc ggatactgcc  1440
ctggtgctta atccgcgcat cgcggtgtac gacggcttcc acaaaactaa atgggcgcca  1500
gccaagttca atttttaaaac ccagagccag gagaaattct ctggcaacgt gaccaccccg  1560
attgctgcct tcggccatta tctgtggggt gagggcaagc cgcgtaccgt cgacttgtct  1620
agcgttggtc tgaagatcca ggcaaaccag atcgacccgg ttatgattgc ggttaaaaac  1680
aacgcagcag gcacctacca gatctccggc aacttcaacc gtaataccctt tatcgacggc  1740
gatattccgg gtttatatct gggtaacatt accatgaaaa cggaaggcac actcaagatc  1800
gacgccaagg gtaattggaa ttataacggt gtcgtgcgcg cgtttaacga tacctacgac  1860
gctaatccgt cgacccaccg tagcaaaagc gcagaagatc tgacgacgtt gctgcgtttg  1920
acgcaaggta cgccgtacga gatcagaatc ccgggtgagc tgaaggtgag cggtagcggc  1980
aagaagtaa                                                          1989
```

SEQ ID NO: 63          moltype = AA  length = 659
FEATURE                Location/Qualifiers
source                 1..659
                       mol_type = protein
                       organism = synthetic construct
SEQUENCE: 63

```
MPEETLTVVG GGNNSCNVSW GGGNGNNGGA GYSGKYGGTS YEGATSMLKL NDRVLIQLYL   60
CNPLNPDYIG APWGSDKDAE SIIRANRDKA GKFKANIQNW KTSGTGSLGS PVVGKSYSSG  120
DVDTYSVSFG KEKYNVLYNR KKDSFTTAYV DGGANKPEHS MKDQAIAVVK LYLLNESQAS  180
VIDTTSGIIT DSGKTLSGKL GDKYNTLAKE AADNIKNFQG KKLRSFNDAM ASINELANNP  240
KMKLSQADKT VVSNALKQMD LSALADRFKG LEKAFTWGDR LLKAEKIREG VVTGITTGDW  300
QKLAFEVEAM YLSGVAGAVA LGITTAMIST VAVALSLPAV AVSALTVVSV IGISILTSYI  360
DADKAKALNN AVLGLFKGSG SASGSDTMIV VATPTPGFSY ASGLTYGGGA FAGAPANGPS  420
EGQIFFQTVL PAYQSPNLCI GQLAWMTDYI NKNGVGNPKT WEVISQNVLI FCSADTALVL  480
NPRIAVYDGF HKTKWAPAKF NFKTQSQEKF SGNVTTPIAA FGHYLWGEGK PRTVDLSSVG  540
LKIQANQIDP VMIAVKNNAA GTYQISGNFN RNTFIDGDIP GLYLGNITMK TEGTLKIDAK  600
GNWNYNGVVR AFNDTYDANP STHRSKSAED LTTLLRLTQG TPYEIRIPGE LKVSGSGKK   659
```

SEQ ID NO: 64          moltype = DNA  length = 1980
FEATURE                Location/Qualifiers
source                 1..1980
                       mol_type = other DNA
                       organism = synthetic construct
SEQUENCE: 64

```
atgcctgaag aaacattgac tgtcgtaggt ggtggtaata acagctgtaa tgttagctgg    60
ggtggtggca atggtaacaa cggtggtgct ggctattctg gtaaatacgg tggtactagc   120
tatgaaggtg caactagtat gttgaagttg aataccgtg ttttaattca gctttatctt     180
tgcaatccgc ttaacccaga ttatattgga gcaccttggg gcagtgataa agatgcagaa   240
tcaattatca gagctaacag agataaagca ggaaagttca aggctaatat tcagaactgg   300
aaaacaagcg gtacaggttc tttaggtagc cctgtagttg ggaaatctta tagctcaggt   360
gatgtagata cttattcggt tagcttcgga aaagaaaaat acaatgtcct gtataaccgt   420
aaaaaagact ctttttactac agccttatgtc gatggcggcg caaataaacc tgagcatagc   480
atgaaggatc aggctattgc cgttgttaaa ctttaccttc tcaacgaaag tcaggcatcg   540
gtaatcgata ctacatcggg aattattact gactctggta aaactcttag cgggaaatta   600
ggtgataaat acaacactct ggcgaaagaa gctgctgaca atataaaaaa cttccagggt   660
aagaaactcc gcagtttaa tgatgctatg gcatctatta tgaactagc taacaatcca    720
aagatgaagt taagtcaggc ggataaaaca gtcgtttcta atgccctcaa acaaatggat   780
ttgtcagcac tagctgaccg attcaaaggg ttagagaaag cctttacttg gggtgatcga   840
cttcttaaag ccgagaaaat cagagaaggt gttgttactg gtattaccac aggggactgg   900
caaaagctgg cgtttgaggt tgaagctatg tacctcagtg gtgttgctgg cgccgtagcg   960
ttagggatta ctactgccat gattagcaca gtcgcagtcg ctttgtcact tccagctgta  1020
gctgtctctg cgcttactgt tgtgtccgtc attggcatct ctattctcac atcttatatc  1080
gatgctgata aggccaaagc actgaataat gcagtgcttg gcttatttaa aggctccgga  1140
tcggcttctg gtcagatac aatgatagta gttgctactc cgaccccggg ttttagctac   1200
gcgagcggct tgacgtacgg cggtggtgcg tttgcgggtg cgcctgcgaa cggtccgtcg   1260
gaaggccaaa tcttttttcca gaccgttctg ccggcgtatc aatccccgaa tctgtgtatt   1320
ggtcaactgg cttggatgac cgattacatt aataagaacg gggtgggtaa cccaaaaacc   1380
tgggaagtta tttcccaaaa cgttctgatt tctgcagcg cggatactgc cctggtgctt    1440
aatccgcgca tcgcggtgta cgacggcttc cacaaaacta aatgggcgcc agccaagttc   1500
aatttttaaaa cccagagcca ggagaaattc tctggcaacg tgaccacccc gattgctgcc   1560
ttcggccatt atctgtgggg tgagggcaag ccgcgtaccg tcgacttgtc tagcgttggt   1620
ctgaagatcc aggcaaacca gatcgacccg gttatgattg cggttaaaaa caacgcagca   1680
ggcacctacc agatctccgg caacttcaac cgtaatacct ttatcgacgg cgatattccg   1740
ggtttatatc tgggtaacat taccatgaaa acgaaggca cactcaagat cgacgccaag    1800
ggtaattgga attataacgg tgtcgtgcgc gcgtttaacg atacctacga cgctaatccg   1860
tcgacccacc gtagcaaaag cgcagaagat ctgacgacgt tgctgcgttt gacgcaaggt   1920
acgccgtacg agatcagaat cccgggtgag ctgaaggtga gcggtagcgg caagaagtaa   1980
```

```
SEQ ID NO: 65           moltype = AA  length = 672
FEATURE                 Location/Qualifiers
source                  1..672
                        mol_type = protein
                        organism = synthetic construct
SEQUENCE: 65
MPEETLTVVG GGNNSCNVSW GGGNGNNGGA GYSGKYGGTS YEGATSMLKL NDRVLIQLYL    60
CNPLNPDYIG APWGSDKDAE SIIRANRDKA GKFKANIQNW KTSGTGSLGS PVVGKSYSSG   120
DVDTYSVSFG KEKYNVLYNR KKDSFTTAYV DGGANKPEHS MKDQAIAVVK LYLLNESQAS   180
VIDTTSGIIT DSGKTLSGKL GDKYNTLAKE AADNIKNFQG KKLRSFNDAM ASINELANNP   240
KMKLSQADKT VVSNALKQMD LSALADRFKG LEKAFTWGDR LLKAEKIREG VVTGITTGDW   300
QKLAFEVEAM YLSGVAGAVA LGITTAMIST VAVALSLPAV AVSALTVVSV IGISILTSYI   360
DADKAKALNN AVLGLFKEAA AKEAAAKEAA AKEAAAKSDT MIVVATPTPG FSYASGLTYG   420
GGAFAGAPAN GPSEGQIFFQ TVLPAYQSPN LCIGQLAWMT DYINKNGVGN PKTWEVISQN   480
VLIFCSADTA LVLNPRIAVY DGFHKTKWAP AKFNFKTQSQ EKFSGNVTTP IAAFGHYLWG   540
EGKPRTVDLS SVGLKIQANQ IDPVMIAVKN NAAGTYQISG NFNRNTFIDG DIPGLYLGNI   600
TMKTEGTLKI DAKGNWNYNG VVRAFNDTYD ANPSTHRSKS AEDLTTLLRL TQGTPYEIRI   660
PGELKVSGSG KK                                                     672

SEQ ID NO: 66           moltype = DNA  length = 2019
FEATURE                 Location/Qualifiers
source                  1..2019
                        mol_type = other DNA
                        organism = synthetic construct
SEQUENCE: 66
atgcctgaag aaacattgac tgtcgtaggt ggtggtaata acagctgtaa tgttagctgg    60
ggtggtggca atggtaacaa cggtggtgct ggctattctg gtaaatacgg tggtactagc   120
tatgaaggtg caactagtat gttgaagttg aatgaccgtg tttaattca gctttatctt    180
tgcaatccgc ttaacccaga ttatattgga gcaccttggg gcagtgataa agatgcagaa   240
tcaattatca gagctaacag agataaagca ggaaagttca aggctaatat tcagaactgg   300
aaaacaagcg gtacaggttc tttaggtagc cctgtagttg ggaaatctta tagctcaggt   360
gatgtagata cttattcggt tagcttcgga aaagaaaat acaatgtcct gtataaccgt   420
aaaaaagact cttttactac agcttatgtc gatggcggcg caaataaacc tgagcatagc   480
atgaaggatc aggctattgc cgttgttaaa ctttaccttc tcaacgaaag tcaggcatcg   540
gtaatcgata ctacatcggg aattattact gactctggta aaactcttag cggaaatta   600
ggtgataaat acaacactct ggcgaaagaa gctgctgaca atataaaaaa cttccagggt   660
aagaaactcc gcagttttaa tgatgctatg gcatcatta atgaactagc taacaatcca   720
aagatgaagt taagtcaggc ggataaaaca gtcgtttcta atgccctcaa acaaatggat   780
ttgtcagcac tagctgaccg attcaaaggg ttagagaaag cctttacttg gggtgatcga   840
cttcttaaag ccgagaaaat cagagaaggt gttgttactg gtattaccac aggggactgg   900
caaaagctgg cgtttgaggt tgaagctatg tacctcagtg gtgttgctgg cgccgtagcg   960
ttagggatta ctactgccat gattagcaca gtcgcagtcg ctttgtcact tccagctgta  1020
gctgtctctg cgcttactgt tgtgtccgtc attggcatct ctattctcac atcttatatc  1080
gatgctgata aggccaaagc actgaataat gcagtgcttg gcttatttaa agaagccgct  1140
gccaaggagg cggccgctaa agaagccgct gccaaggagg cggccgctaa atcagataca  1200
atgatagtag ttgctactcc gaccccgggt tttagctacg cgagcggctt gacgtacggc  1260
ggtggtgcgt ttgcgggtgc gcctgcgaac ggtccgtcgg aaggccaaat cttttccag   1320
accgttctgc cggcgtatca atccccgaat ctgtgtattg gtcaactggc ttggatgacc  1380
gattacatta ataagaacgg ggtgggtaac ccaaaaacct gggaagttat ttcccaaaac  1440
gttctgattt tctgcagcgc ggatactgcc ctggtgctta atccgcgcat cgcggtgtac  1500
gacggcttcc acaaaactaa atgggcgcca gccaagttca atttaaaac ccagagccag  1560
gagaaattct ctggcaacgt gaccaccccg attgctgcct cggccatta tctgtggggt  1620
gagggcaagc cgcgtaccgt cgacttgtct agcgttggtc tgaagatcca ggcaaaccag  1680
atcgacccgg ttatgattgc ggttaaaaac aacgcagcag gcacctacca gatctccggc  1740
aacttcaacc gtaatacctt tatcgacggc gatattccgg gtttatatct gggtaacatt  1800
accatgaaaa cggaaggcac actcaagatc gacgccaagg gtaattggaa ttataacggt  1860
gtcgtgcgcg cgtttaacga tacctacgac gctaatccgt cgacccaccg tagcaaaagc  1920
gcagaagatc tgacgacgtt gctgcgtttg acgcaaggta cgccgtacga gatcagaatc  1980
ccgggtgagc tgaaggtgag cggtagcggc aagaagtaa                         2019

SEQ ID NO: 67           moltype = AA  length = 275
FEATURE                 Location/Qualifiers
source                  1..275
                        mol_type = protein
                        organism = synthetic construct
SEQUENCE: 67
MSDTMIVVAT PTPGFSYASG LTYGGGMFSP TISGPSEGQI FLQVTLPYYQ SEKFCADQLN    60
WLVQYIKKHG ASDPMTIQVA ANNIRYLCNA DTNLVKNPKT LVYDAFHSRS PAPANYDYRS   120
MNLKQMSGSV VTPGAAFAHY LWGNGETRFV NLPDVGLKVT PQQIPELMKL VNSGVTGAIP   180
VSVKFSRDTS TDSITAGAYL GHITLQTEGT LNVTGNGAWT YNGVIRAYDD TYDFNLGNFR   240
GPIAESLTFL GSTFSGKPYQ ISLPGQINIS GSGKK                             275

SEQ ID NO: 68           moltype = DNA  length = 828
FEATURE                 Location/Qualifiers
source                  1..828
                        mol_type = other DNA
                        organism = synthetic construct
SEQUENCE: 68
atgtcagata caatgatagt agttgctact ccgaccccgg gttttagcta cgcgagcggc    60
```

-continued

```
ttgacgtacg gtggcggtat gtttagcccg accatcagcg gtccgagcga gggtcagatt    120
tttctgcaag tgaccctgcc gtactatcag agcgaaaagt tctgcgcgga tcagctgaac    180
tggctggtgc aatatattaa gaaacacggc gcgagcgacc cgatgaccat ccaagttgcg    240
gcgaacaaca ttcgttacct gtgcaacgcg gacaccaacc tggtgaagaa cccgaaaacc    300
ctggtttatg atgcgttcca cagccgtagc ccggcgccgg cgaactacga ctatcgtagc    360
atgaacctga gcagatgag cggcagcgtg gttacgccgg gtgcggcgtt tgcgcactac    420
ctgtggggca acggcgagac ccgtttTgtt aacctgccgg atgtgggtct gaaggttacc    480
ccgcagcaaa tcccggaact gatgaaactg gtgaacagcg cgttaccgg tgcgattccg    540
gtgagcgtta aattcagccg tgacaccagc accgatagca tcaccgcggg cgcgtacctg    600
ggtcacatta ccctgcaaac cgagggcacc ctgaacgtga ccggcaacgg tgcgtggacc    660
tataacggtg ttatccgtgc gtacgacgat acctatgact tcaacctggg caactttcgt    720
ggtccgattg cggaaagcct gaccttcctg ggcagcacct ttagcggcaa gccgtaccag    780
atcagcctgc cgggtcaaat caacattagc ggcagcggta aaaagtaa                 828
```

SEQ ID NO: 69          moltype = AA  length = 502
FEATURE                Location/Qualifiers
source                 1..502
                       mol_type = protein
                       organism = synthetic construct
SEQUENCE: 69
```
MSDTMIVVAT PTPGFSYASG LTYGGGAFAG APANGPSEGQ IFFQTVLPAY QSPNLCIGQL    60
AWMTDYINKN GVGNPKTWEV ISQNVLIFCS ADTALVLNPR IAVYDGFHKT KWAPAKFNFK   120
TQSQEKFSGN VTTPIAAFGH YLWGEGKPRT VDLSSVGLKI QANQIDPVMI AVKNNAAGTY   180
QISGNFNRNT FIDGDIPGLY LGNITMKTEG TLKIDAKGNW NYNGVVRAFN DTYDANPSTH   240
RSKSAEDLTT LLRLTQGTPY EIRIPGELKV SGSGKKEAAA KEAAAKGVAL DRTRVDPQAV   300
GNEVLKRNAD KLNAMRGAEY GANVKVSGTD IRMNGGNSAD MLKQDVFNWR KELAQFEAYR   360
GEAYKDADGY SVGLGHYLGS GNAGAGTTVT PEQAAQWFAE DTDRALDQGV RLADELGVTN   420
NASILGLAGM AFQMGEGRAR QFRNTFQAIK DRNKEAFEAG VRNSKWYTQT PNRAEAFIKR   480
MAPHFDTPSQ IGVDWYSAAT AE                                            502
```

SEQ ID NO: 70          moltype = DNA  length = 1509
FEATURE                Location/Qualifiers
source                 1..1509
                       mol_type = other DNA
                       organism = synthetic construct
SEQUENCE: 70
```
atgtcagata caatgatagt agttgctact ccgaccccgg gttttagcta cgcgagcggc    60
ttgacgtacg gcggtggtgc gtttgcgggt gcgcctgcga acggtccgtc ggaaggccaa   120
atcttttcc agaccgttct gccggcgtat caatcccgca atctgtgtat tggtcaactg   180
gcttggatga ccgattacat taataagaac ggggtgggta acccaaaaac ctgggaagtt   240
atttcccaaa acgttctgat tttctgcagc gcggatactg ccctggtgct taatccgcgc   300
atcgcggtgt acgacggctt ccacaaaact aaatgggcgc cagccaagtt caattttaaa   360
acccagagcc aggagaaatt ctctggcaac gtgaccaccc cgattgctgc cttcggccat   420
tatctgtggg gtgagggcaa gccgcgtacc gtcgacttgt ctagcgttgg tctgaagatc   480
caggcaaacc agatcgaccc ggttatgatt gcggttaaaa acaacgcagc aggcacctac   540
cagatctccg gcaacttcaa ccgtaatacc tttatcgacg gcgatattcc gggtttatat   600
ctgggtaaca ttaccatgaa aacggaaggc acactcaaga tcgacgccaa gggtaattgg   660
aattataacg gtgtcgtgcg cgcgtttaac gatacctacg acgctaatcc gtcgacccac   720
cgtagcaaaa gcgcagaaga tctgacgacg ttgctgcgtt tgacgcaagg tacgccgtac   780
gagatcagaa tcccgggtga gctgaaggtg agcggtagcg gcaagaagga gccgctgcc   840
aaggaggcgg ccgctaaagg tgtggccctg gaccgcagc gggttgatcc ccaggcagtc   900
ggcaacgagg tgctcaagcg caacgcggat aagctgaatg cgatgcgggg cgccgagtac   960
ggtgccaacg tcaaggtcag cggcacggac attcgcatga cgggggtaa cagtgccggc  1020
atgctgaagc aggacgtgtt caactggcgg aaggaactgg ctcagttcga ggcttaccga  1080
ggggagcgt ataaggatgc cgatggttat agtgtgggcc tggggcatta cctgggcagt  1140
ggcaatgctg gggcaggtac tacagtcacg cctgagcaag ccggcagtg gttccgcgag  1200
gacaccgacc gcgcactcga ccagggtgtg aggttggccg acgagctggg cgttacgaac  1260
aatgcctcta tcctgggatt ggccggtatg gccttccaga tgggcgaagg acgtgcccgg  1320
cagttccgta acacccttcca ggcgatcaag gatcgcaaca aggaagcctt cgaggctggt  1380
gtgcgaaaca gcaagtggta cacgcagacg cccaaccggg ccgaggcatt catcaagcgc  1440
atggcgcccc acttcgatac accgagtcaa atcggtgtcg attggtacag cgccgcaaca  1500
gcggagtga                                                          1509
```

SEQ ID NO: 71          moltype = AA  length = 593
FEATURE                Location/Qualifiers
source                 1..593
                       mol_type = protein
                       organism = synthetic construct
SEQUENCE: 71
```
MPEETLTVVG GGNNSCNVSW GGGNGNNGGA GYSGKYGGTS YEGATSMLKL NDRVLIQLYL    60
CNPLNPDYIG APWGSDKDAE SIIRANRDKA GKFKANIQNW KTSGTGSLGS PVVGKSYSSG   120
DVDTYSVSFG KEKYNVLYNR KKDSFTTAYV DGGANKPEHS MKDQAIAVVK LYLLNESQAS   180
VIDTTSGIIT DSGKTLSGKL GDKYNTLAKE AADNIKNFQG KKLRSFNDAM ASINELANNP   240
KMKLSQADKT VVSNALKQMD LSALADRFKG LEKAFTWGDR LLKAEKIREG VVTGITTGDW   300
QKLAFEVEAM YLSGVAGAVA LGITTAMIST VAVALSLPAV AVSALTVVSV IGISILTSYI   360
DADKAKALNN AVLGLFKGVA LDRTRVDPQA VGNEVLKRNA DKLNAMRGAE YGANVKVSGT   420
DIRMNGGNSA GMLKQDVFNW RKELAQFEAY RGEAYKDADG YSVGLGHYLG SGNAGAGTTV   480
TPEQAAQWFA EDTDRALDQG VRLADELGVT NNASILGLAG MAFQMGEGRA RQFRNTFQAI   540
KDRNKEAFEA GVRNSKWYTQ TPNRAEAFIK RMAPHFDTPS QIGVDWYSAA TAE           593
```

```
SEQ ID NO: 72          moltype = DNA   length = 1782
FEATURE                Location/Qualifiers
source                 1..1782
                       mol_type = other DNA
                       organism = synthetic construct
SEQUENCE: 72
atgcctgaag aaacattgac tgtcgtaggt ggtggtaata acagctgtaa tgttagctgg     60
ggtggtggca atggtaacaa cggtggtgct ggctattctg gtaaatacgg tggtactagc    120
tatgaaggtg caactagtat gttgaagttg aatgaccgtg ttttaattca gctttatctt    180
tgcaatccgc ttaacccaga ttatattgga gcaccttggg gcagtgataa agatgcagaa    240
tcaattatca gagctaacag agataaagca ggaaagttca aggctaatat tcagaactgg    300
aaaacaagcg gtacaggttc tttaggtagc cctgtagttg ggaaatctta tagctcaggt    360
gatgtagata cttattcggt tagcttcgga aaagaaaat acaatgtcct gtataaccgt    420
aaaaaagact cttttactac agcttatgtc gatggcggcg caaataaacc tgagcatagc    480
atgaaggatc aggctattgc cgttgttaaa ctttaccttc tcaacgaaag tcaggcatcg    540
gtaatcgata ctacatcggg aattattact gactctggta aaactcttag cgggaaatta    600
ggtgataaat acaacactct ggcgaaagaa gctgctgaca atataaaaaa cttccagggt    660
aagaaactcc gcagttttaa tgatgctatg gcatctatta tgaactagc taacaatcca    720
aagatgaagt taagtcaggc ggataaaaca gtcgtttcta atgccctcaa acaaatggat    780
ttgtcagcac tagctgaccg attcaaaggg ttagagaaag cctttacttg gggtgatcga    840
cttcttaaag ccgagaaaat cagagaaggt gttgttactg gtattaccac aggggactgg    900
caaaagctgg cgtttgaggt tgaagctatg tacctcagtg gtgttgctgg cgccgtagcg    960
ttagggatta ctactgccat gattagcaca gtcgcagtcg ctttgtcact tccagctgta   1020
gctgtctctg cgcttactgt tgtgtccgtc attggcatct ctattctcac atcttatatc   1080
gatgctgata aggccaaagc actgaataat gcagtgcttg gctcatttaa aggtgtggcc   1140
ctggaccgca cgcggggttga tccccaggca gtcggcaacg aggtgctcaa gcgcaacgcg   1200
gataagctga atgcgatgcg gggcgccgag tacggtgcca acgtcaaggt cagcggcacg   1260
gacattcgca tgaacggggg taacagtgcc ggcatgctga agcaggacgt gttcaactgg   1320
cggaaggaac tggctcagtt cgaggcttac cgagggagg cgtataagga tgccgatggt   1380
tatagtgtgg gcctggggca ttacctgggc agtggcaatg ctggggcagg tactacagtc   1440
acgcctgagc aagccgcgca gtggttcgcc gaggacaccg accgcgcact cgaccagggt   1500
gtgaggttgg ccgacgagct gggcgttacg aacaatgcct ctatcctggg attggccggt   1560
atggccttcc agatgggcga aggacgtgcc cggcagttcc gtaacacctt ccaggcgatc   1620
aaggatcgca acaaggaagc cttcgaggct ggtgtgcgaa acagcaagtg gtacacgcag   1680
acgcccaacc gggccgaggc attcatcaag cgcatggcgc cccacttcga tacaccgagt   1740
caaatcggtg tcgattggta cagcgccgca acagcggagt ga                      1782

SEQ ID NO: 73          moltype = AA   length = 600
FEATURE                Location/Qualifiers
source                 1..600
                       mol_type = protein
                       organism = synthetic construct
SEQUENCE: 73
MPEETLTVVG GGNNSCNVSW GGGNGNNGGA GYSGKYGGTS YEGATSMLKL NDRVLIQLYL     60
CNPLNPDYIG APWGSDKDAE SIIRANRDKA GKFKANIQNW KTSGTGSLGS PVVGKSYSSG    120
DVDTYSVSFG KEKYNVLYNR KKDSFTTAYV DGGANKPEHS MKDQAIAVVK LYLLNESQAS    180
VIDTTSGIIT DSGKTLSGKL GDKYNTLAKE AADNIKNFQG KKLRSFNDAM ASINELANNP    240
KMKLSQADKT VVSNALKQMD LSALADRFKG LEKAFTWGDR LLKAEKIREG VVTGITTGDW    300
QKLAFEVEAM YLSGVAGAVA LGITTAMIST VAVALSLPAV AVSALTVVSV IGISILTSYI    360
DADKAKALNN AVLGLFKGSG SASGGVALDR TRVDPQAVGN EVLKRNADKL NAMRGAEYGA    420
NVKVSGTDIR MNGGNSAGML KQDVFNWRKE LAQFEAYRGE AYKDADGYSV GLGHYLGSGN    480
AGAGTTVTPE QAAQWFAEDT DRALDQGVRL ADELGVTNNA SILGLAGMAF QMGEGRARQF    540
RNTFQAIKDR NKEAFEAGVR NSKWYTQTPN RAEAFIKRMA PHFDTPSQIG VDWYSAATAE    600

SEQ ID NO: 74          moltype = DNA   length = 1803
FEATURE                Location/Qualifiers
source                 1..1803
                       mol_type = other DNA
                       organism = synthetic construct
SEQUENCE: 74
atgcctgaag aaacattgac tgtcgtaggt ggtggtaata acagctgtaa tgttagctgg     60
ggtggtggca atggtaacaa cggtggtgct ggctattctg gtaaatacgg tggtactagc    120
tatgaaggtg caactagtat gttgaagttg aatgaccgtg ttttaattca gctttatctt    180
tgcaatccgc ttaacccaga ttatattgga gcaccttggg gcagtgataa agatgcagaa    240
tcaattatca gagctaacag agataaagca ggaaagttca aggctaatat tcagaactgg    300
aaaacaagcg gtacaggttc tttaggtagc cctgtagttg ggaaatctta tagctcaggt    360
gatgtagata cttattcggt tagcttcgga aaagaaaat acaatgtcct gtataaccgt    420
aaaaaagact cttttactac agcttatgtc gatggcggcg caaataaacc tgagcatagc    480
atgaaggatc aggctattgc cgttgttaaa ctttaccttc tcaacgaaag tcaggcatcg    540
gtaatcgata ctacatcggg aattattact gactctggta aaactcttag cgggaaatta    600
ggtgataaat acaacactct ggcgaaagaa gctgctgaca atataaaaaa cttccagggt    660
aagaaactcc gcagttttaa tgatgctatg gcatctatta tgaactagc taacaatcca    720
aagatgaagt taagtcaggc ggataaaaca gtcgtttcta atgccctcaa acaaatggat    780
ttgtcagcac tagctgaccg attcaaaggg ttagagaaag cctttacttg gggtgatcga    840
cttcttaaag ccgagaaaat cagagaaggt gttgttactg gtattaccac aggggactgg    900
caaaagctgg cgtttgaggt tgaagctatg tacctcagtg gtgttgctgg cgccgtagcg    960
ttagggatta ctactgccat gattagcaca gtcgcagtcg ctttgtcact tccagctgta   1020
gctgtctctg cgcttactgt tgtgtccgtc attggcatct ctattctcac atcttatatc   1080
```

-continued

```
gatgctgata aggccaaagc actgaataat gcagtgcttg gcttatttaa aggctccgga   1140
tcggcttctg ggggtgtggc cctgaccgc acgcgggttg atccccaggc agtcggcaac   1200
gaggtgctca agcgcaacgc ggataagctg aatgcgatgc ggggcgccga gtacggtgcc   1260
aacgtcaagg tcagcggcac ggacattcgc atgaacgggg gtaacagtgc cggcatgctg   1320
aagcaggacg tgttcaactg gcggaaggaa ctggctcagt tcgaggctta ccgaggggag   1380
gcgtataagg atgccgatgg ttatagtgtg ggcctgggc attacctggg cagtggcaat   1440
gctgggcag gtactacagt cacgcctgag caagccgcgc agtggttcgc cgaggacacc   1500
gaccgcgcac tcgaccaggg tgtgaggttg gccgacgagc tgggcgttac gaacaatgcc   1560
tctatcctgg gattggccgg tatggccttc cagatgggcg aaggacgtgc ccggcagttc   1620
cgtaacacct tccaggcgat caaggatcgc aacaaggaag ccttcgaggc tggtgtgcga   1680
aacagcaagt ggtacacgca gacgcccaac cgggccgagg cattcatcaa gcgcatggcg   1740
ccccacttcg atacaccgag tcaaatcggt gtcgattggt acagcgccgc aacagcggag   1800
tga                                                                  1803
```

```
SEQ ID NO: 75           moltype = AA   length = 603
FEATURE                 Location/Qualifiers
source                  1..603
                        mol_type = protein
                        organism = synthetic construct
SEQUENCE: 75
MPEETLTVVG GGNNSCNVSW GGGNGNNGGA GYSGKYGGTS YEGATSMLKL NDRVLIQLYL   60
CNPLNPDYIG APWGSDKDAE SIIRANRDKA GKFKANIQNW KTSGTGSLGS PVVGKSYSSG   120
DVDTYSVSFG KEKYNVLYNR KKDSFTTAYV DGGANKPEHS MKDQAIAVVK LYLLNESQAS   180
VIDTTSGIIT DSGKTLSGKL GDKYNTLAKE AADNIKNFQG KKLRSFNDAM ASINELANNP   240
KMKLSQADKT VVSNALKQMD LSALADRFKG LEKAFTWGDR LLKAEKIREG VVTGITTGDW   300
QKLAFEVEAM YLSGVAGAVA LGITTAMIST VAVALSLPAV AVSALTVVSV IGISILTSYI   360
DADKAKALNN AVLGLFKEAA AKEAAAKGVA LDRTRVDPQA VGNEVLKRNA DKLNAMRGAE   420
YGANVKVSGT DIRMNGGNSA GMLKQDVFNW RKELAQFEAY RGEAYKDADG YSVGLGHYLG   480
SGNAGAGTTV TPEQAAQWFA EDTDRALDQG VRLADELGVT NNASILGLAG MAFQMGEGRA   540
RQFRNTFQAI KDRNKEAFEA GVRNSKWYTQ TPNRAEAFIK RMAPHFDTPS QIGVDWYSAA   600
TAE                                                                  603
```

```
SEQ ID NO: 76           moltype = DNA   length = 1812
FEATURE                 Location/Qualifiers
source                  1..1812
                        mol_type = other DNA
                        organism = synthetic construct
SEQUENCE: 76
atgcctgaag aaacattgac tgtcgtaggt ggtggtaata acagctgtaa tgttagctgg   60
ggtggtggca atggtaacaa cggtggtgct ggctattctg gtaaatacgg tggtactagc   120
tatgaaggtg caactagtat gttgaagttg aatgaccgtg ttttaattca gctttatctt   180
tgcaatccgc ttaacccaga ttatattgga gcaccttggg gcagtgataa agatgcagaa   240
tcaattatca gagctaacag agataaagca ggaaagttca gctaatat tcagaactgg   300
aaaacaagcg gtacaggttc tttaggtagc cctgtagttg ggaaatctta tagctcaggt   360
gatgtagata cttattcggt tagcttcgga aaagaaaat acaatgtcct gtataaccgt   420
aaaaaagact ctttttactac agcttatgtc gatggcggcg caaataaacc tgagcatagc   480
atgaaggatc aggctattgc cgttgttaaa ctttaccttc tcaacgaaag tcaggcatcg   540
gtaatcgata ctacatcggg aattattact gactctggta aaactcttag cgggaaatta   600
ggtgataaat acaacactct ggcgaaagaa gctgctgaca atataaaaaa cttccagggt   660
aagaaactcc gcagtttta tgatgctatg gcatcatta atgaactagc taacaatcca   720
aagatgaagt taagtcaggc ggataaaaca gtcgtttcta atgccctcaa acaaatggat   780
ttgtcagcac tagctgaccg attcaaaggg ttagagaaag cctttacttg gggtgatcga   840
cttcttaaag ccgagaaaat cagagaaggt gttgttactg gtattaccac aggggactgg   900
caaaagctgg cgtttgaggt tgaagctatg tacctcagtg gtgttgctgg cgccgtagcg   960
ttagggatta ctactgccat gattagcaca gtcgcagtcg ctttgtcact tccagctgta   1020
gctgtctctg cgcttactgt tgtgtccgtc attggcatct ctattctcac atcttatatc   1080
gatgctgata aggccaaagc actgaataat gcagtgcttg gcttatttaa agaagccgct   1140
gccaaggagg cggccgctaa aggtgtggc ctgaccgca cgcgggttga tccccaggca   1200
gtcggcaacg aggtgctcaa gcgcaacgcg gataagctga atgcgatgcg gggcgccgag   1260
tacggtgcca acgtcaaggt cagcggcacg gacattcgca tgaacggggg taacagtgcc   1320
ggcatgctga gcaggacgt gttcaactgg cggaaggaac tggctcagtt cgaggcttac   1380
cgaggggagg cgtataagga tgccgatggt tatagtgtgg gcctggggca ttacctggc   1440
agtggcaatg ctggggcagg tactacagtc acgcctgagc aagccgcgca gtggttcgcc   1500
gaggacaccg accgcgcact cgaccaggg tgtgaggttgg ccgacgagct gggcgttacg   1560
aacaatgcct ctatcctggg attggccggt atggccttcc agatgggcga aggacgtgcc   1620
cggcagttcc gtaacacctt ccaggcgatc aaggatcgca acaaggaagc cttcgaggct   1680
ggtgtgcgaa acagcaagtg gtacacgcag acgcccaacc gggccgaggc attcatcaag   1740
cgcatgcgc cccacttcga tacaccgagt caaatcggtt cgattggta cagcgccgca   1800
acagcggagt ga                                                       1812
```

```
SEQ ID NO: 77           moltype = AA   length = 6
FEATURE                 Location/Qualifiers
source                  1..6
                        mol_type = protein
                        organism = synthetic construct
SEQUENCE: 77
HHHHHH                                                                6
```

What is claimed is:

1. A polypeptide comprising one or more translocation domains, one or more receptor-binding domains, and a killing domain, wherein each of the domains is derived from a naturally-occurring klebicin, wherein the killing domain and at least one of the receptor-binding domains are derived from two different naturally-occurring klebicins, and wherein the polypeptide comprises the amino acid sequence of SEQ ID NO: 45.

2. A nucleic acid comprising a polynucleotide sequence encoding the polypeptide of claim 1.

3. An expression cassette comprising a polynucleotide sequence encoding the polypeptide of claim 1.

4. A vector comprising the expression cassette of claim 3.

5. A host cell comprising the expression cassette of claim 3.

6. A method of recombinantly producing a polypeptide, comprising culturing the host cell of claim 5 under conditions permitting expression of the polypeptide encoded by the expression cassette.

7. A composition comprising the polypeptide of claim 1 and a physiologically acceptable excipient.

8. The composition of claim 7, formulated for administration by injection or inhalation.

9. A method for suppressing growth of *Klebsiella pneumoniae*, comprising applying an effective amount of the composition of claim 7 to a location where *Klebsiella pneumoniae* is present.

10. The method of claim 9, wherein the composition is applied to a patient suffering from a *Klebsiella pneumoniae* infection by injection.

11. The method of claim 9, wherein the composition is applied to a patient suffering from a *Klebsiella pneumoniae* infection by inhalation.

12. A kit for suppression of growth of *Klebsiella pneumoniae*, comprising a first container containing a composition comprising an effective amount of the polypeptide of claim 1.

13. The kit of claim 12, wherein the composition is formulated for injection.

14. The kit of claim 12, wherein the composition is formulated for inhalation.

15. The kit of claim 12, further comprising an instruction manual.

* * * * *